US008722033B2

(12) United States Patent
Towne et al.

(10) Patent No.: US 8,722,033 B2
(45) Date of Patent: May 13, 2014

(54) HUMAN IL-23 ANTIGEN BINDING PROTEINS

(75) Inventors: Jennifer E. Towne, Seattle, WA (US); Janet D. Cheng, Seattle, WA (US); Jason C. O'Neill, Brier, WA (US); Yu Zhang, Shoreline, WA (US); Yu Sun, Seattle, WA (US); Heather Cerne, Seattle, WA (US); Derek E. Piper, Santa Clara, CA (US); Randal R. Ketchem, Snohomish, WA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/504,449

(22) PCT Filed: Oct. 26, 2010

(86) PCT No.: PCT/US2010/054148
§ 371 (c)(1),
(2), (4) Date: Aug. 31, 2012

(87) PCT Pub. No.: WO2011/056600
PCT Pub. Date: May 12, 2011

(65) Prior Publication Data
US 2013/0004501 A1 Jan. 3, 2013

Related U.S. Application Data

(60) Provisional application No. 61/381,287, filed on Sep. 9, 2010, provisional application No. 61/254,982, filed on Oct. 26, 2009.

(51) Int. Cl.
*C07K 16/24* (2006.01)
*A61K 39/395* (2006.01)

(52) U.S. Cl.
CPC ............... *A61K 39/395* (2013.01); *C07K 16/24* (2013.01)
USPC ..................... 424/85.2; 530/387.1; 530/388.1; 530/388.23

(58) Field of Classification Search
None
See application file for complete search history.

(56) References Cited

U.S. PATENT DOCUMENTS

| | | |
|---|---|---|
| 4,399,216 A | 8/1983 | Axel et al. |
| 4,740,461 A | 4/1988 | Kaufman |
| 4,751,180 A | 6/1988 | Cousens et al. |
| 4,816,567 A | 3/1989 | Cabilly et al. |
| 4,912,040 A | 3/1990 | Kaufman et al. |
| 4,935,233 A | 6/1990 | Bell et al. |
| 4,946,778 A | 8/1990 | Ladner et al. |
| 4,959,455 A | 9/1990 | Clark et al. |
| 4,965,195 A | 10/1990 | Namen et al. |
| 4,968,607 A | 11/1990 | Dower et al. |
| 5,011,912 A | 4/1991 | Hopp et al. |
| 5,260,203 A | 11/1993 | Ladner et al. |
| 5,262,522 A | 11/1993 | Gearing |
| 5,426,048 A | 6/1995 | Gearing |
| 5,457,035 A | 10/1995 | Baum et al. |
| 5,457,038 A | 10/1995 | Trinchieri et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,761 A | 12/1997 | Queen et al. |
| 5,693,762 A | 12/1997 | Queen et al. |
| 5,770,429 A | 6/1998 | Lonberg et al. |
| 5,780,597 A | 7/1998 | Gately et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 6,162,963 A | 12/2000 | Kucherlapati et al. |
| 6,180,370 B1 | 1/2001 | Queen et al. |
| 6,255,458 B1 | 7/2001 | Lonberg et al. |
| 6,270,964 B1 | 8/2001 | Michnick et al. |
| 6,300,129 B1 | 10/2001 | Lonberg et al. |
| 6,495,667 B1 | 12/2002 | Bazan |
| 6,673,986 B1 | 1/2004 | Kucherlapati et al. |
| 6,713,610 B1 | 3/2004 | Kucherlapati et al. |
| 6,914,128 B1 | 7/2005 | Salfeld et al. |
| 7,090,847 B1 | 8/2006 | Oppmann et al. |
| 7,247,711 B2 | 7/2007 | Benson et al. |
| 7,282,204 B2 | 10/2007 | Oft et al. |

(Continued)

FOREIGN PATENT DOCUMENTS

| | | |
|---|---|---|
| EP | 0367566 A1 | 5/1990 |
| EP | 0460846 A1 | 12/1991 |

(Continued)

OTHER PUBLICATIONS

Lederman et al (1991), Molecular Immunology, vol. 28, No. 11, pp. 1171-1181.*
Li et al. (2004), International Immunology, vol. 4, pp. 693-708.*
Panka et al. Proc. Natl. Acad. Sci. USA vol. 85, pp. 3080-3084 (May 1988).*
Rudikoff et al. Proc. Natl. Acad. Sci. USA vol. 79, pp. 1979-1983 (Mar. 1982).*
Amit et al. Science, Vot. 233, pp. 747-753, (Aug. 1986).*
Beyer et al (2008), Journal of Molecular Biology, vol. 382, No. 4, pp. 942-955.*
Adams et al., "The c-myc oncogene driven by immunoglobulin enhancers induces lymphoid malignancy in transgenic mice", Nature, 318:533-538 (1985).

(Continued)

*Primary Examiner* — Prema Mertz
(74) *Attorney, Agent, or Firm* — Marshall, Gerstein & Borun LLP

(57) ABSTRACT

Antigen binding proteins that bind to human IL-23 protein are provided. Nucleic acids encoding the antigen binding protein, vectors, and cells encoding the same as well as use of IL-23 antigen binding proteins for diagnostic and therapeutic purposes are also provided.

6 Claims, 2 Drawing Sheets

(56) References Cited

U.S. PATENT DOCUMENTS

| | | | |
|---|---|---|---|
| 7,491,391 B2 | 2/2009 | Benson et al. |
| 7,501,247 B2 | 3/2009 | Kastelein et al. |
| 7,504,485 B2 | 3/2009 | Salfeld et al. |
| 7,510,709 B2 | 3/2009 | Gurney |
| 7,575,741 B2 | 8/2009 | Bowman et al. |
| 7,608,690 B2 | 10/2009 | Bazan |
| 7,700,739 B2 | 4/2010 | Lacy et al. |
| 7,740,848 B2 | 6/2010 | Kastelein et al. |
| 7,750,126 B2 | 7/2010 | Hirata |
| 7,790,862 B2 | 9/2010 | Lewis et al. |
| 7,807,160 B2 | 10/2010 | Presta et al. |
| 7,807,414 B2 | 10/2010 | Benson et al. |
| 7,872,102 B2 | 1/2011 | Beidler et al. |
| 7,883,704 B2 | 2/2011 | Salfeld et al. |
| 7,893,215 B2 | 2/2011 | Bowman et al. |
| 7,910,703 B2 | 3/2011 | Lewis et al. |
| 7,935,344 B2 | 5/2011 | Benson et al. |
| 7,993,645 B2 | 8/2011 | Benson et al. |
| 8,080,247 B2 | 12/2011 | Giles-Komar et al. |
| 8,106,177 B2 | 1/2012 | Benson et al. |
| 8,110,187 B2 | 2/2012 | Gately et al. |
| 8,182,810 B2 | 5/2012 | Bazan |
| 8,221,760 B2 | 7/2012 | Benson et al. |
| 8,227,579 B2 | 7/2012 | Lewis et al. |
| 8,287,869 B2 | 10/2012 | Gurney |
| 8,293,883 B2 | 10/2012 | Presta |
| 8,329,170 B2 | 12/2012 | Giles-Komar et al. |
| 8,333,968 B2 | 12/2012 | Lewis et al. |
| 8,362,212 B2 | 1/2013 | Presta |
| 8,404,813 B2 | 3/2013 | Presta |
| 2007/0048315 A1* | 3/2007 | Presta |
| 2010/0143357 A1 | 6/2010 | Cua et al. |
| 2011/0177022 A1 | 7/2011 | Oppmann et al. |
| 2011/0262445 A1 | 10/2011 | Clarke et al. |
| 2011/0319292 A1 | 12/2011 | Benson et al. |
| 2012/0027799 A1 | 2/2012 | Sears et al. |
| 2012/0183964 A1 | 7/2012 | Bazan |
| 2012/0276105 A1 | 11/2012 | Kastelein et al. |
| 2012/0308573 A1 | 12/2012 | Benson et al. |
| 2013/0039916 A1 | 2/2013 | Presta et al. |
| 2013/0122009 A1 | 5/2013 | Presta et al. |

FOREIGN PATENT DOCUMENTS

| | | |
|---|---|---|
| EP | 546073 A1 | 6/1993 |
| EP | 546073 B1 | 9/1997 |
| EP | 1210434 B1 | 6/2002 |
| EP | 1002084 B1 | 9/2009 |
| EP | 1072610 B1 | 7/2010 |
| WO | WO-87/05330 A1 | 9/1987 |
| WO | WO-88/01649 A1 | 3/1988 |
| WO | WO-90/04036 A1 | 4/1990 |
| WO | WO-91/10741 A1 | 7/1991 |
| WO | WO-92/03918 A1 | 3/1992 |
| WO | WO-92/22646 A1 | 12/1992 |
| WO | WO-93/01227 A1 | 1/1993 |
| WO | WO-93/10151 A1 | 5/1993 |
| WO | WO-94/02602 A1 | 2/1994 |
| WO | WO-94/10308 A1 | 5/1994 |
| WO | WO-96/33735 A1 | 10/1996 |
| WO | WO-98/24893 A2 | 6/1998 |
| WO | WO-99/05280 A1 | 2/1999 |
| WO | WO-99/10494 A2 | 3/1999 |
| WO | WO-00/09560 A2 | 2/2000 |
| WO | WO-2004/058178 A2 | 7/2004 |
| WO | WO-2004/081190 A2 | 9/2004 |
| WO | WO-2004/101750 A2 | 11/2004 |
| WO | WO-2006/036745 A2 | 4/2006 |
| WO | WO-2006/069036 A2 | 6/2006 |
| WO | WO 2007/005955 * | 1/2007 |
| WO | WO-2007/005955 A2 | 1/2007 |
| WO | WO-2007/024846 A2 | 3/2007 |
| WO | WO-2007/027714 A2 | 3/2007 |
| WO | WO 2007/076524 * | 7/2007 |
| WO | WO-2007/076524 A2 | 7/2007 |
| WO | WO-2007/147019 A2 | 12/2007 |
| WO | WO 2008/103432 * | 8/2008 |
| WO | WO-2008/103432 A1 | 8/2008 |
| WO | WO 2008/103473 * | 8/2008 |
| WO | WO-2008/103473 A1 | 8/2008 |
| WO | WO-2009/043933 A1 | 4/2009 |
| WO | WO-2009/068627 A2 | 6/2009 |
| WO | WO 2009/082624 * | 7/2009 |
| WO | WO-2009/082624 A2 | 7/2009 |
| WO | WO-2010/115786 A1 | 10/2010 |

OTHER PUBLICATIONS

Afzali et al., "The role of T helper 17 (Th17) and regulatory T cells (Treg) in human organ transplantation and autoimmune disease", Clinical and Experimental Immunology, 148:32-46 (2007).

Ahern et al., "The interleukin-23 axis in intestinal inflammation", Immun. Rev., 226:147-159 (2008).

Alexander et al., "Expression of the c-myc Oncogene under control of an immunologulin enhancer in Eμ-myc Transgenic Mice", Mol. Cell. Biol., 7:1436-1444 (1987).

Aplin and Wriston, "Preparation, Properties, and Applications of Carbohydrate Conjugates of Proteins and Lipids", CRC Crit. Rev, Biochem., pp. 259-306 (1981).

Ashkenazi et al., "Protection against endotoxic shock by a tumor necrosis factor receptor immunoadhesin", Proc. Natl. Acad. Sci. USA, 88:10535 (1991).

Baum et al., "Identification of ligands for OX40 receptor", EMBO J., 13:3992-4001 (1994).

Belladonna et al., "IL-23 and IL-12 have overlapping, but distinct, effects on murine dendritic cells", The Journal of Immunology, 168:5448-5454 (2002).

Benoist and Chambon, "In vivo sequence requirements of the SV40 early promoter region", Nature, 290:304-310 (1981).

Beyer, et al., "Crystal Structures of the Pro-Inflammatory Cytokine Interleukin-23 and Its Complex with a High-Affinity Neutralizing Antibody", J Mol Biol, 382(4):942-55 (2008).

Bianchi and McGrew, "High-Level Expression of Full-Length Antibodies Using Trans-Complementing Expression Vectors", Biotech. Biotechnol. Bioeng. 84:439-44 (2003).

Bird et al., "Single-Chain Antigen-Binding Proteins", Science, 242:423 (1988).

Blauvelt, "In this Issue—Full Court Press on Psoriasis", The Journal of Investigative Dermatology, pp. vii-viii (2004).

Bloom et al., "Intrachain disulfide bond in the core hinge region of human IgG4", Protein Science, 6:407 (1997).

Bowie et al., "A method to identify protein sequences that fold into a known three-dimensional structure", Science, 253:164-170 (1991).

Bowman et al., "Rationale and safety of anti-interleukin-23 and anti-interleukin-17A therapy", Current Opinion in Infectious Diseases, 19:245-52 (2006).

Brenner et al., "Population statistics of protein structures: lessons from structural classifications", Curr. Op. Struct. Biol., 7:369-376 (1997).

Brinster et al., "Regulation of metallothionein-thymidine kinase fusion plasmids injected into mouse eggs", Nature, 296:39-42 (1982).

Bruggermann et al., "Designer mice: the production of human antibody repertoires in transgenic animals", Year in Immunol., 7:33-40 (1993).

Brunger, et al., "Crystallography & NMR System: A new software suite for macromolecular structure determination", Acta Crystallogr D Biol Crystallogr, 54(Pt 5): p. 905-21 (1998).

Byrn et al., "Biological properties of a CD4 immunoadhesin", Nature, 344:677 (1990).

Carillo et al., "The Multiple Sequence Alignment Problem in Biology", SIAM J. Applied Math., 48:1073 (1988).

Chen et al., "Anti-IL-23 therapy inhibits multiple inflammatory pathways and ameliorates autoimmune encephalomyelitis", The Journal of Clinical Investigation, 116:1317-1326 (2006).

Chen et al., "Immunoglobulin gene rearrangement in B cell deficient mice generated by targeted deletion of the JH locus", International Immunology, 5:647-656 (1993).

(56) References Cited

OTHER PUBLICATIONS

Cheung, et al., "Epitope-Specific Antibody Response to the Surface Antigen of Duck Hepatitis B Virus in Infected Ducks", Virology, 176:546-552 (1990).
Chothia & Lesk, "Canonical Structures for the Hypervariable Regions of Immunoglobulins", J. Mol. Biol., 196:901-917 (1987).
Chothia et al., "Conformations of immunoglobulin hypervariable regions", Nature, 342:878-883 (1989).
Chou et al., "Conformational Parameters for Amino Acids in Helical, β-Sheet, and Random Coil Regions Calculated from Proteins", Biochemistry, 113:211-222 (1974).
Chou et al., "Empirical Predictions of Proteins Conformation", Ann. Rev. Biochem., 47:251-276 (1979).
Chou et al., "Prediction of β-Turns", Biophys. J., 26:367-384 (1979).
Chou et al., "Prediction of Protein Conformation", Biochem., 13:222-245 (1974).
Chou et al., "Prediction of the secondary structure of proteins from their amino acid sequence", Adv. Enzymol. Relat. Areas Mol. Biol., 47:45-148 (1978).
Cosman et al., "Cloning, sequence and expression of human interleukin-2 receptor", Nature, 312:768 (1984).
Cua et al., "Interleukin-23 rather than Interleukin-12 is the critical cytokine for autoimmune inflammation of the brain", Nature, 421:744-748 (2003).
Dayhoff et al., "A model of evolutionary change in proteins", Atlas of Protein Sequence and Structure, 5:345-352 (1978).
de Graaf et al., "Expression of scFvs and scFv Fusion Proteins in Eukaryotic Cells", Methods Mol Biol., 178:379-387 (2002).
DeBoer et al., "The tac promoter: A functional hybrid derived from the trp and lac promoters", Proc. Natl. Acad. Sci. U.S.A., 80:21-25 (1983).
Devereux et al., "A comprehensive set of sequence analysis programs for the VAX", Nucl. Acid Res., 12:387 (1984).
Duskin et al., "Relationship of the structure and biological activity of the natural homologues of tunicamycin", J. Biol. Chem., 257:3105 (1982).
Edge et al., "Deglycosylation of Glycoproteins by Trifluoromethanesulfonic Acid", Anal. Biochem., 118:131 (1981).
Evans et al., "Design of Nonpeptidal Ligands for a Peptide Receptor: Cholecystokinin Antagonists", J. Med. Chem., 30:1229 (1987).
Fanslow et al., "Structural characteristics of CD40 ligand that determine biological function", Semin. Immunol., 6:267-278 (1994).
Fauchere, "Elements for the Rational Design of Peptide Drugs", Adv. Drug Res., 15:29 (1986).
Fieschi and Casanova, "Mini Review: The role of interleukin-12 in human infectious diseases: only a faint signature", Eur. J. Immunol., 33:1461-4 (2003).
Fishwild et al., "High-avidity human IgGκ monoclonal antibodies from a novel strain of minilocus transgenic mice", Nature Biotechnology, 14:845-85 (1996).
Fredericks et al, "Identification of potent human anti-IL-IRI antagonist antibodies", Protein Engineering, Design & Selection, 17:95-106 (2004).
Ghilardi et al., "Compromised Humoral and Delayed-Type Hypersensitivity Responses in IL-23-Deficient Mice", The Journal of Immunology, 172:2827-2833 (2004).
Gribskov et al., "Profile Analysis", Meth. Enzym., 183:146-159 (1990).
Gribskov et al., "Profile analysis: Detection of distantly related proteins", Proc. Nat. Acad. Sci., 84:4355-4358 (1987).
Grosschedl et al., "Introduction of a μ Immunoglobulin Gene into the Mouse Germ Line: Specific Expression in Lymphoid Cells and Synthesis of Functional Antibody", Cell, 38:647-658 (1984).
Hammer et al., "Diversity of alpha-fetoprotein gene expression in mice is generated by a combination of separate enhancer elements", Science, 253:53-58 (1987).
Hanahan, "Heritable formation of pancreatic β-cell tumours in transgenic mice expressing recombinant insulin/simian virus 40 oncogenes", Nature, 315:115-122 (1985).

Happel et al., "Divergent roles of IL-23 and IL-12 in host defense against *Klebsiella pneumoniae*", The Journal of Experimental Medicine, 202:761-769 (2005).
Harding and Lonberg, "Class Switching in Human Immunoglobulin Transgenic Mice", Ann. N.Y Acad. Sci., 764:536-546 (1995).
Hayden et al., "Single-chain mono- and bispecific antibody derivatives with novel biological properties and antitumour activity from a COS cell transient expression system", Therapeutic Immunology, 1 :3-15 (1994).
Held et al., "Generation of a Protective T-Cell Response Following Coronavirus Infection of the Central Nervous System Is Not Dependent on IL-12/23 Signaling", Viral Immunology, 21:173-187 (2008).
Henikoff et al., "Amino acid substitution matrices from protein blocks", Proc. Natl. Acad. Sci. U.S.A., 89:10915-10919 (1992).
Hillyer et al., "Investigating the role of the interleukin-23/-17A axis in rheumatoid arthritis", Rheumatology, 48:1581-1589 (2009).
Hoeve et al., "Divergent effects of IL-12 and IL-23 on the production of IL-17 by human T cells", Eur. J. Immunol., 36:1-10 (2006).
Holliger et al., "Diabodies": Small bivalent and bispecific antibody fragments, Proc. Natl. Acad. Sci. USA, 90:6444-48 (1993).
Holm et al., "Protein folds and families: sequence and structure alignments", Nucl. Acid. Res., 27:244-247 (1999).
Holtta et al., "IL-23/IL-17 Immunity as a Hallmark of Crohn's Disease", Inflamm Bowel Dis., 14:1175-1184 (2008).
Honegger and Pluckthun, "Yet another numbering scheme for immunoglobulin variable domains: an automatic modeling and analysis tool", J. Mol. Biol., 309(3):657-670 (2001).
Hoogenboom et al., "By-passing Immunisation Human Antibodies from Synthetic Repertoires of Germline VH Gene Segments Rerranged in Vitro", J. Mol. Biol., 227:381 (1991).
Hopp et al., "A Short Polypeptide Marker Sequence Useful for Recombinant Protein Identification and Purification", Bio/Technology, 6:1204 (1988).
Hoppe et al., "A parallel three stranded α-helical bundle at the nucleation site of collagen triple-helix formation", FEBS Letters, 344:191 (1994).
Huston et al., "Protein engineering of antibody binding sites: recovery of specific activity in an anti-digoxin single-chain Fv analogue produced in *Escherichia coli*", Proc. Natl. Acad. Sci. U.S.A., 85:5879 (1988).
Jakobovits et al., "Analysis of homozygous mutant chimeric mice: Deletion of the immunoglobulin heavy-chain joining region blocks B-cell development and antibody production", Proc. Natl. Acad. Sci. USA, 90:2551-2555 (1993).
Jakobovits et al., "Germ-line transmission and expression of a human-derived yeast artificial chromosome", Nature, 362:255-258 (1993).
Jones et al., "Replacing the complementarity-determining regions in a human antibody with those from a mouse", Nature, 321 :522-525 (1986).
Jones, "Progress in protein structure prediction", Curr. Opin. Struct. Biol., 7:377-387 (1997).
Kabat et al., Sequences of Proteins of Immunological Interest, 5th Ed., US Dept. of Health and Human Services, PHS, NIH, NIH Publication No. 91-3242 (1991).
Kastelein, et al., "Discovery and Biology of IL-23 and IL-27: Related but Functionally Distinct Regulators of Inflammation", Annual Review of Immunology, 25:221-42 (2007).
Kelsey et al., "Species- and tissue-specific expression of human α1-antitrypsin in transgenic mice", Genes and Devel., 1 :161-171 (1987).
Khader et al., "IL-23 Compensates for the Absence of IL-12p70 and Is Essential for the IL-17 Response during Tuberculosis but Is Dispensable for Protection and Antigen-Specific IFN-γ Responses if IL-12p70 Is Available", The Journal of Immunology, 175:788-795 (2005).
Kirkland et al., "Analysis of the fine specificity and cross-reactivity of monoclonal anti-lipid A antibodies", J. Immunol., 137:3614-3619 (1986).
Kollias et al., "Regulated Expression of Human Aγ-, β-, and Hybrid γβ-Globin Genes in Transgenic Mice: Manipulation of the Developmental Expression Patterns", Cell, 46:89-94 (1986).

(56) References Cited

OTHER PUBLICATIONS

Korndorfer et al., "Crystallographic Analysis of an "Anticalin" With Tailored Specificity for fluorescein Reveals High Structural Plasticity of the Lipocalin Loop Region", Proteins: Structure, Function, and Bioinformatics, vol. 53, Issue 1:121-129 (2003).
Kortt et ai, "Dimeric and trimeric antibodies: high avidity scFvs for cancer targeting", Biomol. Eng., 18:95-108 (2001).
Kortt et al., "Single-chain Fv fragments of anti-neuraminidase antibody NC10 containing five- and ten-residue linkers form dimers and with zero-residue linker a trimer", Prot. Eng., 10:423 (1997).
Kostelny et al., "Formation of a bispecific antibody by the use of leucine zippers", J. Immunol., 148:1547-1553 (1992).
Kriangkum et al., "Bispecific and bifunctional single chain recombinant antibodies", Biomol. Eng., 18:31-40 (2001).
Krumlauf et al., "Developmental regulation of α-fetoprotein genes in transgenic mice", Mol. Cell. Biol., 5:1639-1648 (1985).
Kurzeja et al., "New Interleukin-23 pathway inhibitors in dermatology", Am. J. Clin. Dermatol., 12:113-125 (2011).
Kyte et al., "A simple method for displaying the hydropathic character of a protein", J. Mol. Biol., 157:105-131 (1982).
Langowski et al., "IL-23 promotes tumour incidence and growth", Nature, 442: 461-5 (2006).
Lantto et al., "Chain Shuffling to modify properties of recombinant immunoglobulins", Methods Mol. Biol., 178:303-316 (2002).
Leder et al., "Consequences of widespread deregulation of the c-myc gene in transgenic mice: multiple neoplasms and normal development", Cell, 45:485-495 (1986).
Lefranc et al, "IMGT unique numbering for immunoglobulin and T cell receptor constant domain and Ig superfamily C-like domains", Dev. Comp. Immunol., 29:185-203 (2005).
Liu, et al., "Interleukin (IL)-23 p19 expression induced by IL-1β in human fibroblast-like synoviocytes with rheumatoid arthritis via active nuclear factor-kB and AP-1 dependent pathway", Rheumatology, 46(8):1266-73 (2007).
Lonberg and Huszar, "Human Antibodies from Transgenic Mice", Intern. Rev. Immunol., 13:65-93 (1995).
Lonberg et al., "Antigen-specific human antibodies from mice comprising four distinct genetic modifications", Nature, 368:856-859 (1994).
Lonberg et al., "Fully human antibodies from transgenic mouse and phage display platforms", Current Opinion in Immunology, 20(4):450-459 (2008).
Lonberg, Chapter 3, "Transgenic Approaches to Human Monoclonal Antibodies", Handbook of Exp. Pharmacology, 113:49-101 (1994).
Lupardus and Garcia, "The Structure of Interleukin-23 Reveals the Molecular Basis of p40 subunit sharing with Interleukin-12", J. Mol. Biol., 382:931-941 (2008).
Mabry et al., "Engineering of stable bispecific antibodies targeting IL-17A and IL23", Protein Engineering Design & Selection, 23(3):115-127 (2010).
MacDonald, "Expression of the pancreatic elastase I gene in transgenic mice", Hepatology, 7:425-515 (1987).
Magram et al., "Developmental regulation of a cloned adult β-globin gene in transgenic mice", Nature, 315:338-340 (1985).
Marks et al., "By-Passing Immunization: building high affinity human antibodies by chain shuffling", BioTechnology, 10:779 (1992).
Marks et al., "Human Antibodies from V-gene Libraries Displayed on Phage", J. Mol. Biol., 222:581 (1991).
Mason et al., "The hypogonadal mouse: reproductive functions restored by gene therapy", Science, 234:1372-1378 (1986).
Meeran et al., "Interleukin-12-deficient mice are at greater risk of UV radiation-induced skin tumors and malignant transformation of papillomas to carcinomas", Mol. Cancer Ther., 5: 825-32 (2006).
Mendez et al., "Functional transplant of megabase human immunoglobulin loci recapitulates human antibody response in mice", Nature Genetics, 15:146-156 (1997).
Moldenhauer et al., "Identity of HML-1 antigen on intestinal intraepithelial T cells and of B-ly7 antigen on hairy cell leukaemia", Scand. J. Immunol., 32:77-82 (1990).
Morel et al., "Monoclonal antibodies to bovine serum albumin: affinity and specificity determinations", Molec. Immunol., 25:7-15 (1988).
Morrison et al., "Chimeric human antibody molecules: mouse antigen-binding domains with human constant region domains", Proc. Natl. Acad. Sci. USA, 81:6851-6855 (1985).
Moult, "The current state of the art in protein structure predicton", Curr. Op. in Biotech., 7:422-427 (1996).
Needleman et al., "A general method applicable to the search for similarities in the amino acid sequence of two proteins", J. Mol. Biol., 48:443-453 (1970).
Oppmann et al., "Novel p19 protein engages IL-12p40 to Form a cytokine, IL-23, with biological activities similar as well as distinct from IL-12", Immunity, 13:715-725 (2000).
Ornitz et al., "Elastase I Promoter Directs Expression of Human Growth Hormone and SV40 T Antigen Genes to Pancreatic Acinar Cells in Transgenic Mice", Cold Spring Harbor Symp. Quant. Biol., 50:399-409 (1986).
Parham et al., "A receptor for the heterodimeric cytokine IL-23 is composed of IL-12Rβ1 and a novel cytokine receptor subunit, IL-23R1", J. Immunol., 168:5699-708 (2002).
Pinkert et al., "An albumin enhancer located 10 kb upstream functions along with its promoter to direct efficient, liver-specific expression in transgenic mice", Genes and Devel., 1:268-276 (1987).
Poljak et al., "Production and structure of diabodies", Structure, 2:1121-23 (1994).
Powers et al., "Expression of single-chain Fv-Fc fusions in *Pichia pastoris*", Journal of Immunological Methods, 251:123-135 (2001).
Readhead et al., "Expression of a myelin basic protein gene in transgenic shiverer mice: correction of the dysmyelinating phenotype", Cell, 48:703-712 (1987).
Riechmann et al., "Reshaping human antibodies for therapy", Nature, 332:323-27 (1988).
Rizo and Gierasch, "Constrained peptides: models of bioactive peptides and protein substructures", Ann. Rev. Biochem., 61:387 (1992).
Roque et al., "Antibodies and genetically engineered related molecules: production and purification", Biotechnol. Prog., 20:639-654 (2004).
Sani, "Tissue-specific expression of rat myosin light-chain 2 gene in transgenic mice", Nature, 314:283-286 (1985).
Shu et al., "Secretion of a single-gene-encoded immunoglobulin from myeloma cells", Proc. Natl. Acad. Sci. USA, 90:7995-7999 (1993).
Sippl et al., "Threading thrills and threats", Structure, 4:15-19 (1996).
Sojar et al., "A chemical method for the deglycosylation of proteins", Arch. Biochem. Biophys., 259:52 (1987).
Songsivilai and Lachmann, "Bispecific antibody: a tool for diagnosis and treatment of disease", Clin. Exp. Immunol., 79:315-321 (1990).
Stahli et al., "Distinction of Epitopes by Monoclonal Antibodies", Methods in Enzymology, 92:242-253 (1983).
Swift et al., "Tissue-Specific Expression of the Rat Pancreatic Elastase / Gene in Transgenic Mice", Cell, 38:639-646 (1984).
Taylor et al., "A transgenic mouse that expresses a diversity of human sequence heavy and light chain immunoglobulins", Nucleic Acids Research, 20:6287-6295 (1992).
Taylor et al., "Human immunoglobulin transgenes undergo rearrangement, somatic mutation and class switching in mice that lack endogenous IgM", International Immunology, 6:579-591 (1994).
"The CCP4 Suite: Programs for Protein Crystallography", Acta Crystallogr D Biol Crystallogr, 50(Pt 5): p. 760-3 (1994).
Thomsen et al., "Promoter-regulatory region of the major immediate early gene of human cytomegalovirus", Proc. Natl. Acad. U.S.A., 81:659-663 (1984).
Thornton et al., "Prediction of progress at last", Nature, 354:105 (1991).
Thotakura et al., "Enzymatic deglycosylation of glycoproteins", Meth. Enzymol., 138:350 (1987).

(56) References Cited

OTHER PUBLICATIONS

Tuaillon et al., "Biased utilization of DHQ52 and JH4 Gene Segments in a Human Ig Transgenic Minilocus is Independent of Antigenic Selection", J. Immunol., 152:2912-2920 (1994).

Veber and Freidinger, "The design of metabolically-stable peptide analogs", TINS, p. 392-396 (1985).

Verhoeyen et al., "Reshaping human antibodies: grafting an antilysozyme activity", Science, 239:1534-1536 (1988).

Villa-Kamaroff et al., "A bacterial clone synthesizing proinsulin", Proc. Natl. Acad. Sci. U.S.A., 75:3727-3731 (1978).

Wagner et al., "Nucleotide sequence of the thymidine kinase gene of herpes simplex virus type 1", Proc. Natl. Acad. Sci. U.S.A., 78:1444-1445 (1981).

Ward et al., "Binding activities of a repertoire of single immunoglobulin variable domains secreted from *Escherichia coli*", Nature, 334:544 (1989).

Yago et al., "IL-23 induces human osteoclastogenesis via IL-17 in vitro, and anti-IL-23 antibody attenuates collagen-induced arthritis in rats", Arthritis Res and Ther., 9(5):R96 (2007).

Yamamoto et al., "Identification of a functional promoter in the long terminal repeat of *Rous sarcoma* virus", Cell, 22:787-797 (1980).

\* cited by examiner

HUMAN IL-23 ANTIGEN BINDING PROTEINS

CROSS-REFERENCE TO RELATED APPLICATIONS

This application is a national stage application under 35 U.S.C. §371 of international Application No. PCT/US2010/054148, having an international filing date of Oct. 26, 2010; which claims priority to U.S. provisional patent application Ser. No. 61/254,982, filed Oct. 26, 2009 and U.S. provisional patent application Ser. No. 61/381,287, filed Sep. 9, 2010, which are incorporated herein by reference.

REFERENCE TO THE SEQUENCE LISTING

The present application is being filed along with a Sequence Listing in electronic format. The Sequence Listing is provided as a file entitled A-1529-US-PCI_Sequence_as_filed_04_25_2012, created Apr. 24, 2012, which is 101 KB in size. The information in the electronic format of the Sequence Listing is incorporated herein by reference in its entirety.

BACKGROUND

Interleukin 23 (IL-23), a heterodimeric cytokine, is a potent inducer of pro-inflammatory cytokines. IL-23 is related to the heterodimeric cytokine Interleukin 12 (IL-12) both sharing a common p40 subunit. In IL-23, a unique p19 subunit is covalently bound to the p40 subunit. In IL-12, the unique subunit is p35 (Oppmann et al., Immunity, 2000, 13: 713-715). The IL-23 heterodimeric protein is secreted. Like IL-12, IL-23 is expressed by antigen presenting cells (such as dendritic cells and macrophages) in response to activation stimuli such as CD40 ligation, Toll-like receptor agonists and pathogens. IL-23 binds a heterodimeric receptor comprising an IL-12Rβ1 subunit (which is shared with the IL-12 receptor) and a unique receptor subunit, IL-23R. The IL-12 receptor consists of IL-12Rβ1 and IL-12Rβ2. IL-23 binds its heterodimeric receptor and signals through JAK2 and Tyk2 to activate STAT1, 3, 4 and 5 (Parham et al., J. Immunol. 2002, 168:5699-708). The subunits of the receptor are predominantly co-expressed on activated or memory T cells and natural killer cells and also at lower levels on dendritic cells, monocytes, macrophages, microglia, keratinocytes and synovial fibroblasts. IL-23 and IL-12 act on different T cell subsets and play substantially different roles in vivo.

IL-23 acts on activated and memory T cells and promotes survival and expansion of the T cell subset, Th17. Th17 cells produce proinflammatory cytokines including IL-6, IL-17, TNFα, IL-22 and GM-CSF. IL-23 also acts on natural killer cells, dendritic cells and macrophages to induce pro-inflammatory cytokine expression. Unlike IL-23, IL-12 induces the differentiation of naïve CD4+ T cells into mature Th1 IFNγ-producing effector cells, and induces NK and cytotoxic T cell function by stimulating IFNγ production. Th1 cells driven by IL-12 were previously thought to be the pathogenic T cell subset in many autoimmune diseases, however, more recent animal studies in models of inflammatory bowel disease, psoriasis, inflammatory arthritis and multiple sclerosis, in which the individual contributions of IL-12 versus IL-23 were evaluated have firmly established that IL-23, not IL-12, is the key driver in autoimmune/inflammatory disease (Ahern et al., Immun. Rev. 2008 226:147-159; Cua et al., Nature 2003 421:744-748; Yago et al., Arthritis Res and Ther. 2007 9(5): R96). It is believed that IL-12 plays a critical role in the development of protective innate and adaptive immune responses to many intracellular pathogens and viruses and in tumor immune surveillance. See Kastelein, et al., Annual Review of Immunology, 2007, 25: 221-42; Liu, et al., Rheumatology, 2007, 46(8): 1266-73; Bowman et al., Current Opinion in Infectious Diseases, 2006 19:245-52; Fieschi and Casanova, Eur. J. Immunol. 2003 33:1461-4; Meeran et al., Mol. Cancer. Ther. 2006 5: 825-32; Langowski et al., Nature 2006 442: 461-5. As such, IL-23 specific inhibition (sparing IL-12 or the shared p40 subunit) should have a potentially superior safety profile compared to dual inhibition of IL-12 and IL-23.

Therefore, use of IL-23 specific antagonists that inhibit human IL-23 (such as antibodies that bind at least the unique p19 subunit or bind both the p19 and p40 subunits of IL-23) that spare IL-12 should provide efficacy equal to or greater than IL-12 antagonists or p40 antagonists without the potential risks associated with inhibition of IL-12. Murine, humanized and phage display antibodies selected for inhibition of recombinant IL-23 have been described; see for example U.S. Pat. No. 7,491,391, WIPO Publications WO1999/05280, WO2007/0244846, WO2007/027714, WO 2007/076524, WO2007/147019, WO2008/103473, WO 2008/103432, WO2009/043933 and WO2009/082624. However, there is a need for fully human therapeutic agents that are able to inhibit native human IL-23. Such therapeutics are highly specific for the target, particularly in vivo. Complete inhibition of the in vivo target can result in lower dose formulations, less frequent and/or more effective dosing which in turn results in reduced cost and increased efficiency. The present invention provides such IL-23 antagonists.

SUMMARY

Antigen binding proteins that bind IL-23, particularly native human IL-23, are provided. The human IL-23 antigen binding proteins can reduce, inhibit, interfere with, and/or modulate at least one of the biological responses related to IL-23, and as such, are useful for ameliorating the effects of IL-23 related diseases or disorders. IL-23 antigen binding proteins can be used, for example, to reduce, inhibit, interfere with and/or modulate IL-23 signaling, IL-23 activation of Th17 cells, IL-23 activation of NK cells, or inducing production of proinflammatory cytokines.

Also provided are expression systems, including cell lines, for the production of IL-23 antigen binding proteins and methods of diagnosing and treating diseases related to human IL-23.

Some of the antigen binding proteins that bind IL-23 that are provided comprise at least one heavy chain variable region comprising a CDRH1, a CDRH2 and a CDRH3 selected from the group consisting of: a CDRH1 that differs by no more than one amino acid substitution, insertion or deletion from a CDRH1 as shown in TABLE 3; a CDRH2 that differs by no more than three, two or one amino acid substitutions, insertions and/or deletions from a CDRH2 as shown in TABLE 3; a CDRH3 that differs by no more than three, two or one amino acid substitutions, insertions and/or deletions from a CDRH3 as shown in TABLE 3; and comprising at least one light chain variable region comprising a CDRL1, a CDRL2 and a CDRL3 selected from the group consisting of: a CDRL1 that differs by no more than three, two or one amino acid substitutions, insertions and/or deletions from a CDRL1 as shown in TABLE 3; a CDRL2 that differs by no more than one amino acid substitution, insertion or deletion from a CDRL2 as shown in TABLE 3; a CDRL3 that differs by no more than one amino acid substitution, insertion or deletion from a CDRL3 as shown in TABLE 3. In one embodiment is provided isolated antigen binding proteins comprising: a CDRH1 selected from the group consisting of SEQ ID NO: 91, 94, 97, 100, and 103; a CDRH2 selected from the group consisting of SEQ ID NO:92, 95, 98, 101, 104, 107, and 110; a CDRH3 selected from the group consisting of SEQ ID NO: 93, 96, 99, 102, and 105; a CDRL1 selected from the group consisting of SEQ ID NO: 62, 65, 68, 71, and 74; a CDRL2 selected from the group consisting of SEQ ID NO:63, 66, 69, 72, 75, and 78; and a CDRL3 selected from the group consisting of SEQ ID NO:64, 67, 70 and 73. In another embodiment is provided isolated antigen bindings protein of comprising: a CDRH1 selected from the group consisting of SEQ ID NO: 91, 106, 109, 112, and 115; a CDRH2 selected from the group consisting of SEQ ID NO: 113, 116, 118, 120, 121, and 122; a CDRH3 selected from the group consisting of SEQ ID NO: 108, 111, 114, 117, and 119; a CDRL1 selected from the group consisting of SEQ ID NO: 77, 80, 83, 85, 86, 87, 88, 89 and 90; a CDRL2 is SEQ ID NO: 81; and a CDRL3 selected from the group consisting of SEQ ID NO: 76, 79, 82 and 84. In another embodiment is provided an isolated antigen-binding protein of that comprises at least one heavy chain variable region and at least one light chain variable region. In yet another embodiment is provided an isolated antigen-binding protein as described above that comprise at least two heavy chain variable regions and at least two light chain variable regions. In yet another embodiment is provided an isolated antigen binding protein wherein the antigen binding protein is coupled to a labeling group.

Also provided are isolated antigen binding proteins that bind IL-23 selected from the group consisting of a) an antigen binding protein having CDRH1 of SEQ ID NO:129, CDRH2 of SEQ ID NO:132, CDRH3 of SEQ ID NO:136, and CDRL1 of SEQ ID NO:123, CDRL2 of SEQ ID NO:81, and CDRL3 of SEQ ID NO: 76; b) an antigen binding protein having CDRH1 of SEQ ID NO:131, CDRH2 of SEQ ID NO: 134, CDRH3 of SEQ ID NO:137 and CDRL1 of SEQ ID NO:124, CDRL2 of SEQ ID N0126 and CDRL3 of SEQ ID NO:128; c) a) an antigen binding protein having CDRH1 of SEQ ID NO:130, CDRH2 of SEQ ID NO:133, CDRH3 of SEQ ID NO:99 and CDRL1 of SEQ ID NO:68, CDRL2 of SEQ ID NO:69, and CDRL3 of SEQ ID NO:67; and d) an antigen binding protein having CDRH1 SEQ ID NO:91, CDRH2 SEQ ID NO: 135, CDRH3 SEQ ID NO:138 and CDRL1 SEQ ID NO:125, CDRL2 SEQ ID NO:127, and CDRL3 SEQ ID NO:64.

Also provided are isolated antigen binding proteins that bind IL-23 comprising at least one heavy chain variable region and at least one light chain variable region, selected from the group consisting of: a heavy chain variable region comprising amino acid residues 31-35, 50-65 and 99-113 of SEQ ID NO:31; and a light chain variable region comprising amino acid residues 23-36, 52-58 and 91-101 of SEQ ID NO:1; a heavy chain variable region comprising amino acid residues 31-35, 50-65 and 99-110 of SEQ ID NO:34 and heavy chain variable region comprising amino acid residues 31-35, 50-66 and 99-110 of SEQ ID NO:36; and a light chain variable region comprising amino acid residues 23-36, 52-62 and 97-105 of SEQ ID NO:4; a heavy chain variable region comprising amino acid residues 31-35, 50-66 and 99-114 of SEQ ID NO:38; and a light chain variable region comprising amino acid residues 23-34, 50-61 and 94-106 of SEQ ID NO:7; a heavy chain variable region comprising amino acid residues 31-35, 50-66 and 99-114 of SEQ ID NO:40; and a light chain variable region comprising amino acid residues 24-34, 50-56 and 94-106 of SEQ ID NO:9; a heavy chain variable region comprising amino acid residues 31-35, 50-66 and 99-114 of SEQ ID NO:42; and a light chain variable region comprising amino acid residues 23-34, 50-61 and 94-106 of SEQ ID NO:11; a heavy chain variable region comprising amino acid residues 31-35, 50-65 and 98-107 of SEQ ID NO:44; and a light chain variable region comprising amino acid residues 24-34, 50-56 and 89-97 of SEQ ID NO:13; a heavy chain variable region comprising amino acid residues 31-37, 52-67 and 100-109 of SEQ ID NO:46 or SEQ ID NO:153; and a light chain variable region comprising amino acid residues 24-34, 50-56 and 89-97 of SEQ ID N015; a heavy chain variable region comprising amino acid residues 31-37, 52-67 and 100-109 of SEQ ID NO:48; and a light chain variable region comprising amino acid residues 24-34, 50-56 and 89-97 of SEQ ID NO:17; a heavy chain variable region comprising amino acid residues 31-37, 52-67 and 101-109 of SEQ ID NO:50; and a light chain variable region comprising amino acid residues 24-34, 50-56 and 89-97 of SEQ ID NO:19; a heavy chain variable region comprising amino acid residues 31-35, 50-65 and 98-107 of SEQ ID NO: 52; and a light chain variable region comprising amino acid residues 24-34, 50-56 and 98-107 of SEQ ID NO:21; a heavy chain variable region comprising amino acid residues 31-37, 52-67 and 100-109 of SEQ ID NO:54; and a light chain variable region comprising amino acid residues 24-34, 50-56 and 89-97 of SEQ ID NO:23; a heavy chain variable region comprising amino acid residues 31-37, 52-67 and 100-109 of SEQ ID NO:56; and a light chain variable region comprising amino acid residues 24-34, 50-56 and 89-97 of SEQ ID NO:25; and a heavy chain variable region comprising amino acid residues 31-37, 52-57 and 100-109 of SEQ ID NO:58; and a light chain variable region comprising amino acid residues 24-34, 500-56 and 89-97 of SEQ ID NO:27.

Provided herein is an isolated antigen binding protein that binds IL-23 comprising a heavy chain variable region and a light chain variable region, wherein the heavy chain variable region sequence differs by no more than 13, 12, 11, 10, 9, 8, 7, 6, 5, 4, 3, 2 or 1 amino acid substitutions, additions and/or deletions from a heavy chain variable region sequence as shown in TABLE 2; and wherein the light chain variable region sequence differs by no more than 13, 12, 11, 10, 9, 8, 7, 6, 5, 4, 3, 2 or 1 amino acid substitutions, additions and/or deletions from a light chain variable region sequence as shown in TABLE 1.

Also provided is an isolated antigen binding protein that binds IL-23 selected from the group consisting of a) a heavy chain variable region of SEQ ID NO:140 and a light chain variable region of SEQ ID NO: 30; b) a heavy chain variable region of SEQ ID NO:141 and a light chain variable region of SEQ ID NO:61; c) a heavy chain variable region of SEQ ID NO:142 and a light chain variable region of SEQ ID NO:4; and d) a heavy chain variable region of SEQ ID NO:143 and a light chain variable region of SEQ ID NO:139.

Also provided is an isolated antigen binding protein comprising a heavy chain variable region comprising of an amino acid sequence having at least 90%, 95%, 96%, 97%, 98% or 99% sequence identity to SEQ ID NO:31, 34, 36, 38, 40, 42, 44, 46, 48, 50, 52, 54, 56 and 58; and a light chain variable region comprising an amino acid sequence having at least 90% sequence identity to SEQ ID NO: 1, 4, 7, 9, 11, 13, 15, 17, 19, 21, 23, 25 and 27. In another embodiment is an isolated antigen binding protein comprising a heavy chain variable region selected from the group consisting of SEQ ID NO: 44, 46, 48, 50, 52, 54, 56, 58 and 153, and a light chain variable region selected from the group consisting of SEQ ID NO:13, 15, 17, 19, 21, 23, 25, and 27. In yet another embodiment is an isolated antigen binding protein comprising a heavy chain variable region selected from the group consisting of SEQ ID NO: 31, 34, 36, 38, 40 and 42, and a light chain variable region selected from the group consisting of SEQ ID NO: 1, 4, 7, 9 and 11.

Also provided is an isolated antigen binding protein that binds IL-23 comprising a heavy chain variable region and a light chain variable region selected from the group consisting of: a) a heavy chain variable region of SEQ ID NO:31 and a light chain variable region of SEQ ID NO:1; b) a heavy chain variable region of SEQ ID NO:34 or 36 and a light chain variable region of SEQ ID NO:4; c) a heavy chain variable region of SEQ ID NO:38 and a light chain variable region of SEQ ID NO: 7; d) a heavy chain variable region of SEQ ID NO:40 and a light chain variable region of SEQ ID NO:9; e) a heavy chain variable region of SEQ ID NO:42 and a light chain variable region of SEQ ID NO: 11; f) a heavy chain variable region of SEQ ID NO:44 and a light chain variable region of SEQ ID NO:13; g) a heavy chain variable region of SEQ ID NO:46 or SEQ ID NO:153 and a light chain variable region of SEQ ID NO:15; h) a heavy chain variable region of SEQ ID NO:48 and a light chain variable region of SEQ ID NO:17; i) a heavy chain variable region of SEQ ID NO:50 and a light chain variable region of SEQ ID NO: 19; j) a heavy chain variable region of SEQ ID NO:52 and a light chain variable region of SEQ ID NO:21; k) a heavy chain variable region of SEQ ID NO:54 and a light chain variable region of SEQ ID NO:23; l) a heavy chain variable region of SEQ ID NO:56 and a light chain variable region of SEQ ID NO:25; and m) a heavy chain variable region of SEQ ID NO:58 and a light chain variable region of SEQ ID NO:27.

Also provided is an isolated antigen binding protein that binds human IL-23, wherein the covered patch formed when the antigen binding protein is bound to human IL-23 comprises residue contacts 30, 31, 32, 49, 50, 52, 53, 56, 92 and 94 of SEQ ID NO:15, wherein the residue contacts have a difference value of greater than or equal to 10 Å$^2$ as determined by solvent exposed surface area. Within one embodiment the residue contacts comprise residues 31-35, 54, 58-60, 66, and 101-105 of SEQ ID NO:46.

Also provided is an isolated antigen binding protein that binds human IL-23, wherein the covered patch formed when the antigen binding protein is bound to human IL-23 comprises residue contacts 31-34, 51, 52, 55, 68, 93 and 98 of SEQ ID NO:1, wherein the residue contacts have a difference value of greater than or equal to 10 Å$^2$ as determined by solvent exposed surface area. Within one embodiment the residue contacts comprise residues 1, 26, 28, 31, 32, 52, 53, 59, 76, 101, 102 and 104-108 of SEQ ID NO:31.

Also provided is an isolated antigen binding protein that binds human IL-23, wherein when the antigen binding protein is bound to human IL-23, the antigen binding protein is 5 Å or less from residues 32-35, 54, 58-60, 66 and 101-105 of SEQ ID NO:46, as determined by X-ray crystallography. In one embodiment the antigen binding protein is 5 Å or less from residues 31-35, 54, 56, 58-60, 66 and 101-105 of SEQ ID NO:46.

Also provided is an isolated antigen binding protein that binds human IL-23, wherein when the antigen binding protein is bound to human IL-23, the antigen binding protein is 5 Å or less from residues 30-32, 49, 52, 53, 91-94 and 96 of SEQ ID NO:15, as determined by X-ray crystallography. In one embodiment the antigen binding protein is 5 Å or less from residues 30-32, 49, 50, 52, 53, 56, 91-94 and 96 of SEQ ID NO:15.

Also provided is an isolated antigen binding protein that binds human IL-23, wherein when the antigen binding protein is bound to human IL-23, the antigen binding protein is 5 Å or less from residues 26-28, 31, 53, 59, 102 and 104-108 of SEQ ID NO:31, as determined by X-ray crystallography. In one embodiment the antigen binding protein is 5 Å or less from residues 1, 26-28, 30-32, 52, 53, 59, 100, and 102-108 of SEQ ID NO:31.

Also provided is an isolated antigen binding protein that binds human IL-23, wherein when said antigen binding protein is bound to human IL-23, said antigen binding protein is 5 Å or less from residues 31-34, 51, 52, 55, 68 and 93 of SEQ ID NO:1 as determined by X-ray crystallography. In one embodiment the antigen binding protein is 5 Å or less from residues 29, 31-34, 51, 52, 55, 68, 93 and 100 of SEQ ID NO:1.

Also provided is an isolated antigen binding protein as described above, wherein the antigen binding protein is an antibody. In one embodiment is provided an isolated antigen binding protein wherein the antibody is a monoclonal antibody, a recombinant antibody, a human antibody, a humanized antibody, a chimeric antibody, a multispecific antibody, or an antibody fragment thereof. In another embodiment is provided an isolated antigen binding protein wherein the antibody fragment is a Fab fragment, a Fab' fragment, a F(ab')2 fragment, a Fv fragment, a diabody, or a single chain antibody molecule. In yet another embodiment is provided an isolated antigen binding protein wherein the antigen binding protein is a human antibody. In still another embodiment is provided an isolated antigen binding protein wherein the antigen binding protein is a monoclonal antibody. In another embodiment is provided an isolated antigen binding protein wherein the antigen binding protein is of the IgG1-, IgG2- IgG3- or IgG4-type. In yet another embodiment is provided an isolated antigen binding protein wherein the antigen binding protein is of the IgG1- or IgG2-type.

An isolated nucleic acid molecule encoding an antigen binding protein as described above, is also provided. In one embodiment is provided an isolated nucleic acid molecule wherein at least one heavy chain variable region is encoded by an isolated nucleic acid molecule selected from the group consisting of SEQ ID NOs:32, 35, 37, 39, 41, 43, 45, 47, 49, 51, 53, 55, 57, 59 and 152 and at least one light chain variable region is encoded by an isolated nucleic acid molecule selected from the group consisting of SEQ ID NOs:2, 5, 6, 8, 10, 12, 14, 16, 18, 20, 22, 24, 26, and 28. In another embodiment is provided a nucleic acid molecule wherein the nucleic acid molecule is operably linked to a control sequence. In another embodiment is provided a vector comprising a nucleic acid molecule as described above. In yet another embodiment is provided a host cell comprising the nucleic acid molecule as described above. In another embodiment is provided a host cell comprising the vector described above. In yet another embodiment is provided an isolated polynucleotide sufficient for use as a hybridization probe, PCR primer or sequencing primer that is a fragment of the nucleic acid molecule as described above or its complement.

Also provided is a method of making the antigen binding protein as described above, comprising the step of preparing said antigen binding protein from a host cell that secretes said antigen binding protein.

Also provided is an isolated antigen binding protein that binds human IL-23, wherein the covered patch formed when the antigen binding protein is bound to human IL-23 comprises a residue contact within residues 46-58, a residue contact within residues 112-120, and a residue contact within residues 155-163 of the human IL-23p19 subunit as described in SEQ ID NO:145, wherein the residue contact has a difference value greater than or equal to 10 Å$^2$ as determined by solvent exposed surface area. In one embodiment is provided wherein the covered patch formed when the antigen binding protein is bound to human IL-23 comprises one, two, three, four, five, six, seven, eight, nine, ten, eleven, twelve or thirteen residue contacts within residues 46-58, one, two, three, four, five, six, seven, eight, nine or ten residue contacts within residues 112-120, and one, two, three, four, five, six, seven, eight or nine residue contacts within residues 155-163 of the human IL-23p19 subunit as described in SEQ ID NO:145. In another embodiment is provided wherein the covered patch formed when the antigen binding protein binds to human IL-23 comprises a residue contact within residues 121-125 of the human IL-23p40 subunit as described in SEQ ID NO:147. In a related embodiment is wherein the covered patch formed when the antigen binding protein is bound to human IL-23 comprises one, two, three, four or five residue contacts within residues 121-125 of the human IL-23p40 subunit as described in SEQ ID NO:147. Within another embodiment is provided wherein the covered patch formed when the antigen binding protein is bound to human IL-23 comprises residue contacts 46, 47, 49, 50, 53, 112-116, 118, 120, 155, 156, 159, 160, and 163 of SEQ ID NO:145. In another embodiment is provided wherein the covered patch formed when the antigen binding protein is bound to human IL-23 comprises residue contacts 46, 47, 49, 50, 53, 112-118, 120, 155, 156, 159, 160, and 163 of SEQ ID NO:145. Within another embodiment is provided wherein the covered patch formed when the antigen binding protein is bound to human IL-23 comprises residues 46, 47, 49, 50, 53-55, 57, 58, 112-116, 118-120, 155, 156, 159, 160, 162 and 163 of SEQ ID NO:145. In a related embodiment is provided wherein the covered patch formed when the antigen binding protein is bound to human IL-23 comprises residue contact 122 of the human IL-23p40 subunit as described in SEQ ID NO:147. In another related embodiment is provided wherein the covered patch formed when the antigen binding protein is bound to human IL-23 comprises residue contacts 122 and 124 of the human IL-23p40 subunit as described in SEQ ID NO:147. In yet another related embodiment is provided wherein the covered patch formed when the antigen binding protein is bound to human IL-23 comprises residue contact 121-123 and 125 of the human IL-23p40 subunit as described in SEQ ID NO:147. In a further related embodiment is provided wherein the covered patch formed when the antigen binding protein is bound to human IL-23 comprises residue contact 121-123, 125 and 283 of the human IL-23p40 subunit as described in SEQ ID NO:147.

Also provided is an isolated antigen binding protein that binds human IL-23, wherein when said antigen binding protein is bound to human IL-23 said antigen binding protein is 5 Å or less from a residue within residues 46-58, from a residue within residues 112-123, and from a residue within residues 155-163 of the human IL-23p19 subunit as described in SEQ ID NO:145, as determined by X-ray crystallography. In one embodiment, when the antigen binding protein is bound to human IL-23, the antigen binding protein is 5 Å or less from one, two, three, four, five, six, seven, eight, nine, ten, eleven, twelve or thirteen residues within residues 46-58, from one, two, three, four, five, six, seven, eight, nine or ten, residues within residues 112-123, and from one, two, three, four, five, six, seven, eight or nine residues within residues 155-163 of the human IL-23p19 subunit as described in SEQ ID NO:145. Within another embodiment when the antigen binding protein is bound to human IL-23 the antigen binding protein is 5 Å or less from residues 46-50, 113-116, 120, 156, 159, 160 and 163 of SEQ ID NO:145. Within another embodiment when the antigen binding protein is bound to human IL-23, the antigen binding protein is 5 Å or less from residues 46-50, 112-120, 156, 159, 160 and 163 of SEQ ID NO:145. Within a related embodiment when the antigen binding protein is bound to human IL-23, the antigen binding protein is 5 Å or less from residues 46-50, 53, 112-120, 156, 159, 160 and 163 of SEQ ID NO:145. Within another embodiment when the antigen binding protein is bound to human IL-23, the antigen binding protein is 5 Å or less from residues 46-50, 53-55, 58, 113-116, 120, 121, 156, 159, 160, 162 and 163 of SEQ ID NO:145. Within a related embodiment when the antigen binding protein is bound to human IL-23, the antigen binding protein is 5 Å or less from residues 46-51, 53-55, 57, 58, 112-116, 118-121, 123, 155, 156, 159, 160, 162 and 163 of SEQ ID NO:145. Within a further embodiment when the antigen binding protein is bound to human IL-23 the antigen binding protein is 5 Å or less from a residue within residues 121-125, of the human IL-23p40 subunit as described in SEQ ID NO:147, as determined by X-ray crystallography. With a related embodiment when the antigen binding protein is bound to human IL-23, said antigen binding protein is 5 Å or less from residues 122 and 124 of SEQ ID NO:147. Within another embodiment when the antigen binding protein is bound to human IL-23, the antigen binding protein is 5 Å or less from residues 121-123 and 125 of SEQ ID NO:147.

Also provided is an isolated antigen binding protein as described above, wherein the antigen binding protein has at least one property selected from the group consisting of: a) reducing human IL-23 activity; b) reducing production of a proinflammatory cytokine; c) binding to human IL-23 with a KD of $\leq 5\times 10^{-8}$ M; d) having a Koff rate of $\leq 5\times 10^{-6}$ 1/s; and d) having an IC50 of $\leq 400$ pM.

A pharmaceutical composition comprising at least one antigen binding protein as described above and pharmaceutically acceptable excipient is provided. In one embodiment is provided a pharmaceutical composition further comprises a labeling group or an effector group. In yet another embodiment is provided a pharmaceutical composition wherein the labeling group is selected from the group consisting of isotopic labels, magnetic labels, redox active moieties, optical dyes, biotinylated groups and predetermined polypeptide epitopes recognized by a secondary reporter. In yet another embodiment is provided a pharmaceutical composition wherein the effector group is selected from the group consisting of a radioisotope, radionuclide, a toxin, a therapeutic group and a chemotherapeutic group.

Also provided is a method for treating or preventing a condition associated with IL-23 in a patient, comprising administering to a patient in need thereof an effective amount of at least one isolated antigen binding protein as described above. In one embodiment is provided a method of wherein the condition is selected from the group consisting of an inflammatory disorder, a rheumatic disorder, an autoimmune disorder, an oncological disorder and a gastrointestinal disorder. In yet another embodiment is provided a method wherein the condition is selected from the group consisting of multiple sclerosis, rheumatoid arthritis, cancer, psoriasis, inflammatory bowel disease, Crohn's disease, ulcerative colitis, systemic lupus erythematosus, psoriatic arthritis, autoimmune myocarditis; type 1 diabetes and ankylosing spondylitis. In still another embodiment is provided a method wherein the isolated antigen-binding protein is administered alone or as a combination therapy.

Also provided is a method of reducing IL-23 activity in a patient comprising administering an effective amount of at least one antigen binding protein as described above. In one embodiment is provided a method of reducing IL-23 activity, wherein said IL-23 activity is inducing production of a proinflammatory cytokine.

DETAILED DESCRIPTION

Figure 1A:
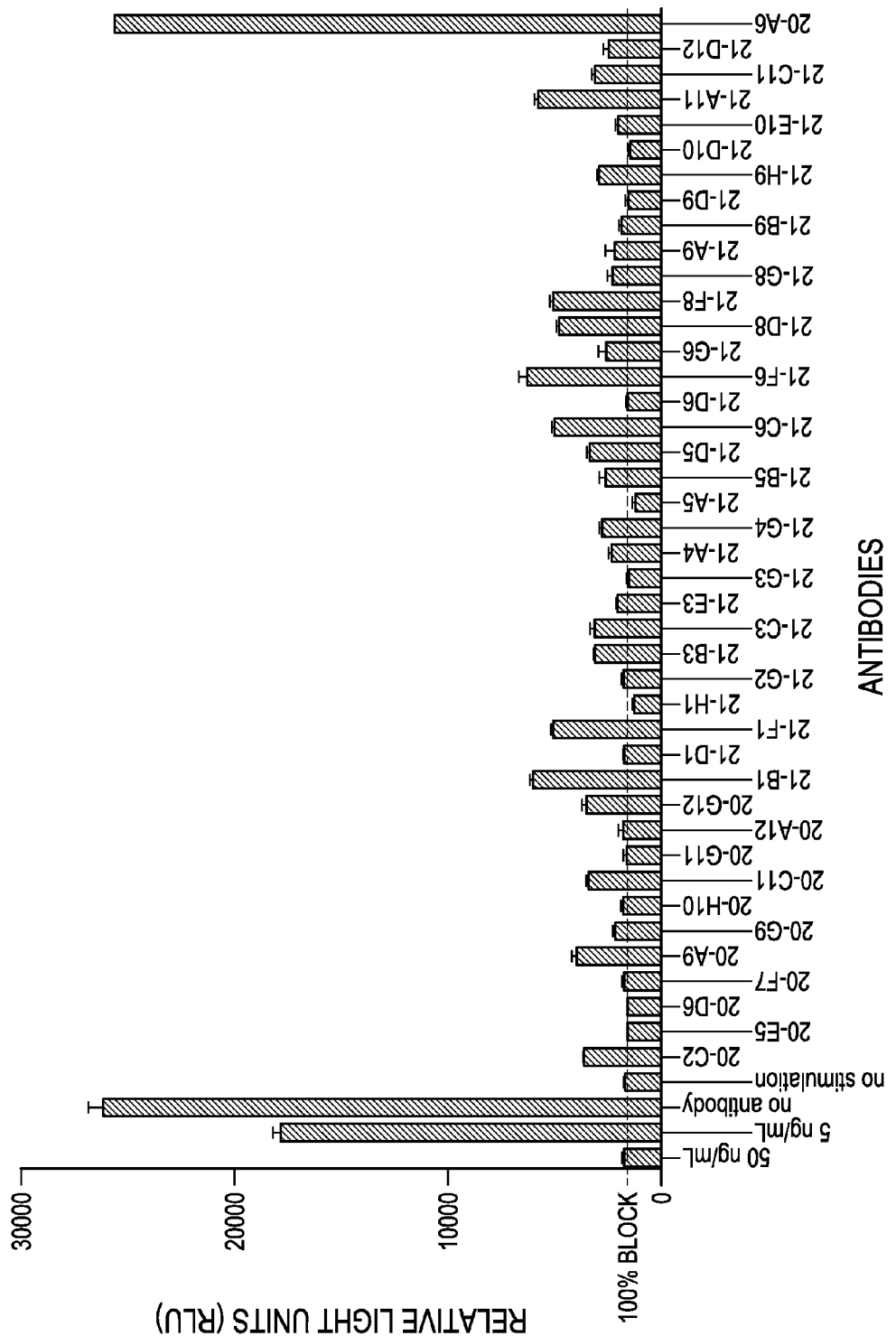
FIG. 1A: Results of STAT-luciferase reporter assay using recombinant human IL-23. All antibodies completely inhibited recombinant human IL-23

The present invention provides compositions, kits, and methods relating to IL-23 antigen binding proteins, including molecules that antagonize IL-23, such as anti-IL-23 antibodies, antibody fragments, and antibody derivatives, e.g., antagonistic anti-IL-23 antibodies, antibody fragments, or antibody derivatives. Also provided are polynucleotides, and derivatives and fragments thereof, comprising a sequence of nucleic acids that encodes all or a portion of a polypeptide that binds to IL-23, e.g., a polynucleotide encoding all or part of an anti-IL-23 antibody, antibody fragment, or antibody derivative, plasmids and vectors comprising such nucleic acids, and cells or cell lines comprising such polynucleotides and/or vectors and plasmids. The provided methods include, for example, methods of making, identifying, or isolating IL-23 antigen binding proteins, such as anti-IL-23 antibodies, methods of determining whether a molecule binds to IL-23, methods of determining whether a molecule antagonizes IL-23, methods of making compositions, such as pharmaceutical compositions, comprising an IL-23 antigen binding protein, and methods for administering an IL-23 antigen binding protein to a subject, for example, methods for treating a condition mediated by IL-23, and for antagonizing a biological activity of IL-23, in vivo or in vitro.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990). Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

All patents and other publications identified are expressly incorporated herein by reference in their entirety for the purpose of describing and disclosing, for example, the methodologies described in such publications that might be used in connection with information described herein.

The polynucleotide and protein sequences of the p19 subunit of human IL-23 (SEQ ID NOs: 144 and 145), the shared p40 subunit (SEQ ID NOs:146 and 147), the human IL-23 receptor hererodimeric subunits IL-12Rβ1 (SEQ ID NOs: 150 and 151) and IL-23R (SEQ ID NOs: 148 and 149), are known in the art, see for example, GenBank Accession Nos. AB030000; M65272, NM_005535, NM_144701, as are those from other mammalian species. Recombinant IL-23 and IL-23 receptor proteins including single chain and Fc proteins as well as cells expressing the IL-23 receptor have been described or are available from commercial sources. (see for example, Oppmann et al., Immunity, 2000, 13: 713-715; R&D Systems, Minneapolis. Minn.; United States Biological, Swampscott, Mass.; WIPO Publication No. WO 2007/076524). Native human IL-23 can be obtained from human cells such as dendritic cells using methods known in the art including those described herein.

IL-23 is a heterodimeric cytokine comprised of a unique p19 subunit that is covalently bound to a shared p40 subunit. The p19 subunit comprises four α-helices, "A", "B", "C" and "D" in an up-up-down-down motif joined by three intra-helix loops between the A and B helices, between the B and C helices and between the C and D helices, see Oppmann et al., Immunity, 2000, 13: 713-715 and Beyer, et al., J Mol Biol, 2008. 382(4): 942-55. The A and D helices of 4 helical bundle cytokines are believed to be involved with receptor binding. The p40 subunit comprises three beta-sheet sandwich domains, D1, D2 and D3 (Lupardus and Garcia, J. Mol. Biol., 2008, 382:931-941.

The term "polynucleotide" includes both single-stranded and double-stranded nucleic acids and includes genomic DNA, RNA, mRNA, cDNA, or synthetic origin or some combination thereof which is not associated with sequences normally found in nature. Isolated polynucleotides comprising specified sequences may include, in addition to the specified sequences, coding sequences for up to ten or even up to twenty other proteins or portions thereof, or may include operably linked regulatory sequences that control expression of the coding region of the recited nucleic acid sequences, and/or may include vector sequences. The nucleotides comprising the polynucleotide can be ribonucleotides or deoxyribonucleotides or a modified form of either type of nucleotide. The modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term "oligonucleotide" means a polynucleotide comprising 100 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a detectable label, such as a radiolabel, a fluorescent label, a hapten or an antigenic label, for detection assays. Oligonucleotides may be used, for example, as PCR primers, cloning primers or hybridization probes.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having one or more deletions from, insertions to, and/or substitutions of the amino acid residues of the native sequence. The term also includes amino acid polymers in which one or more amino acids are chemical analogs of a corresponding naturally-occurring amino acid and polymers. The terms "polypeptide" and "protein" encompass IL-23 antigen binding proteins (such as antibodies) and sequences that have one or more deletions from, additions to, and/or substitutions of the amino acid residues of the antigen binding protein sequence. The term "polypeptide fragment" refers to a polypeptide that has an amino-terminal deletion, a carboxyl-terminal deletion, and/or an internal deletion as compared with the full-length native protein. Such fragments may also contain modified amino acids as compared with the native protein. In certain embodiments, fragments are about five to 500 amino acids long. For example, fragments may be at least 5, 6, 7, 8, 9, 10, 11, 12, 13, 14, 15, 16, 17, 18, 19, 20, 50, 70, 100, 110, 150, 200, 250, 300, 350, 400, or 450 amino acids long. Useful polypeptide fragments include immunologically functional fragments of antibodies, including binding domains. In the case of an IL-23 antigen binding protein, such as an antibody, useful fragments include but are not limited to one or more CDR regions, a variable domain of a heavy or light chain, a portion of an antibody chain, a portion of a variable region including less than three CDRs, and the like.

"Amino acid" includes its normal meaning in the art. The twenty naturally-occurring amino acids and their abbreviations follow conventional usage. See, Immunology—A Synthesis, 2nd Edition, (E. S. Golub and D. R. Gren, eds.), Sinauer Associates: Sunderland, Mass. (1991). Stereoisomers (e.g., D-amino acids) of the twenty conventional amino acids, unnatural amino acids such as [alpha]-, [alpha]-disubstituted amino acids, N-alkyl amino acids, and other unconventional amino acids may also be suitable components for polypeptides. Examples of unconventional amino acids include: 4-hydroxyproline, [gamma]-carboxyglutamate, [epsilon]-N,N,N-trimethyllysine, [epsilon]-N-acetyllysine, O-phosphoserine, N-acetylserine, N-formylmethionine, 3-methylhistidine, 5-hydroxylysine, [sigma]-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

The term "isolated protein" refers to a protein, such as an antigen binding protein (an example of which could be an antibody), that is purified from proteins or polypeptides or other contaminants that would interfere with its therapeutic, diagnostic, prophylactic, research or other use. As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In certain embodiments, an essentially homogeneous substance has been purified to such a degree that contaminating species cannot be detected in the composition by conventional detection methods and thus the composition consists of a single detectable macromolecular species.

A "variant" of a polypeptide (e.g., an antigen binding protein such as an antibody) comprises an amino acid sequence wherein one or more amino acid residues are inserted into, deleted from and/or substituted into the amino acid sequence relative to another polypeptide sequence. Variants include fusion proteins. A "derivative" of a polypeptide is a polypeptide that has been chemically modified in some manner distinct from insertion, deletion, or substitution variants, e.g., via conjugation to another chemical moiety.

The terms "naturally occurring" or "native" as used throughout the specification in connection with biological materials such as polypeptides, nucleic acids, host cells, and the like, refers to materials which are found in nature, such as native human IL-23. In certain aspects, recombinant antigen binding proteins that bind native IL-23 are provided. In this context, a "recombinant protein" is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An antibody as such is a species of an antigen binding protein. Unless otherwise indicated, the term "antibody" includes, in addition to antibodies comprising two full-length heavy chains and two full-length light chains, derivatives, variants, fragments, and muteins thereof, examples of which are described below. An intact antibody generally will comprise at least two full-length heavy chains and two full-length light chains, but in some instances may include fewer chains such as antibodies naturally occurring in camelids which may comprise only heavy chains. Antibodies may be derived solely from a single source, or may be "chimeric," that is, different portions of the antibody may be derived from two different antibodies as described further below. The antigen binding proteins, antibodies, or binding fragments may be produced in hybridomas, by recombinant DNA techniques, or by enzymatic or chemical cleavage of intact antibodies.

The term "functional fragment" (or simply "fragment") of an antibody or immunoglobulin chain (heavy or light chain), as used herein, is an antigen binding protein comprising a portion (regardless of how that portion is obtained or synthesized) of an antibody that lacks at least some of the amino acids present in a full-length chain but which is capable of specifically binding to an antigen. Such fragments are biologically active in that they bind specifically to the target antigen and can compete with other antigen binding proteins, including intact antibodies, for specific binding to a given epitope. In one aspect, such a fragment will retain at least one CDR present in the full-length light or heavy chain, and in some embodiments will comprise a single heavy chain and/or light chain or portion thereof. These biologically active fragments may be produced by recombinant DNA techniques, or may be produced by enzymatic or chemical cleavage of antigen binding proteins, including intact antibodies. Fragments include, but are not limited to, immunologically functional fragments such as Fab, Fab', F(ab')2, Fv, domain antibodies and single-chain antibodies, and may be derived from any mammalian source, including but not limited to human, mouse, rat, camelid or rabbit. It is contemplated further that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

The term "compete" when used in the context of antigen binding proteins (e.g., neutralizing antigen binding proteins or neutralizing antibodies) means competition between antigen binding proteins as determined by an assay in which the antigen binding protein (e.g., antibody or immunologically functional fragment thereof) under test prevents or inhibits specific binding of a reference antigen binding protein (e.g., a ligand, or a reference antibody) to a common antigen (e.g., an IL-23 protein or a fragment thereof). Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, Methods in Enzymology 92:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antigen binding protein and a labeled reference antigen binding protein.

Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Usually, when a competing antigen binding protein is present in excess, it will inhibit specific binding of a reference antigen binding protein to a common antigen by at least 40%, 45%, 50%, 55%, 60%, 65%, 70% or 75%. In some instance, binding is inhibited by at least 80%, 85%, 90%, 91%, 92%, 93%, 94%, 95%, 96%, 97% 98%, 99% or more.

The term "epitope" or "antigenic determinant" refers to a site on an antigen to which an antigen binding protein binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. Epitope determinants may include chemically active surface groupings of molecules such as amino acids, sugar side chains, phosphoryl or sulfonyl groups, and may have specific three dimensional structural characteristics, and/or specific charge characteristics. An epitope typically includes at least 3, 4, 5, 6, 7, 8, 9, 10, 11, 12, 13, 14, 15, 16, 17, 18, 19, 20, 25, 30, 35 amino acids in a unique spatial conformation. Epitopes can be determined using methods known in the art.

IL-23 Antigen Binding Proteins

An "antigen binding protein" as used herein means a protein that specifically binds a specified target antigen; the antigen as provided herein is IL-23, particularly human IL-23, including native human IL-23. Antigen binding proteins as provided herein interact with at least a portion of the unique p19 subunit of IL-23, detectably binding IL-23; but do not bind with any significance to IL-12 (e.g., the p40 and/or the p35 subunits of IL-12), thus "sparing IL-12". As a consequence, the antigen binding proteins provided herein are capable of impacting IL-23 activity without the potential risks that inhibition of IL-12 or the shared p40 subunit might incur. The antigen binding proteins may impact the ability of IL-23 to interact with its receptor, for example by impacting binding to the receptor, such as by interfering with receptor association. In particular, such antigen binding proteins totally or partially reduce, inhibit, interfere with or modulate one or more biological activities of IL-23. Such inhibition or neutralization disrupts a biological response in the presence of the antigen binding protein compared to the response in the absence of the antigen binding protein and can be determined using assays known in the art and described herein. Antigen binding proteins provided herein inhibit IL-23-induced proinflammatory cytokine production, for example IL-23-induced IL-22 production in whole blood cells and IL-23-induced IFNγ expression in NK and whole blood cells. Reduction of biological activity can be about 20%, 30%, 40%, 50%, 60%, 70%, 80%, 85%, 90%, 91%, 92%, 93%, 94%, 95%, 96%, 97% 98%, 99% or more.

An antigen binding protein may comprise a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., Proteins: Structure, Function, and Bioinformatics, (2003) Volume 53, Issue 1:121-129; Roque et al., Biotechnol. Prog., 2004, 20:639-654. In addition, peptide antibody mimetics ("PAMs") can be used, as well as scaffolds based on antibody mimetics utilizing fibronection components as a scaffold.

Certain antigen binding proteins described herein are antibodies or are derived from antibodies. Such antigen binding proteins include, but are not limited to, monoclonal antibodies, bispecific antibodies, minibodies, domain antibodies, synthetic antibodies, antibody mimetics, chimeric antibodies, humanized antibodies, human antibodies, antibody fusions, antibody conjugates, single chain antibodies, and fragments thereof, respectively. In some instances, the antigen binding protein is an immunological fragment of an antibody (e.g., a Fab, a Fab', a F(ab')2, or a scFv). The various structures are further described and defined herein.

Certain antigen binding proteins that are provided may comprise one or more CDRs as described herein (e.g., 1, 2, 3, 4, 5, 6 or more CDRs). In some instances, the antigen binding protein comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or may be completely synthetic in nature. Examples of various polypeptide structures are further described below.

An antigen binding protein of the invention is said to "specifically bind" its target antigen when the dissociation equilibrium constant (KD) is ≤10-8 M. The antigen binding protein specifically binds antigen with "high affinity" when the KD is ≤5×10-9 M, and with "very high affinity" when the KD is ≤5×10-10 M. In one embodiment the antigen binding protein will bind to human IL-23 with a KD of ≤5×10-12 M, and in yet another embodiment it will bind with a KD≤5×10-13 M. In another embodiment of the invention, the antigen binding protein has a KD of ≤5×10-12 M and an Koff of about 5×10-6 1/s. In another embodiment, the Koff is ≤5×10-71/s.

Another aspect provides an antigen binding protein having a half-life of at least one day in vitro or in vivo (e.g., when administered to a human subject). In one embodiment, the antigen binding protein has a half-life of at least three days. In another embodiment, the antibody or portion thereof has a half-life of four days or longer. In another embodiment, the antibody or portion thereof has a half-life of eight days or longer. In another embodiment, the antibody or antigen binding portion thereof is derivatized or modified such that it has a longer half-life as compared to the underivatized or unmodified antibody. In another embodiment, the antigen binding protein contains point mutations to increase serum half life, such as described in WIPO Publication No. WO 00/09560.

In embodiments where the antigen binding protein is used for therapeutic applications, an antigen binding protein can reduce, inhibit, interfere with or modulate one or more biological activities of IL-23, such inducing production of proinflammatory cytokines. IL-23 has many distinct biological effects, which can be measured in many different assays in different cell types; examples of such assays and known and are provided herein.

Some of the antigen binding proteins that are provided have the structure typically associated with naturally occurring antibodies. The structural units of these antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kDa) and one full-length "heavy" chain (in certain embodiments, about 50-70 kDa). Each individual immunoglobulin chain is composed of several "immunoglobulin domains", each consisting of roughly 90 to 110 amino acids and expressing a characteristic folding pattern. These domains are the basic units of which antibody polypeptides are composed. The amino-terminal portion of each chain typically includes a variable region that is responsible for antigen recognition. The carboxy-terminal portion is more conserved evolutionarily than the other end of the chain and is referred to as the "constant region" or "C region". Human light chains generally are classified as kappa and lambda light chains, and each of these contains one variable region and one constant domain (CL1).z Heavy chains are typically classified as mu, delta, gamma, alpha, or epsilon chains, and these define the antibody's isotype as IgM, IgD, IgG, IgA, and IgE, respectively. IgG has several subtypes, including, but not limited to, IgG1, IgG2, IgG3, and IgG4. IgM subtypes include IgM, and IgM2. IgA subtypes include IgA1 and IgA2. In humans, the IgA and IgD isotypes contain four heavy chains and four light chains; the IgG and IgE isotypes contain two heavy chains and two light chains; and the IgM isotype contains five heavy chains and five light chains. The heavy chain constant region (CH) typically comprises one or more domains that may be responsible for effector function. The number of heavy chain constant region domains will depend on the isotype. IgG heavy chains, for example, each contains three CH region domains known as CH1, CH2 and CH3. The antibodies that are provided can have any of these isotypes and subtypes, for example, the IL-23 antigen binding protein is of the IgG1, IgG2, or IgG4 subtype. If an IgG4 is desired, it may also be desired to introduce a point mutation (CPSCP->CPPCP) in the hinge region as described in Bloom et al., 1997, Protein Science 6:407) to alleviate a tendency to form intra-H chain disulfide bonds that can lead to heterogeneity in the IgG4 antibodies. Antibodies provided herein that are of one type can be changed to a different type using subclass switching methods. See, e.g., Lantto et al., 2002, Methods Mol. Biol. 178:303-316.

In full-length light and heavy chains, the variable and constant regions are joined by a "J" region of about twelve or more amino acids, with the heavy chain also including a "D" region of about ten more amino acids. See, e.g., Fundamental Immunology, 2nd ed., Ch. 7 (Paul, W., ed.) 1989, New York: Raven Press. The variable regions of each light/heavy chain pair typically form the antigen binding site.

Variable Regions

Various heavy chain and light chain variable regions (or domains) provided herein are depicted in TABLES 1 and 2. Each of these variable regions may be attached, for example, to heavy and light chain constant regions described above. Further, each of the so generated heavy and light chain sequences may be combined to form a complete antigen binding protein structure.

Provided are antigen binding proteins that contain at least one heavy chain variable region (VH) selected from the group consisting of VH1, VH2, VH3, VH4, VH5, VH6, VH7, VH8, VH9, VH10, VH11, VH12, VH13, VH14, VH15 and VH16 and/or at least one light chain variable region (VL) selected from the group consisting of VL1, VL2, VL3, VL4, VL5, VL6, VL7, VL8, VL9, VL10, VL11, VL12, VL13, VL14, VL15, and VL16 as shown in TABLES 1 and 2 below.

Each of the heavy chain variable regions listed in TABLE 2 may be combined with any of the light chain variable regions shown in TABLE 1 to form an antigen binding protein. In some instances, the antigen binding protein includes at least one heavy chain variable region and/or one light chain variable region from those listed in TABLES 1 and 2. In some instances, the antigen binding protein includes at least two different heavy chain variable regions and/or light chain variable regions from those listed in TABLES 1 and 2. The various combinations of heavy chain variable regions may be combined with any of the various combinations of light chain variable regions.

In other instances, the antigen binding protein contains two identical light chain variable regions and/or two identical heavy chain variable regions. As an example, the antigen binding protein may be an antibody or immunologically functional fragment that comprises two light chain variable regions and two heavy chain variable regions in combinations of pairs of light chain variable regions and pairs of heavy chain variable regions as listed in TABLES 1 and 2. Examples of such antigen binding proteins comprising two identical heavy chain and light chain variable regions include: Antibody A VH14/VL14; Antibody B VH9/VL9; Antibody C VH10/VL10; Antibody D VH15/VL15; Antibody E VH1/VL1, Antibody F VH11/VL11; Antibody G VH12/VL12; Antibody H VH13/VL13; Antibody I VH8/VL8; Antibody J VH3/VL3; Antibody K VH7/VL7; Antibody L VH4/VL4; Antibody M VH5/VL5 and Antibody N VH6/VL6.

Some antigen binding proteins that are provided comprise a heavy chain variable region and/or a light chain variable region comprising a sequence of amino acids that differs from the sequence of a heavy chain variable region and/or a light chain variable region selected from TABLES 1 and 2 at only 1, 2, 3, 4, 5, 6, 7, 8, 9, 10, 11, 12, 13, 14 or 15 amino acid residues, wherein each such sequence difference is independently either a deletion, insertion or substitution of one amino acid. The light and heavy chain variable regions, in some antigen binding proteins, comprise sequences of amino acids that have at least 70%, 75%, 80%, 85%, 90%, 91%, 92%, 93%, 94%, 95%, 96%, 97%, 98% or 99% sequence identity to the amino acid sequences provided in TABLES 1 and 2. Still other antigen binding proteins, e.g., antibodies or immunologically functional fragments, also include variant heavy chain region forms and/or variant light chain region forms as described herein.

The term "identity" refers to a relationship between the sequences of two or more polypeptide molecules or two or more polynucleotides, as determined by aligning and comparing the sequences. "Percent identity" means the percent of identical residues between the amino acids or nucleotides in the compared molecules and is calculated based on the size of the smallest of the molecules being compared.

TABLE 1

Exemplary Variant Light Chain Region Sequences

| | FR1 | CDRL1 | FR2 | CDRL2 |
|---|---|---|---|---|
| $V_L1$ | QSVLTQPPSVSGAPGQRVTISC*TGSSSNTGAGYDVH*WYQQVPGTAPKLLIY*GSGNRPS*GVPD SEQ ID NO: 1 | | | |
| $V_L2$ | QSVLTQPPSVSGAPGQRVTISC*TGSSSNIGAGYDVH*WYQQLPGTAPKLLIY*GSNNRPS*GVPD SEQ ID NO: 3 | | | |
| $V_L3$ | QAVLTQPSSLSASPGASASLTC*TLRSGINVGTYRIY*WYQQKPGSPPQYLLR*YKSDSDKQQGS* SEQ ID NO: 4 | | | |
| $V_L4$ | QAVLTQPSSLSASPGASASLTC*TLRSGINVGTYRIY*WYQQKPGSPPQYLLR*YKSDSDKQQGS* SEQ ID NO: 4 | | | |
| $V_L5$ | QPVLTQPPSASASLGASVTLTC*TLNSGYSDYKVD*WYQQRPGKGPRFVMR*VGTGGIVGSKGD* SEQ ID NO 7 | | | |
| $V_L6$ | QPVLTQPPSASASLGASVTLTC*TLSSGYSDYKVD*WYQQRPGKGPRFVMR*VGTGGIVGSKGE* SEQ ID NO: 9 | | | |
| $V_L7$ | QPELTQPPSASASLGASVTLTC*TLSSGYSDYKVD*WYQLRPGKGPRFVMR*VGTGGTVGSKGE* SEQ ID NO: 11 | | | |
| $V_L8$ | DIQLTPSPSSVSASVGDRVTITC*RASQGIAGWLA*WYQQKPGKAPKLLIY*AASSLQS*GVPSR SEQ ID NO: 13 | | | |
| $V_L9$ | DIQMTQSPSSVSASVGDRVTITC*RASQVISSWLA*WYQQKPGKAPSLLIY*AASSLQS*GVPSR SEQ ID NO: 15 | | | |
| $V_L10$ | DIQMTQSPSSVSASVGDRVTITC*RASQGSSSWFA*WYQQKPGKAPKLLIY*AASSLQS*GVPSR SEQ ID NO: 17 | | | |
| $V_L11$ | DSQMTQSPSSVSASVGDRVTITC*RASQGISSWFA*WYQQKPGQAPNLLIY*AASSLQS*GVPSR SEQ ID NO: 19 | | | |
| $V_L12$ | DIQMTQSPSSVSASVGDRVTITC*RAGQVISSWLA*WYQQKPGKAPKLLIY*AASSLQS*GVPSR SEQ ID NO: 21 | | | |
| $V_L13$ | DIQMTQSPSSVSASVGDRVTITC*RASQGFSGWLA*WYQQKPGKAPKLLIY*AASSLQS*GVPSR SEQ ID NO: 23 | | | |
| $V_L14$ | DIQLTQSPSSVSASVGDRVTITC*RASQVISSWFA*WYQQKPGKAPNLLIY*AASSLQS*GVPSR SEQ ID NO: 25 | | | |
| $V_L15$ | DIQMTQSPSSVSASVGDRVTITC*RASQGSSSWFA*WYQQKPGKAPKLLIY*AASSLQS*GVPSR SEQ ID NO: 27 | | | |
| $V_L16$ | DIQMTQSPSSLSASVGDRVTITC*RASQGIRNDLG*WYQQKPGKAPKRLIY*AASSLQS*GVPSR SEQ ID NO: 29 | | | |

| | FR3 | CDRL3 | FR4 |
|---|---|---|---|
| $V_L1$ | RFSGSKSGTSASLAITGLQAEDEADYYC*QSYDSSLSGWV*FGGGTRLTVL SEQ ID NO: 1 | | |
| $V_L2$ | RFSGSKSGTSASLAITGLQAEDEADYYC*QSYDSSLSGWV*FGGGTKLTVL SEQ ID NO: 3 | | |
| $V_L3$ | GVPSRFSGSKDASANAGILLISGLQSEDEADYYC*MIWHSSASV*FGGGTKLTVL SEQ ID NO: 4 | | |

TABLE 1-continued

Exemplary Variant Light Chain Region Sequences $V_L4$ GVPSRFSGSKDASANAGILLISGLQSEDEADYYC*MIWHSSASV*FGGGTKLTVL
SEQ ID NO: 4

$V_L5$ GIPDRFSVLGSGLNRYLTIKNIQEEDESDYHC*GADHGSGSNFVYV*FGTGTKVTVL
SEQ ID NO 7

$V_L6$ GIPDRFSVLGSGLNRYLTIKNIQEEDESDYHC*GADHGSGSNFVYV*FGTGTKVTVL
SEQ ID NO: 9

$V_L7$ GIPDRFSVLGSGLNRSLTIKNIQEEDESDYHC*GADHGSGSNFVYV*FGTGTKVTVL
SEQ ID NO: 11

$V_L8$ FSGSGSGTDFTLTISSLQPEDFATYYC*QQADSFPPT*FGGGTKVEIK
SEQ ID NO: 13

$V_L9$ FSGSVSGTDFTLTISSLQPEDFATYYC*QQANSFPFT*FGPGTKVDFK
SEQ ID NO: 15

$V_L10$ FSGSGSGTDFTLTISSLQPEDFATYYC*QQANSFPFT*FGPGTKVDIK
SEQ ID NO: 17

$V_L11$ FSGSGSGTEFTLTISSLQPEDFATYYC*QQANSFPFT*FGPGTKVDIK
SEQ ID NO: 19

$V_L12$ FSGSGSGTDFTLTISSLQPDDFATYYC*QQATSFPLT*FGGGTKVEIK
SEQ ID NO: 21

$V_L13$ FSGSGSGTDFTLTISSLQPEDFATYYC*QQATSFPLT*FGPGTKVDIK
SEQ ID NO: 23

$V_L14$ FSGSGSGTDFTLTISSLQPADFATYFC*QQATSFPLT*FGPGTKVDVK
SEQ ID NO: 25

$V_L15$ FSGSGSGTDFTLTISSLQPEDFATYYC*QQANSFPFT*FGPGTKVDIK
SEQ ID NO: 27

$V_L16$ FSGSGSGTEFTLTISSLQPEDFATYYC*LQHNSYPPT*FGQGTKVEIE
SEQ ID NO: 29

TABLE 2

Exemplary Variant Heavy Chain Region Sequences

FR1    CDRH1    FR2    CDRH2

$V_H1$ QVQLVESGGGVVQPGRSLRLSCAASGFTFS*SYGMH*WVRQAPGKGLEWVA*VIWYDGSNEYYADSVKG*
SEQ ID NO: 31

$V_H2$ QVQLVESGGGVVQPGRSLRLSCAASGFTFS*SYGMH*WVRQAPGKGLEWVA*VIWYDGSNKYYADSVKG*
SEQ ID NO: 33

$V_H3$ QVQLVESGGGVVQPGRSLRLSCAASGFTFS*SYGMH*WVRQAPGKGLEWVA*VISFDGSLKYYADSVKG*
SEQ ID NO: 34

$V_H4$ QVQLVESGGGVVQPGRSLRLSCAASGFTFS*SYAMH*WVRQAPGKGLEWLS*VISHDGSIKYYADSVKG*
SEQ ID NO: 36

$V_H5$ EVQLVESGGGLVQPGGSLRLSCAASGFTFS*SYSMN*WVRQAPGKGLEWVS*YISSRSSTIYIADSVKG*
SEQ ID NO: 38

$V_H6$ EVQLVESGGGLVQPGGSLRLSCAASGFTFS*TYSMN*WVRQAPGKGLEWVS*YISSSSSTRYHADSVKG*
SEQ ID NO: 40

$V_H7$ EVQLVESGGGLVQPGGSLRLSCVVSGFTFS*SFSMN*WVRQAPGKGLEWVS*YISSRSSTIYYADSVKG*
SEQ ID NO: 42

$V_H8$ QVQLQESGPGLVKPSETLSLTCTVSGGSIS*TYYWS*WIRQPAGKGLEWIG*LIYTSGSTNYNPSLKS*
SEQ ID NO: 44

$V_H9$ QVQLQESGPGLVKPSQTLSLTCTVSGGSIS*SGGYYWS*WIRQHPGKGLEWIG*HIHYSGNTYYNPSLKS*
SEQ ID NO: 46

$V_H10$ QVQLQESGPGLVKPSQTLSLTCTVSGGSIN*SGGYYWS*WIRQHPGKGLEWIG*YIYYSGSSYYNPSLKS*
SEQ ID NO: 48

TABLE 2-continued

Exemplary Variant Heavy Chain Region Sequences

V_H11 QVQLQESGPGLVKPSQTLSLTCTVSGGSISSGGYYWSWIRQHPGKGLEWIGYIYYSGSTYYNPSLKS
SEQ ID NO: 50

V_H12 QVQLQESGPRLVKPSETLSLTCTVSGDSISSYFWSWIRQPPGKGLEWLGYIYYSGSTNYNPSLKS
SEQ ID NO: 52

V_H13 QVQLQESGPGLVKPSQTLSLTCTVSGGSISSGGYYWTWIRQHPGKGLEWIGYIYYSGNTYYNPSLKS
SEQ ID NO: 54

V_H14 QVQLQESGPGLVKPSQTLSLTCTVSGGSISSGGYYWSWIRQHPGKGLEWIGYIYYSGSTYYNPSLKS
SEQ ID NO: 56

V_H15 QVQLQESGPGLVKPSQTLSLTCTVSGGSINSGGYYWSWIRQHPGKGLEWIGYIYYSGSSYYNPSLKS
SEQ ID NO: 58

V_H16 QVQLVESGGGVVQPGRSLRLSCAASGFTFSSYGMHWVRQAPGKGLEWVALIWYDGSNKYYADSVKG
SEQ ID NO: 60

|  | FR3 | CDRH3 | FR4 |
| --- | --- | --- | --- |

V_H1  RFTISRDNSKNTLYLQMNSLRAEDTAVYYCARDRGYTSSWYPDAFDIWGQGTMVTVSS
SEQ ID NO: 31

V_H2  RFTISRDNSKNTLYLQMNSLRAEDTAVYYCARDRGYSSSWYPDAFDIWGQGTMVTVSS
SEQ ID NO: 33

V_H3  RFTISRDNSKNTLYLQMNSLRAEDTAVYYCARERTTLSGSYFDYWGQGTLVTVSS
SEQ ID NO: 34

V_H4  RFTISRDNSKNTLYLQMNSLRAEDTAVYYCARERTTLSGSYFDYWGQGTLVTVSS
SEQ ID NO: 36

V_H5  RFTISRDNAKNSLYLQMNSLRDEDTAVYYCARRIAAAGGFHYYYALDVWGQGTTVTVSS
SEQ ID NO: 38

V_H6  RFTISRDNAKNSLYLQMNSLRDEDTAVYYCARRIAAAGPWGYYYAMDVWGQGTTVTVSS
SEQ ID NO: 40

V_H7  RFTISRDNAKNSLYLQMNSLRDEDTAVYYCARRIAAAGPWGYYYAMDVWGQGTTVTVSS
SEQ ID NO: 42

V_H8  RVTMSLDTSKNQFSLRLTSVTAADTAVYYCARDRGYYYGVDVWGQGTTVTVSS
SEQ ID NO: 44

V_H9  RVTISVDTSKNQFSLKLSSVTAADTAVYYCAKNRGFYYGMDVWGQGTTVTVSS
SEQ ID NO: 46

V_H10 RVTISVDTSQNQFSLKLSSVTAADTAVYYCARDRGHYYGMDVWGQGTTVTVSS
SEQ ID NO: 48

V_H11 RVTISVDTSKNQFSLKLSSVTAADTAVYYCARDRGHYYGMDVWGQGTTVTVSS
SEQ ID NO: 50

V_H12 RVTISIDTSKNQFSLKLSSVTAADTAVYYCTRDRGSYYGSDYWGQGTLVTVSS
SEQ ID NO: 52

V_H13 RITISVDTSKNQFSLSLSSVTAADTAVYYCARNRGYYYGMDVWGQGTTVTVSS
SEQ ID NO: 54

V_H14 RVTMSVDTSKNQFSLKLSSVTAADTAVYYCAKNRGFYYGMDVWGQGTTVTVSS
SEQ ID NO: 56

V_H15 RVTISVDTSKNQFSLKLSSVTAADTAVYYCARDRGHYYGMDVWGQGTTVTVSS
SEQ ID NO: 58

V_H16 RFTISRDNSKNTLYLQMNSLRAEDTAVYYCARENTVTIYYNYGMDVWGQGTTVTVSS
SEQ ID NO: 60

For these calculations, gaps in alignments (if any) must be addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, *SIAM J. Applied Math.* 48:1073.

In calculating percent identity, the sequences being compared are aligned in a way that gives the largest match between the sequences. The computer program used to determine percent identity is the GCG program package, which includes GAP (Devereux et al., 1984, *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually ¹/₁₀ times the gap opening penalty), as well as a comparison matrix such as PAM 250 or BLOSUM 62 are used in conjunction with the algorithm. In certain embodiments, a standard comparison matrix (see, Dayhoff et al., 1978, *Atlas of Protein Sequence and Structure* 5:345-352 for the PAM 250 comparison matrix; Henikoff et al., 1992, *Proc. Natl. Acad. Sci. U.S.A.* 89:10915-10919 for the BLOSUM 62 comparison matrix) is also used by the algorithm.

Recommended parameters for determining percent identity for polypeptides or nucleotide sequences using the GAP program are the following: Algorithm: Needleman et al., 1970, *J. Mol. Biol.* 48:443-453; Comparison matrix: BLOSUM 62 from Henikoff et al., 1992, supra; Gap Penalty: 12 (but with no penalty for end gaps), Gap Length Penalty: 4, Threshold of Similarity: 0. Certain alignment schemes for aligning two amino acid sequences may result in matching of only a short region of the two sequences and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

The heavy and light chain variable regions disclosed herein include consensus sequences derived from groups of related antigen binding proteins. The amino acid sequences of the heavy and light chain variable regions were analyzed for similarities. Four groups emerged, one group having kappa light chain variable regions, ($V_H9/V_L9$, $V_H10/V_L10$, $V_H11/V_L11$, $V_H13/V_L13$, $V_H14/V_L14$ and $V_H15/V_L15$) and three groups having lambda light chain variable regions: lambda group 1 ($V_H5/V_L5$, $V_H6/V_L6$ and $V_H7/V_L7$), lambda group 2 ($V_H3/V_L3$ and $V_H4/V_L4$), and lambda group 3 ($V_H1/V_L1$ and $V_H2/V_L2$). Light chain germlines represented include VK1/A30 and VK1/L19. Light chain lambda germlines represented include VL1/1e, VL3/3p, VL5/5c and VL9/9a. Heavy chain germlines represented include VH3/3-30, VH3/3-30.3, VH3/3-33, VH3/3-48, VH4/4-31 and VH4/4-59. As used herein, a "consensus sequence" refers to amino acid sequences having conserved amino acids common among a number of sequences and variable amino acids that vary within given amino acid sequences. Consensus sequences may be determined using standard phylogenic analyses of the light and heavy chain variable regions corresponding to the IL-23 antigen binding proteins disclosed herein.

The light chain variable region consensus sequence for the kappa group is DX$_1$QX$_2$TQSPSSVSASV-GDRVTITCRASQGX$_3$X$_4$SX$_5$WX$_6$AWYQQKPGX$_7$AP-X$_8$LLIYAASSLQSGVPSR FS GSX$_9$SGTX$_{10}$FTLTISSLQPX$_{11}$DFATYX$_{12}$CQQANSF-PFTFGPGTKVDX$_{13}$K (SEQ ID NO:30) where X$_1$ is selected from I or S; X$_2$ is selected from M or L; X$_3$ is selected from G or V and X$_4$ is selected from S, F or I; X$_5$ is selected from S or G; X$_6$ is selected from F or L; X$_7$ is selected from K or Q; X$_8$ is selected from K, N or S; X$_9$ is selected from G or V; X$_{10}$ is selected from D or E, X$_{11}$ is selected from E or A; X$_{12}$ is selected from Y or F; and X$_{13}$ is selected from I, V or F.

The light chain variable region consensus sequence for lambda group 1 is QPX$_1$ LTQPPSAS-ASLGASVTLTCTLX$_2$SGYSDYKVDWYQX$_3$RPGKGP-RFVMRVGTGGX$_4$VGSKGX$_5$GI PDRFSVLGSGLNRX$_6$LTIKNIQEEDESDYHCGADH-GSGX$_7$NFVYVFGTGTKVTVL (SEQ ID NO:61) where X$_1$ is selected from V or E; X$_2$ is selected from N or S; X$_3$ is selected from Q or L and X$_4$ is selected from I or T; X$_5$ is selected from D or E; X$_6$ is selected from Y or S; and X$_7$ is selected from S or N.

The light chain variable region consensus sequence for lambda group 3 is QSVLTQPPSV-SGAPGQRVTISCTGSSSNX$_1$GAGYDVHWYQQX$_2$PG-TAPKLLIYGSX$_3$NRPSGVPDRF SG SKSGTSASLAIT-GLQAEDEAD-YYCQSYDSSLSGWVFGGGTX$_4$RLTVL (SEQ ID NO:139) where X$_1$ is selected from T or I; X$_2$ is selected from V or L; X$_3$ is selected from G or N and X$_4$ is selected from R or K.

The heavy chain variable region consensus sequence for the kappa group is QVQLQESG-PGLVKPSQTLSLTCTVSGGSIX$_1$SGGYYWX$_2$WIRQH-PGKGLEWIGX$_3$IX$_4$YSGX$_5$X$_6$YYNP SLK SRX$_7$TX$_8$SVDTSX$_9$NQFSLX$_{10}$LSSVTAADTAVYYC-AX$_{11}$X$_{12}$RGX$_{13}$YYGMDVWGQGTTVTVSS (SEQ ID NO:140) where X$_1$ is selected from N or S; X$_2$ is selected from S or T; X$_3$ is selected from Y or H and X$_4$ is selected from Y or H; X$_5$ is selected from S or N; X$_6$ is selected from S or T; X$_7$ is selected from V or I; X$_8$ is selected from I or M; X$_9$ is selected from K or Q; X$_{10}$ is selected from K or S, X$_{11}$ is selected from R or K; X$_{12}$ is selected from D or N; and X$_{13}$ is selected from H, F or Y.

The heavy chain variable region consensus sequence for lambda group 1 is EVQLVESG-GGLVQPGGSLRLSCX$_1$X$_2$SGFTFSX$_3$X$_4$SMNWVRQA-PGKGLEWVSYISSX$_5$SSTX$_6$YX$_7$AD SV KGRFTISRD-NAKNSLYLQMNSLRDEDTAVYYCA-RRIAAAGX$_8$X$_9$X$_{10}$YYYAX$_{11}$DVWGQGTTVTVSS (SEQ ID NO:141) where X$_1$ is selected from A or V; X$_2$ is selected from A or V; X$_3$ is selected from T or S and X$_4$ is selected from Y or F; X$_5$ is selected from S or R; X$_6$ is selected from R or I; X$_7$ is selected from H, Y or I; X$_8$ is selected from P or G; X$_9$ is selected from W or F; X$_{10}$ is selected from G or H and X$_{11}$ is selected from M or L.

The heavy chain variable region consensus sequence for lambda group 2 is QVQLVESGGGVVQPGRSLRLSCAASGFTFSSYX$_1$MHWVRQAPGKGLEWX$_2$X$_3$-VISX$_4$DGSX$_5$KYYAD SV KGRFTISRDNSKNTLYLQMNSLRAEDTAVYYCARERTTLSG-SYFDYWGQGTLVTVSS (SEQ ID NO:142) where X$_1$ is selected from G or A; X$_2$ is selected from V or L; X$_3$ is selected from A or S and X$_4$ is selected from F or H and X$_5$ is selected from L or I.

The heavy chain variable region consensus sequence for lambda group 3 is QVQLVESGGGVVQPGRSLRLSCAASGFTFSSYGMHWVRQAPGKGLEWVAVIWYDGSNX$_1$YYADSV KG RFTISRDNSKNTLYLQMNSLRAEDTAVYYCARDRG-YX$_2$SSWYPDAFDIWGQGTMVTVSS (SEQ ID NO: 143) where X$_1$ is selected from E or K and X$_2$ is selected from T or S.

Complementarity Determining Regions

Complementarity determining regions or "CDRs" are embedded within a framework in the heavy and light chain variable regions where they constitute the regions responsible for antigen binding and recognition. Variable domains of immunoglobulin chains of the same species, for example, generally exhibit a similar overall structure; comprising relatively conserved framework regions (FR) joined by hypervariable CDR regions. An antigen binding protein can have 1, 2, 3, 4, 5, 6 or more CDRs. The variable regions discussed above, for example, typically comprise three CDRs. The CDRs from heavy chain variable regions and light chain variable regions are typically aligned by the framework regions to form a structure that binds specifically on a target antigen (e.g., IL-23). From N-terminal to C-terminal, naturally-occurring light and heavy chain variable regions both typically conform to the following order of these elements: FR1, CDR1, FR2, CDR2, FR3, CDR3 and FR4. The CDR and FR regions of exemplary light chain variable domains and heavy chain variable domains are highlighted in TABLES 1 and 2. It is recognized that the boundaries of the CDR and FR regions can vary from those highlighted. Numbering systems have been devised for assigning numbers to amino acids that occupy positions in each of these domains. Complementarity determining regions and framework regions of a given antigen binding protein may be identified using these systems. Numbering systems are defined in Kabat et al., Sequences of Proteins of Immunological Interest, 5$^{th}$ Ed., US Dept. of Health and Human Services, PHS, NIH, NIH Publication No. 91-3242, 1991, or Chothia & Lesk, 1987, *J. Mol. Biol.* 196: 901-917; Chothia et al., 1989, *Nature* 342:878-883. Other numbering systems for the amino acids in immunoglobulin chains include IMGT® (the international ImMunoGeneTics information system; Lefranc et al, *Dev. Comp. Immunol.* 2005, 29:185-203); and AHo (Honegger and Pluckthun, *J. Mol. Biol.* 2001, 309(3):657-670). The CDRs provided herein may not only be used to define the antigen binding domain of a traditional antibody structure, but may be embedded in a variety of other polypeptide structures, as described herein.

The antigen binding proteins disclosed herein are polypeptides into which one or more CDRs may be grafted, inserted, embedded and/or joined. An antigen binding protein can have, for example, one heavy chain CDR1 ("CDRH1"), and/or one heavy chain CDR2 ("CDRH2"), and/or one heavy chain CDR3 ("CDRH3"), and/or one light chain CDR1 ("CDRL1"), and/or one light chain CDR2 ("CDRL2"), and/or one light chain CDR3 ("CDRL3"). Some antigen binding proteins include both a CDRH3 and a CDRL3. Specific embodiments generally utilize combinations of CDRs that are non-repetitive, e.g., antigen binding proteins are generally not made with two CDRH2 regions in one variable heavy chain region, etc. Antigen binding proteins may comprise one or more amino acid sequences that are identical to or that differ from to the amino acid sequences of one or more of the CDRs presented in TABLE 3 at only 1, 2, 3, 4, 5, 6, 7, 8, 9, 10, 11, 12, 13, 14 or 15 amino acid residues, wherein each such sequence difference is independently either a deletion, insertion or substitution of one amino acid. The CDRs in some antigen binding proteins comprise sequences of amino acids that have at least 80%, 85%, 90%, 91%, 92, 93%, 94%, 95%, 96%, 97%, 98%, or 99% sequence identity to CDRs sequence listed in TABLE 3. In some antigen binding proteins, the CDRs are embedded into a "framework" region, which orients the CDR(s) such that the proper antigen binding properties of the CDR(s) is achieved.

TABLE 3

Exemplary CDRH and CDRL Sequences

Exemplary CDRL Sequences

| CDRL1 | CDRL2 | CDRL3 |
|---|---|---|
| TGSSSNTGAGYDVH SEQ ID NO: 62 | GSNNRPS SEQ ID NO: 63 | QSYDSSLSGWV SEQ ID NO: 64 |
| TGSSSNIGAGYDVH SEQ ID NO: 65 | GSNNRPS SEQ ID NO: 66 | MIWHSSASV SEQ ID NO: 67 |
| TLRSGINVGTYRIY SEQ ID NO: 68 | YKSDSDKQQGS SEQ ID NO: 69 | GADHGSGSNFVYV SEQ ID NO: 70 |
| TLNSGYSDYKV SEQ ID NO: 71 | VGTGGIVGSKGD SEQ ID NO: 72 | GADHGSGNNFVYV SEQ ID NO: 73 |
| TLSSGYSDYKV SEQ ID NO: 74 | VGTGGIVGSKGE SEQ ID NO: 75 | QQANSFPFT SEQ ID NO: 76 |
| RASQGFSGWLA SEQ ID NO: 77 | VGTGGTVGSKGE SEQ ID NO: 78 | QQATSFPLT SEQ ID NO: 79 |
| RASQVISSWLA SEQ ID NO: 80 | AASSLQS SEQ ID NO: 81 | QQADSFPPT SEQ ID NO: 82 |

TABLE 3-continued

Exemplary CDRH and CDRL Sequences

RASQVISSWFA
SEQ ID NO: 83

LQHNSYPPT
SEQ ID NO: 84

RASQGSSSWFA
SEQ ID NO: 85

RASQGISSWFA
SEQ ID NO: 86

RAGQVISSWLA
SEQ ID NO: 87

RASQGIAGWLA
SEQ ID NO: 88

RASQGIRNDLG
SEQ ID NO: 89

Exemplary CDRH Sequences

| CDRH1 | CDRH2 | CDRH3 |
|---|---|---|
| SYGMH<br>SEQ ID NO: 91 | VIWYDGSNEYYADSVKG<br>SEQ ID NO: 92 | DRGYTSSWYPDAFDI<br>SEQ ID NO: 93 |
| SYAMH<br>SEQ ID NO: 94 | VIWYDGSNKYYADSVKG<br>SEQ ID NO: 95 | DRGYSSSWYPDAFDI<br>SEQ ID NO: 96 |
| TYSMN<br>SEQ ID NO: 97 | VISFDGSLKYYADSVKG<br>SEQ ID NO: 98 | ERTTLSGSYFDY<br>SEQ ID NO: 99 |
| SYSMN<br>SEQ ID NO: 100 | VISHDGSIKYYADSVKG<br>SEQ ID NO: 101 | RIAAAGGFHYYYALDV<br>SEQ ID NO: 102 |
| SFSMN<br>SEQ ID NO: 103 | YISSRSSTIYIADSVKG<br>SEQ ID NO: 104 | RIAAAGPWGYYYAMDV<br>SEQ ID NO: 105 |
| SGGYYWT<br>SEQ ID NO: 106 | YISSSSSTRYHADSVKG<br>SEQ ID NO: 107 | NRGYYYGMDV<br>SEQ ID NO: 108 |
| SGGYYWS<br>SEQ ID NO: 109 | YISSRSSTIYYADSVKG<br>SEQ ID NO: 110 | NRGFYYGMDV<br>SEQ ID NO: 111 |
| SYFWS<br>SEQ ID NO: 112 | YIYYSGNTYYNPSLKS<br>SEQ ID NO: 113 | DRGHYYGMDV<br>SEQ ID NO: 114 |
| TYYWS<br>SEQ ID NO: 115 | HIHYSGNTYYNPSLKS<br>SEQ ID NO: 116 | DRGSYYGSDY<br>SEQ ID NO: 117 |
|  | YIYYSGSTYYNPSLKS<br>SEQ ID NO: 118 | DRGYYYGVDV<br>SEQ ID NO: 119 |
|  | YIYYSGSSYYNPSLKS<br>SEQ ID NO: 120 | ENTVTIYYNYGMDV<br>SEQ ID NO: 6 |
|  | YIYYSGSTNYNPSLKS<br>SEQ ID NO: 121 |  |
|  | LIYTSGSTNYNPSLKS<br>SEQ ID NO: 122 |  |
|  | LIWYDGSNKYYADSVKG<br>SEQ ID NO: 90 |  |

Provided herein are CDR1 regions comprising amino acid residues 23-34 of SEQ ID NOs: 7 and 11; amino acid residues 24-34 of SEQ ID NOs: 9, 13, 15, 17, 19 21, 23, 25, 27 and 29; amino acid residues 23-36 of SEQ ID NOs: 1, 3 and 4; amino acid residues 31-35 of SEQ ID NOs:31, 33, 34, 38, 40, 44, 52 and 60 and amino acid residues 31-37 or SEQ ID NOs: 46, 48, 50, 54, 56 and 58.

CDR2 regions are provided comprising amino acid residues 50-56 of SEQ ID NOs: 9, 13, 15, 17, 19, 21, 23, 25, 27 and 29; amino acid residues 50-61 of SEQ ID NOs: 7 and 11; amino acid residues 52-62 of SEQ ID NO:4; amino acid residues 50-65 of SEQ ID NOs: 31, 33, 44 and 52; amino acid residues 50-66 of SEQ ID NOs: 36, 38, 40, 42 and 60; amino acid residues 52-58 of SEQ ID NOs: 1 and 3 and amino acid residues 52-67 of SEQ ID NOs: 46, 48, 50, 54, 56 and 58.

CDR3 regions comprising amino acid residues 89-97 of SEQ ID NOs: 13, 15, 17, 19, 21, 23, 25, 27 and 29; amino acid residues 91-101 of SEQ ID NOs: 1 and 3; amino acid residues 94-106 of SEQ ID NOs: 7, 9 and 11; amino acid residues 98-107 of SEQ ID NOs: 44 and 52; amino acid residues 97-105 of SEQ ID NO: 4; amino acid residues 99-110 of SEQ ID NOs: 34 and 36; amino acid residues 99-112 of SEQ ID NO: 112; amino acid residues 99-113 of SEQ ID NOs: 31 and 33; amino acid residues 99-114 of SEQ ID NOs: 38, 40 and 42; amino acid residues 100-109 of SEQ ID NOs: 46, 48, 54, 56 and 58; and amino acid residues 101-019 of SEQ ID NO; 50; are also provided.

The CDRs disclosed herein include consensus sequences derived from groups of related sequences. As described previously, four groups of variable region sequences were identified, a kappa group and three lambda groups. The CDRL1 consensus sequence from the kappa group consists of RASQX$_1$X$_2$SX$_3$WX$_4$A (SEQ ID NO:123) where X$_1$ is selected from G or V; X$_2$ is selected from I, F or 5; X$_3$ is selected from S or G and X$_4$ is selected from F or L. The CDRL1 consensus sequence from lambda group 1 consists of TLX$_1$SGYSDYKVD (SEQ ID NO:124) wherein X$_1$ is selected from N or S. The CDRL1 consensus sequences from lambda group 3 consists of TGSSSNX$_1$GAGYDVH (SEQ ID NO:125) wherein X$_1$ is selected from I or T.

The CDRL2 consensus sequence from lambda group 1 consists of VGTGGX$_1$VGSKGX$_2$ (SEQ ID NO: 126) wherein X$_1$ is selected from I or T and X$_2$ is selected from D or E. The CDRL2 consensus sequence from lambda group 3 consists of GSX$_1$NRPS (SEQ ID NO:127) wherein X$_1$ is selected from N or G.

The CDRL3 consensus sequences include GADHGSGX$_1$NFVYV (SEQ IDN NO:128) wherein X$_1$ is S or N.

The CDRH1 consensus sequence from the kappa group consists of SGGYYWX$_1$ (SEQ ID NO:129) wherein X$_1$ is selected from S or T. The CDRH1 consensus sequence from lambda group 1 consists of X$_1$X$_2$SMN (SEQ ID NO:131) wherein X$_1$ is selected from S or T and X$_2$ is selected from Y or F. The CDRH1 consensus sequence from lambda group 2 consists of SYX$_1$ MH (SEQ ID NO:130), wherein X$_1$ is selected from G or A.

The CDRH2 consensus sequence from the kappa group consists of X$_1$ IX$_2$YSGX$_3$X$_4$YYNPSLKS (SEQ ID NO:132) wherein X$_1$ is selected from Y or H; X$_2$ is selected from Y or H; X$_3$ is selected from S or N and X$_4$ is selected from T or S. The consensus sequence from lambda group 1 consists of YISSX$_1$SSTX$_2$YX$_3$ADSVKG (SEQ ID NO:134) wherein X$_1$ is selected from R or S, X$_2$ is selected from I or R, X$_3$ is selected from I, H or Y. The consensus sequence from lambda group 2 consists of VISX$_1$DGSX$_2$KYYADSVKG (SEQ ID NO:133) wherein X$_1$ is F or H and X$_2$ is L or T. The CDRH2 consensus sequence from lambda group 3 consists of VIWYDGSNX$_1$YYADSVKG (SEQ ID NO:135) wherein X$_1$ is selected from K or E.

The CDRH3 consensus sequence from the kappa group consists of X$_1$RGX$_2$YYGMDV (SEQ ID NO:136) wherein X$_1$ is selected from N or D and X$_2$ is selected from H, Y or F. The CDRH3 consensus sequence from lambda group 1 consists of RIAAAGX$_1$X$_2$X$_3$YYYAX$_4$DV (SEQ ID NO:137) wherein X$_1$ is selected from G or P; X$_2$ is selected from F or W; X$_3$ is selected from H or G and X$_4$ is selected from L and M. The CDRH3 consensus sequence from lambda group 3 consists of DRGYX$_1$SSWYPDAFDI (SEQ ID NO:138) wherein X$_1$ is selected from S or T.

Monoclonal Antibodies

The antigen binding proteins that are provided include monoclonal antibodies that bind to IL-23. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a transgenic animal having human immunoglobulin sequences) with an IL-23 immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds an IL-23 polypeptide while sparing IL-12. Such hybridoma cell lines, and anti-IL-23 monoclonal antibodies produced by them, are aspects of the present application.

Monoclonal antibodies secreted by a hybridoma cell line can be purified using any technique known in the art. Hybridomas or mAbs may be further screened to identify mAbs with particular properties, such as the ability to inhibit IL-23-induced activity.

Chimeric and Humanized Antibodies

Chimeric and humanized antibodies based upon the foregoing sequences are also provided. Monoclonal antibodies for use as therapeutic agents may be modified in various ways prior to use. One example is a chimeric antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., 1985, Proc. Natl. Acad. Sci. USA 81:6851-6855. CDR grafting is described, for example, in U.S. Pat. Nos. 6,180,370, 5,693,762, 5,693,761, 5,585,089, and 5,530, 101.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. No. 5,585,089, and No. 5,693,762; Jones et al., 1986, Nature 321:522-525; Riechmann et al., 1988, Nature 332:323-27; Verhoeyen et al., 1988, Science 239:1534-1536), In certain embodiments, constant regions from species other than human can be used along with the human variable region(s) to produce hybrid antibodies.

Fully Human Antibodies

Fully human antibodies are also provided. Methods are available for making fully human antibodies specific for a given antigen without exposing human beings to the antigen ("fully human antibodies"). One specific means provided for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derivatized mAbs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits et al., 1993, *Proc. Natl. Acad. Sci. USA* 90:2551-2555; Jakobovits et al., 1993, *Nature* 362:255-258; and Bruggermann et al., 1993, *Year in Immunol.* 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WIPO patent publications WO96/33735 and WO94/02602. Additional methods relating to transgenic mice for making human antibodies are described in U.S. Pat. Nos. 5,545,807; 6,713,610; 6,673,986; 6,162,963; 5,545,807; 6,300,129; 6,255,458; 5,877,397; 5,874,299 and 5,545,806; in WIPO patent publications WO91/10741, WO90/04036, and in EP 546073B1 and EP 546073A1.

The transgenic mice described above contain a human immunoglobulin gene minilocus that encodes unrearranged human heavy ([mu] and [gamma]) and [kappa] light chain immunoglobulin sequences, together with targeted mutations that inactivate the endogenous [mu] and [kappa] chain loci (Lonberg et al., 1994, *Nature* 368:856-859). Accordingly, the mice exhibit reduced expression of mouse IgM or [kappa] and in response to immunization, and the introduced human heavy and light chain transgenes undergo class switching and somatic mutation to generate high affinity human IgG [kappa] monoclonal antibodies (Lonberg et al., supra.; Lonberg and Huszar, 1995, *Intern. Rev. Immunol.* 13: 65-93; Harding and Lonberg, 1995, *Ann. N.Y Acad. Sci.* 764:536-546). The preparation of such mice is described in detail in Taylor et al., 1992, *Nucleic Acids Research* 20:6287-6295; Chen et al., 1993, *International Immunology* 5:647-656; Tuaillon et al., 1994, *J. Immunol.* 152:2912-2920; Lonberg et al., 1994, *Nature* 368:856-859; Lonberg, 199, *Handbook of Exp. Pharmacology* 113:49-101; Taylor et al., 1994, *International Immunology* 6:579-591; Lonberg and Huszar, 1995, *Intern. Rev. Immunol.* 13:65-93; Harding and Lonberg, 1995, *Ann. N.Y. Acad. Sci.* 764:536-546; Fishwild et al., 1996, *Nature Biotechnology* 14:845-85. See, further U.S. Pat. No. 5,545,806; No. 5,569,825; No. 5,625,126; No. 5,633,425; No. 5,789,650; No. 5,877,397; No. 5,661,016; No. 5,814,318; No. 5,874,299; and No. 5,770,429; as well as U.S. Pat. No. 5,545,807; WIPO Publication Nos. WO 93/1227; WO 92/22646; and WO 92/03918. Technologies utilized for producing human antibodies in these transgenic mice are disclosed also in WIPO Publication No. WO 98/24893, and Mendez et al., 1997, *Nature Genetics* 15:146-156. For example, the HCo7 and HCo12 transgenic mice strains can be used to generate anti-IL-23 antibodies.

Using hybridoma technology, antigen-specific human mAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries (such as disclosed in Hoogenboom et al., 1991, *J. Mol. Biol.* 227:381; Marks et al., 1991, *J. Mol. Biol.* 222:581; WIPO Publication No. WO 99/10494). Phage display techniques mimic immune selection through the display of antibody repertoires on the surface of filamentous bacteriophage, and subsequent selection of phage by their binding to an antigen of choice.

Bispecific or Bifunctional Antigen Binding Proteins

A "bispecific," "dual-specific" or "bifunctional" antigen binding protein or antibody is a hybrid antigen binding protein or antibody, respectively, having two different antigen binding sites, such as one or more CDRs or one or more variable regions as described above. In some instances they are an artificial hybrid antibody having two different heavy/light chain pairs and two different binding sites. Multispecific antigen binding protein or "multispecific antibody" is one that targets more than one antigen or epitope. Bispecific antigen binding proteins and antibodies are a species of multispecific antigen binding protein antibody and may be produced by a variety of methods including, but not limited to, fusion of hybridomas or linking of Fab' fragments. See, e.g., Songsivilai and Lachmann, 1990, *Clin. Exp. Immunol.* 79:315-321; Kostelny et al., 1992, *J. Immunol.* 148:1547-1553.

Immunological Fragments

Antigen binding proteins also include immunological fragments of an antibody (e.g., a Fab, a Fab', a F(ab')$_2$, or a scFv). A "Fab fragment" is comprised one light chain (the light chain variable region ($V_L$) and its corresponding constant domain ($C_L$)) and one heavy chain (the heavy chain variable region ($V_H$) and first constant domain ($C_H1$)). The heavy chain of a Fab molecule cannot form a disulfide bond with another heavy chain molecule. A "Fab' fragment" contains one light chain and a portion of one heavy chain that also contains the region between the $C_H1$ and $C_H2$ domains, such that an interchain disulfide bond can be formed between the two heavy chains of two Fab' fragments to form an F(ab')$_2$ molecule. A "F(ab')$_2$ fragment" thus is composed of two Fab' fragments that are held together by a disulfide bond between the two heavy chains. A "Fv fragment" consists of the variable light chain region and variable heavy chain region of a single arm of an antibody. Single-chain antibodies "scFv" are Fv molecules in which the heavy and light chain variable regions have been connected by a flexible linker to form a single polypeptide chain, which forms an antigen binding region. Single chain antibodies are discussed in detail in WIPO Publication No. WO 88/01649, U.S. Pat. No. 4,946,778 and No. 5,260,203; Bird, 1988, *Science* 242:423; Huston et al., 1988, *Proc. Natl. Acad. Sci. U.S.A.* 85:5879; Ward et al., 1989, *Nature* 334:544, de Graaf et al., 2002, *Methods Mol. Biol.* 178:379-387; Kortt et al., 1997, *Prot. Eng.* 10:423; Kortt et al., 2001, *Biomol. Eng.* 18:95-108 and Kriangkum et al., 2001, *Biomol. Eng.* 18:31-40. A "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

Also included are domain antibodies, immunologically functional immunoglobulin fragments containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens. Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., *Proc. Natl. Acad. Sci. USA* 90:6444-48, 1993 and Poljak et al., *Structure* 2:1121-23, 1994). Similarly, tribodies and tetrabodies are antibodies comprising three and four polypeptide chains, respectively, and forming three and four antigen binding sites, respectively, which can be the same or different. Maxibodies comprise bivalent scFvs covalently attached to the Fc region of IgG1, (see, e.g., Fredericks et al, 2004, *Protein Engineering, Design & Selection*, 17:95-106; Powers et al., 2001, *Journal of Immunological Methods*, 251:123-135; Shu et al., 1993, *Proc. Natl. Acad. Sci. USA* 90:7995-7999; Hayden et al., 1994, *Therapeutic Immunology* 1:3-15).

Various Other Forms

Also provided are variant forms of the antigen binding proteins disclosed above, some of the antigen binding proteins having, for example, one or more conservative amino acid substitutions in one or more of the heavy or light chains, variable regions or CDRs listed in TABLES 1 and 2.

Naturally-occurring amino acids may be divided into classes based on common side chain properties: hydrophobic (norleucine, Met, Ala, Val, Leu, Ile); neutral hydrophilic (Cys, Ser, Thr, Asn, Gln); acidic (Asp, Glu); basic (His, Lys, Arg); residues that influence chain orientation (Gly, Pro); and aromatic (Trp, Tyr, Phe).

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. Such substantial modifications in the functional and/or biochemical characteristics of the antigen binding proteins described herein may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain.

Non-conservative substitutions may involve the exchange of a member of one of the above classes for a member from another class. Such substituted residues may be introduced into regions of the antibody that are homologous with human antibodies, or into the non-homologous regions of the molecule.

In making such changes, according to certain embodiments, the hydropathic index of amino acids may be considered. The hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic profile in conferring interactive biological function on a protein is understood in the art (see, e.g., Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In some aspects, those which are within ±1 are included, and in other aspects, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen binding or immunogenicity, that is, with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in other embodiments, those which are within ±1 are included, and in still other embodiments, those within ±0.5 are included. In some instances, one may also identify epitopes from primary amino acid sequences on the basis of hydrophilicity. These regions are also referred to as "epitopic core regions."

Exemplary conservative amino acid substitutions are set forth in TABLE 4.

TABLE 4

Conservative Amino Acid Substitutions

| Residue | Sub | Residue | Sub | Residue | Sub | Residue | Sub |
|---|---|---|---|---|---|---|---|
| Ala | Ser | Gln | Asn | Leu | Ile, Val | Thr | Ser |
| Arg | Lys | Glu | Asp | Lys | Arg, Gln, Glu | Trp | Tyr |
| Asn | Gln, His | Gly | Pro | Met | Leu, Ile | Tyr | Trp, Phe |

TABLE 4-continued

Conservative Amino Acid Substitutions

| Residue | Sub | Residue | Sub | Residue | Sub | Residue | Sub |
|---|---|---|---|---|---|---|---|
| Asp | Glu | His | Asn, Gln | Phe | Met, Leu, Tyr | Val | Ile, Leu |
| Cys | Ser | Ile | Leu, Val | Ser | Thr | Thr | Ser |

Residue = Original Residue
Sub = Exemplary Substitution

A skilled artisan will be able to determine suitable variants of polypeptides as set forth herein using well-known techniques. One skilled in the art may identify suitable areas of the molecule that may be changed without destroying activity by targeting regions not believed to be important for activity. The skilled artisan also will be able to identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the 3-dimensional structure and amino acid sequence in relation to that structure in similar polypeptides. In view of such information, one skilled in the art may predict the alignment of amino acid residues of an antibody with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using assays for IL-23 activity, (see examples below) thus yielding information regarding which amino acids can be changed and which must not be changed. In other words, based on information gathered from such routine experiments, one skilled in the art can readily determine the amino acid positions where further substitutions should be avoided either alone or in combination with other mutations.

A number of scientific publications have been devoted to the prediction of secondary structure. See, Moult, 1996, *Curr. Op. in Biotech.* 7:422-427; Chou et al., 1974, *Biochem.* 13:222-245; Chou et al., 1974, Biochemistry 113:211-222; Chou et al., 1978, *Adv. Enzymol. Relat. Areas Mol. Biol.* 47:45-148; Chou et al., 1979, *Ann. Rev. Biochem.* 47:251-276; and Chou et al., 1979, *Biophys. J.* 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See, Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-387; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (See, Holm, 1999, supra; and Brenner, 1997, supra).

In some embodiments, amino acid substitutions are made that: (1) reduce susceptibility to proteolysis, (2) reduce susceptibility to oxidation, (3) alter binding affinity for forming protein complexes, (4) alter ligand or antigen binding affinities, and/or (4) confer or modify other physicochemical or functional properties on such polypeptides, such as maintaining the structure of the molecular backbone in the area of the substitution, for example, as a sheet or helical conformation; maintaining or altering the charge or hydrophobicity of the molecule at the target site, or maintaining or altering the bulkiness of a side chain.

For example, single or multiple amino acid substitutions (in certain embodiments, conservative amino acid substitutions) may be made in the naturally-occurring sequence. Substitutions can be made in that portion of the antibody that lies outside the domain(s) forming intermolecular contacts). In such embodiments, conservative amino acid substitutions can be used that do not substantially change the structural characteristics of the parent sequence (e.g., one or more replacement amino acids that do not disrupt the secondary structure that characterizes the parent or native antigen binding protein). Examples of art-recognized polypeptide secondary and tertiary structures are described in Proteins, Structures and Molecular Principles (Creighton, Ed.), 1984, W. H. New York: Freeman and Company; Introduction to Protein Structure (Branden and Tooze, eds.), 1991, New York: Garland Publishing; and Thornton et al., 1991, *Nature* 354:105.

Additional variants include cysteine variants wherein one or more cysteine residues in the parent or native amino acid sequence are deleted from or substituted with another amino acid (e.g., serine). Cysteine variants are useful, inter alia when antibodies (for example) must be refolded into a biologically active conformation. Cysteine variants may have fewer cysteine residues than the native protein, and typically have an even number to minimize interactions resulting from unpaired cysteines.

The heavy and light chain variable region and CDRs that are disclosed can be used to prepare antigen binding proteins that contain an antigen binding region that can specifically bind to an IL-23 polypeptide. "Antigen binding region" means a protein, or a portion of a protein, that specifically binds a specified antigen, such as the region that contains the amino acid residues that interact with an antigen and confer on the antigen binding protein its specificity and affinity for the target antigen. An antigen binding region may include one or more CDRs and certain antigen binding regions also include one or more "framework" regions. For example, one or more of the CDRs listed in TABLE 3 can be incorporated into a molecule (e.g., a polypeptide) covalently or noncovalently to make an immunoadhesion. An immunoadhesion may incorporate the CDR(s) as part of a larger polypeptide chain, may covalently link the CDR(s) to another polypeptide chain, or may incorporate the CDR(s) noncovalently. The CDR(s) enable the immunoadhesion to bind specifically to a particular antigen of interest (e.g., an IL-23 polypeptide).

Other antigen binding proteins include mimetics (e.g., "peptide mimetics" or "peptidomimetics") based upon the variable regions and CDRs that are described herein. These analogs can be peptides, non-peptides or combinations of peptide and non-peptide regions. Fauchere, 1986, *Adv. Drug Res.* 15:29; Veber and Freidinger, 1985, *TINS* p. 392; and Evans et al., 1987, *J. Med. Chem.* 30:1229. Peptide mimetics that are structurally similar to therapeutically useful peptides may be used to produce a similar therapeutic or prophylactic effect. Such compounds are often developed with the aid of computerized molecular modeling. Generally, peptidomimetics are proteins that are structurally similar to an antigen binding protein displaying a desired biological activity, such as the ability to bind IL-23, but peptidomimetics have one or more peptide linkages optionally replaced by a linkage selected from, for example: —$CH_2NH$—, —$CH_2S$—, —$CH_2$—$CH_2$—, —CH=CH-(cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used in certain embodiments to generate more stable proteins. In addition, constrained peptides comprising a consensus sequence or a substantially identical consensus sequence variation may be generated by methods known in the art (Rizo and Gierasch, 1992, *Ann. Rev. Biochem.* 61:387), for example, by adding internal cysteine residues capable of forming intramolecular disulfide bridges which cyclize the peptide.

Derivatives of the antigen binding proteins that are described herein are also provided. The derivatized antigen binding proteins can comprise any molecule or substance that imparts a desired property to the antigen binding protein or fragment, such as increased half-life in a particular use. The derivatized antigen binding protein can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or Streptavidin)), a therapeutic or diagnostic moiety (e.g., a radioactive, cytotoxic, or pharmaceutically active moiety), or a molecule that increases the suitability of the antigen binding protein for a particular use (e.g., administration to a subject, such as a human subject, or other in vivo or in vitro uses). Examples of molecules that can be used to derivatize an antigen binding protein include albumin (e.g., human serum albumin) and polyethylene glycol (PEG). Albumin-linked and PEGylated derivatives of antigen binding proteins can be prepared using techniques well known in the art. In one embodiment, the antigen binding protein is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Other derivatives include covalent or aggregative conjugates of IL-23 antigen binding proteins with other proteins or polypeptides, such as by expression of recombinant fusion proteins comprising heterologous polypeptides fused to the N-terminus or C-terminus of an IL-23 antigen binding protein. For example, the conjugated peptide may be a heterologous signal (or leader) polypeptide, e.g., the yeast alpha-factor leader, or a peptide such as an epitope tag. IL-23 antigen binding protein-containing fusion proteins can comprise peptides added to facilitate purification or identification of the IL-23 antigen binding protein (e.g., poly-His). An IL-23 antigen binding protein also can be linked to the FLAG peptide as described in Hopp et al., 1988, *Bio/Technology* 6:1204; and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers that contain one or more IL-23 antigen binding proteins may be employed as IL-23 antagonists. Oligomers may be in the form of covalently-linked or non-covalently-linked dimers, trimers, or higher oligomers. Oligomers comprising two or more IL-23 antigen binding proteins are contemplated for use, with one example being a homodimer. Other oligomers include heterodimers, homotrimers, heterotrimers, homotetramers, heterotetramers, etc. Oligomers comprising multiple IL-23-binding proteins joined via covalent or non-covalent interactions between peptide moieties fused to the IL-23 antigen binding proteins, are also included. Such peptides may be peptide linkers (spacers), or peptides that have the property of promoting oligomerization. Among the suitable peptide linkers are those described in U.S. Pat. Nos. 4,751,180 and 4,935,233. Leucine zippers and certain polypeptides derived from antibodies are among the peptides that can promote oligomerization of IL-23 antigen binding proteins attached thereto. Examples of leucine zipper domains suitable for producing soluble oligomeric proteins are described in WIPO Publication No. WO 94/10308; Hoppe et al., 1994, *FEBS Letters* 344:191; and Fanslow et al., 1994, *Semin. Immunol.* 6:267-278. In one approach, recombinant fusion proteins comprising an IL-23 antigen binding protein fragment or derivative fused to a leucine zipper peptide are expressed in suitable host cells, and the soluble oligomeric IL-23 antigen binding protein fragments or derivatives that form are recovered from the culture supernatant.

Such oligomers may comprise from two to four IL-23 antigen binding proteins. The IL-23 antigen binding protein moieties of the oligomer may be in any of the forms described above, e.g., variants or fragments. Preferably, the oligomers comprise IL-23 antigen binding proteins that have IL-23 binding activity. Oligomers may be prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in Current Protocols in Immunology, Suppl. 4, pages 10.19.1-10.19.11.

Also included are dimers comprising two fusion proteins created by fusing an IL-23 antigen binding protein to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer. Such Fc polypeptides include native and mutein forms of polypeptides derived from the Fc region of an antibody. Truncated forms of such polypeptides containing the hinge region that promotes dimerization also are included. Fusion proteins comprising Fc moieties (and oligomers formed therefrom)

offer the advantage of facile purification by affinity chromatography over Protein A or Protein G columns. One suitable Fc polypeptide, described in WIPO Publication No. WO 93/10151 and U.S. Pat. Nos. 5,426,048 and 5,262,522, is a single chain polypeptide extending from the N-terminal hinge region to the native C-terminus of the Fc region of a human IgG1 antibody. Another useful Fc polypeptide is the Fc mutein described in U.S. Pat. No. 5,457,035, and in Baum et al., 1994, *EMBO J.* 13:3992-4001. The amino acid sequence of this mutein is identical to that of the native Fc sequence presented in WIPO Publication No. WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

Glycosylation

The antigen binding protein may have a glycosylation pattern that is different or altered from that found in the native species. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antigen binding protein is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence may be altered through changes at the DNA level, particularly by mutating the DNA encoding the target polypeptide at preselected bases such that codons are generated that will translate into the desired amino acids.

Another means of increasing the number of carbohydrate moieties on the antigen binding protein is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in PCT Publication No. WO 87/05330, and in Aplin and Wriston, 1981, *CRC Crit. Rev, Biochem.*, pp. 259-306.

Removal of carbohydrate moieties present on the starting antigen binding protein may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo- and exo-glycosidases as described by Thotakura et al., 1987, *Meth. Enzymol.* 138:350. Glycosylation at potential glycosylation sites may be prevented by the use of the compound tunicamycin as described by Duskin et al., 1982, *J. Biol. Chem.* 257:3105. Tunicamycin blocks the formation of protein-N-glycoside linkages.

Hence, aspects include glycosylation variants of the antigen binding proteins wherein the number and/or type of glycosylation site(s) has been altered compared to the amino acid sequences of the parent polypeptide. In certain embodiments, antigen binding protein variants comprise a greater or a lesser number of N-linked glycosylation sites than the parent polypeptide. Substitutions that eliminate or alter this sequence will prevent addition of an N-linked carbohydrate chain present in the parent polypeptide. For example, the glycosylation can be reduced by the deletion of an Asn or by substituting the Asn with a different amino acid. Antibodies typically have a N-linked glycosylation site in the Fc region.

Labels and Effector Groups

Antigen binding proteins may comprise one or more labels. The term "label" or "labeling group" refers to any detectable label. In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antigen binding protein via spacer arms of various lengths to reduce potential steric hindrance. Various methods for labeling proteins are known in the art. Examples of suitable labeling groups include, but are not limited to, the following: radioisotopes or radionuclides (e.g., $^3H$, $^{14}C$, $^{15}N$, $^{35}S$, $^{90}Y$, $^{99}Tc$, $^{111}In$, $^{125}I$, $^{131}I$), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and may be used as is seen fit.

The term "effector group" means any group coupled to an antigen binding protein that acts as a cytotoxic agent. Examples for suitable effector groups are radioisotopes or radionuclides (e.g., $^3H$, $^{14}C$, $^{15}N$, $^{35}S$, $^{90}Y$, $^{99}Tc$, $^{111}In$, $^{125}I$, $^{131}I$). Other suitable groups include toxins, therapeutic groups, or chemotherapeutic groups. Examples of suitable groups include calicheamicin, auristatins, geldanamycin and maytansine. In some embodiments, the effector group is coupled to the antigen binding protein via spacer arms of various lengths to reduce potential steric hindrance.

Polynucleotides Encoding IL-23 Antigen Binding Proteins

Polynucleotides that encode the antigen binding proteins described herein, or portions thereof, are also provided, including polynucleotides encoding one or both chains of an antibody, or a fragment, derivative, mutein, or variant thereof, polynucleotides encoding heavy chain variable regions or only CDRs, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The polynucleotides can be any length. They can be, for example, 5, 10, 15, 20, 25, 30, 35, 40, 45, 50, 75, 85, 95, 100, 125, 150, 175, 200, 250, 300, 350, 400, 450, 500, 750, 1,000, 1,500, 3,000, 5,000 or more nucleic acids in length, including all values in between, and/or can comprise one or more additional sequences, for example, regulatory sequences, and/or be part of a larger polynucleotide, for example, a vector. The polynucleotides can be single-stranded or double-stranded and can comprise RNA and/or DNA nucleic acids and artificial variants thereof (e.g., peptide nucleic acids).

Polynucleotides encoding certain antigen binding proteins, or portions thereof (e.g., full length antibody, heavy or light chain, variable domain, or a CDRH1, CDRH2, CDRH3, CDRL1, CDRL2, or CDRL3) may be isolated from B-cells of mice that have been immunized with IL-23 or an immunogenic fragment thereof. The polynucleotide may be isolated by conventional procedures such as polymerase chain reaction (PCR). Phage display is another example of a known technique whereby derivatives of antibodies and other antigen binding proteins may be prepared. In one approach, polypeptides that are components of an antigen binding protein of interest are expressed in any suitable recombinant expression system, and the expressed polypeptides are allowed to assemble to form antigen binding protein molecules. Phage display is also used to derive antigen binding proteins having different properties (i.e., varying affinities for the antigen to which they bind) via chain shuffling, see Marks et al., 1992, BioTechnology 10:779.

Due to the degeneracy of the genetic code, each of the polypeptide sequences depicted herein are also encoded by a large number of other polynucleotide sequences besides those provided. For example, heavy chain variable domains provided herein in may be encoded by polynucleotide sequences SEQ ID NOs: 32, 35, 37, 39, 41, 43, 45, 47, 49, 51, 53, 55, 57, or 59. Light chain variable domains may be encoded by polynucleotide sequences SEQ ID NOs: 2, 5, 6, 8, 10, 12, 14, 16, 18, 20, 22, 24, 26, or 28. One of ordinary skill in the art will appreciate that the present application thus provides adequate written description and enablement for each degenerate nucleotide sequence encoding each antigen binding protein.

An aspect further provides polynucleotides that hybridize to other polynucleotide molecules under particular hybridization conditions. Methods for hybridizing nucleic acids, basic parameters affecting the choice of hybridization conditions and guidance for devising suitable conditions are well-known in the art. See, e.g., Sambrook, Fritsch, and Maniatis (2001, Molecular Cloning: A Laboratory Manual, Cold Spring Harbor Laboratory Press, Cold Spring Harbor, N.Y. and Current Protocols in Molecular Biology, 1995, Ausubel et al., eds., John Wiley & Sons, Inc. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that polynucleotides comprising nucleic acid sequences that are at least 65%, 70%, 75%, 80%, 85%, 90%, 91%, 92, 93%, 94%, 95%, 96%, 97%, 98% or 99% identical to each other, including all values in between, typically remain hybridized to each other.

Changes can be introduced by mutation into a polynucleotide, thereby leading to changes in the amino acid sequence of a polypeptide (e.g., an antigen binding protein or antigen binding protein derivative) that it encodes. Mutations can be introduced using any technique known in the art, such as site-directed mutagenesis and random mutagenesis. Mutant polypeptides can be expressed and selected for a desired property. Mutations can be introduced into a polynucleotide without significantly altering the biological activity of a polypeptide that it encodes. For example, substitutions at non-essential amino acid residues. Alternatively, one or more mutations can be introduced into a polynucleotide that selectively change the biological activity of a polypeptide that it encodes. For example, the mutation can quantitatively or qualitatively change the biological activity, such as increasing, reducing or eliminating the activity and changing the antigen specificity of an antigen binding protein.

Another aspect provides polynucleotides that are suitable for use as primers or hybridization probes for the detection of nucleic acid sequences. A polynucleotide can comprise only a portion of a nucleic acid sequence encoding a full-length polypeptide, for example, a fragment that can be used as a probe or primer or a fragment encoding an active portion (e.g., an IL-23 binding portion) of a polypeptide. Probes based on the sequence of a nucleic acid can be used to detect the nucleic acid or similar nucleic acids, for example, transcripts encoding a polypeptide. The probe can comprise a label group, e.g., a radioisotope, a fluorescent compound, an enzyme, or an enzyme co-factor. Such probes can be used to identify a cell that expresses the polypeptide.

Methods of Expressing Antigen Binding Proteins

The antigen binding proteins provided herein may be prepared by any of a number of conventional techniques. For example, IL-23 antigen binding proteins may be produced by recombinant expression systems, using any technique known in the art. See, e.g., Monoclonal Antibodies, Hybridomas: A New Dimension in Biological Analyses, Kennet et al. (eds.) Plenum Press, New York (1980); and Antibodies: A Laboratory Manual, Harlow and Lane (eds.), Cold Spring Harbor Laboratory Press, Cold Spring Harbor, N.Y. (1988).

Expression systems and constructs in the form of plasmids, expression vectors, transcription or expression cassettes that comprise at least one polynucleotide as described above are also provided herein, as well host cells comprising such expression systems or constructs. As used herein, "vector" means any molecule or entity (e.g., nucleic acid, plasmid, bacteriophage or virus) suitable for use to transfer protein coding information into a host cell. Examples of vectors include, but are not limited to, plasmids, viral vectors, non-episomal mammalian vectors and expression vectors, for example, recombinant expression vectors. Expression vectors, such as recombinant expression vectors, are useful for transformation of a host cell and contain nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto. "Operably linked" means that the components to which the term is applied are in a relationship that allows them to carry out their inherent functions. For example, a control sequence, e.g., a promoter, in a vector that is "operably linked" to a protein coding sequence are arranged such that normal activity of the control sequence leads to transcription of the protein coding sequence resulting in recombinant expression of the encoded protein.

Another aspect provides host cells into which an expression vector, such as a recombinant expression vector, has been introduced. A host cell can be any prokaryotic cell (for example, E. coli) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced polynucleotide can be identified by drug selection (e.g., cells that have incorporated the selectable marker gene will survive, while the other cells die), among other methods.

Antigen binding proteins can be expressed in hybridoma cell lines (e.g., in particular antibodies may be expressed in hybridomas) or in cell lines other than hybridomas. Expression constructs encoding the antigen binding proteins can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. Nos. 4,399,216; 4,912,040; 4,740,461; 4,959,455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs typically comprise a polynucleotide encoding a polypeptide. The polypeptide may comprise one or more of the following: one or more CDRs such as provided herein; a light chain variable region; a heavy chain variable region; a light chain constant region; a heavy chain constant region (e.g., $C_H1$, $C_H2$ and/or $C_H3$); and/or another scaffold portion of an IL-23 antigen binding protein. These nucleic acid sequences are inserted into an appropriate expression vector using standard ligation techniques. In one embodiment, the heavy or light chain constant region is appended to the C-terminus of a heavy or light chain variable region provided herein and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964). Suitable expression vectors can be purchased, for example, from Invitrogen Life Technologies (Carlsbad, Calif.) or BD Biosciences (San Jose, Calif.). Other useful vectors for cloning and expressing the antibodies and fragments include those described in Bianchi and McGrew, 2003, *Biotech. Biotechnol. Bioeng.* 84:439-44. Additional suitable expression vectors are discussed, for example, in *Methods Enzymol.*, vol. 185 (D. V. Goeddel, ed.), 1990, New York: Academic Press.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the polynucleotide encoding the polypeptide to be expressed, and a selectable marker element. The expression vectors that are provided may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

Optionally, the vector may contain a "tag"-encoding sequence, i.e., an oligonucleotide molecule located at the 5' or 3' end of the IL-23 antigen binding protein coding sequence; the oligonucleotide sequence encodes polyHis (such as hexaHis), or another "tag" such as FLAG®, HA (hemaglutinin influenza virus), or myc, for which commercially available antibodies exist. This tag is typically fused to the polypeptide upon expression of the polypeptide, and can serve as a means for affinity purification or detection of the IL-23 antigen binding protein from the host cell. Affinity purification can be accomplished, for example, by column chromatography using antibodies against the tag as an affinity matrix. Optionally, the tag can subsequently be removed from the purified IL-23 antigen binding protein by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Qiagen, Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antigen binding protein that binds to IL-23. As a result, increased quantities of a polypeptide such as an antigen binding protein are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or pro-sequences to improve glycosylation or yield. For example, one may alter the peptidase cleavage site of a particular signal peptide, or add prosequences, which also may affect glycosylation. The final protein product may have, in the −1 position (relative to the first amino acid of the mature protein), one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning will typically contain a promoter that is recognized by the host organism and operably linked to the molecule encoding an IL-23 antigen binding protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression. A large number of promoters, recognized by a variety of potential host cells, are well known. A suitable promoter is operably linked to the DNA encoding a heavy chain variable region or a light chain variable region of an IL-23 antigen binding protein by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus, and Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, *Nature* 290:304-310); CMV promoter (Thornsen et al., 1984, *Proc. Natl. Acad. U.S.A.* 81:659-663); the promoter contained in the 3' long terminal repeat of Rous sarcoma virus (Yamamoto et al., 1980, *Cell* 22:787-797); herpes thymidine kinase promoter (Wagner et al., 1981, *Proc. Natl. Acad. Sci. U.S.A.* 78:1444-1445); promoter and regulatory sequences from the metallothionine gene (Prinster et al., 1982, *Nature* 296:39-42); and prokaryotic promoters such as the beta-lactamase promoter (Villa-Kamaroff et al., 1978, *Proc. Natl. Acad. Sci. U.S.A.* 75:3727-3731); or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); the insulin gene control region that is active in pancreatic beta cells (Hanahan, 1985, *Nature* 315:115-122); the immunoglobulin gene control region that is active in lymphoid cells (Grosschedl et al., 1984, *Cell* 38:647-658; Adames et al., 1985, *Nature* 318:533-538; Alexander et al., 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-feto-protein gene control region that is active in liver (Krumlauf et al., 1985, *Mol. Cell. Biol.* 5:1639-1648; Hammer et al., 1987, *Science* 253:53-58); the alpha 1-antitrypsin gene control region that is active in liver (Kelsey et al., 1987, *Genes and Devel.* 1:161-171); the beta-globin gene control region that is active in myeloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314:283-286); and the gonadotropic releasing hormone gene control region that is active in the hypothalamus (Mason et al., 1986, *Science* 234:1372-1378).

An enhancer sequence may be inserted into the vector to increase transcription by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

After the vector has been constructed, the completed vector may be inserted into a suitable host cell for amplification and/or polypeptide expression. The transformation of an expression vector for an antigen binding protein into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., Molecular Cloning: A Laboratory Manual, 3rd ed., Cold Spring Harbor Laboratory Press, Cold Spring Harbor, N.Y. (2001).

A host cell, when cultured under appropriate conditions, synthesizes protein that can be subsequently collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and constitutively produce antigen binding proteins with IL-23 binding properties. In another embodiment, a cell line from the B cell lineage that does not make its own antibody but has a capacity to make and secrete a heterologous antibody can be also selected.

Use of Human IL-23 Antigen Binding Proteins for Diagnostic and Therapeutic Purposes Antigen binding proteins are useful for detecting IL-23 in biological samples and identification of cells or tissues that produce IL-23. Antigen binding proteins that specifically bind to IL-23 may be used in diagnosis and/or treatment of diseases related to IL-23 in a patient in need thereof. For one, the IL-23 antigen binding proteins can be used in diagnostic assays, e.g., binding assays to detect and/or quantify IL-23 expressed in blood, serum, cells or tissue. In addition, IL-23 antigen binding proteins can be used to reduce, inhibit, interfere with or modulate one or more biological activities of IL-23 in a cell or tissue. Thus antigen binding proteins that bind to IL-23 may have therapeutic use in ameliorating diseases related to IL-23.

Indications

The present invention also relates to the use of IL-23 antigen binding proteins for use in the prevention or therapeutic treatment of medical disorders, such as those disclosed herein. The IL-23 antigen binding proteins are useful to treat a variety of conditions in which IL-23 is associated with or plays a role in contributing to the underlying disease or disorder or otherwise contributes to a negative symptom.

Conditions effectively treated by IL-23 antigen binding proteins play a role in the inflammatory response. Such inflammatory disorders include periodontal disease; lung disorders such as asthma; skin disorders such as psoriasis, atopic dermatitis, contact dermatitis; rheumatic disorders such as rheumatoid arthritis, progressive systemic sclerosis (scleroderma); systemic lupus erythematosus; spondyloarthritis including ankylosing spondylitis, psoriatic arthritis, enteropathic arthritis and reactive arthritis. Also contemplated is uveitis including Vogt-Koyanagi-Harada disease, idiopathic anterior and posterior uveitis, and uveitis associated with spondyloarthritis. Use of IL-23 antigen binding proteins is also contemplated for the treatment of autoimmune disorders including multiple sclerosis; autoimmune myocarditis; type 1 diabetes and autoimmune thyroiditis.

Degenerative conditions of the gastrointestinal system are treatable or preventable with IL-23 antigen binding proteins. Such gastrointestinal disorders including inflammatory bowel disease: Crohn's disease, ulcerative colitis and Celiac disease.

Also included are use of IL-23 antigen binding proteins in treatments for graft-versus-host disease, and complications such as graft rejection, resulting from solid organ transplantation, such as heart, liver, skin, kidney, lung or other transplants, including bone marrow transplants.

Also provided herein are methods for using IL-23 antigen binding proteins to treat various oncologic disorders including various forms of cancer including colon, stomach, prostate, renal cell, cervical and ovarian cancers, and lung cancer (SCLC and NSCLC). Also included are solid tumors, including sarcoma, osteosarcoma, and carcinoma, such as adenocarcinoma and squamous cell carcinoma, esophogeal cancer, gastric cancer, gall bladder carcinoma, leukemia, including acute myelogenous leukemia, chronic myelogenous leukemia, myeloid leukemia, chronic or acute lymphoblastic leukemia and hairy cell leukemia, and multiple myeloma.

Diagnostic Methods

The antigen binding proteins of the described can be used for diagnostic purposes to detect, diagnose, or monitor diseases and/or conditions associated with IL-23. Examples of methods useful in the detection of the presence of IL-23 include immunoassays, such as the enzyme linked immunosorbent assay (ELISA) and the radioimmunoassay (RIA).

For diagnostic applications, the antigen binding protein typically will be labeled with a detectable labeling group. Suitable labeling groups include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labelling group is coupled to the antigen binding protein via spacer arms of various lengths to reduce potential steric hindrance. Various methods for labelling proteins are known in the art and may be used.

Other diagnostic methods are provided for identifying a cell or cells that express IL-23. In a specific embodiment, the antigen binding protein is labeled with a labeling group and the binding of the labeled antigen binding protein to IL-23 is detected. In a further specific embodiment, the binding of the antigen binding protein to IL-23 is detected in vivo. In a further specific embodiment, the IL-23 antigen binding protein is isolated and measured using techniques known in the art. See, for example, Harlow and Lane, 1988, *Antibodies: A Laboratory Manual*, New York: Cold Spring Harbor (ed. 1991 and periodic supplements); John E. Coligan, ed., 1993, *Current Protocols In Immunology* New York: John Wiley & Sons.

Other methods provide for detecting the presence of a test molecule that competes for binding to IL-23 with the antigen binding proteins provided. An example of one such assay would involve detecting the amount of free antigen binding protein in a solution containing an amount of IL-23 in the presence or absence of the test molecule. An increase in the amount of free antigen binding protein (i.e., the antigen binding protein not bound to IL-23) would indicate that the test molecule is capable of competing for IL-23 binding with the antigen binding protein. In one embodiment, the antigen binding protein is labeled with a labeling group. Alternatively, the test molecule is labeled and the amount of free test molecule is monitored in the presence and absence of an antigen binding protein.

Methods of Treatment: Pharmaceutical Formulations, Routes of Administration

Pharmaceutical compositions that comprise a therapeutically effective amount of one or a plurality of the antigen binding proteins and a pharmaceutically acceptable excipient, diluent, carrier, solubilizer, emulsifier, preservative, and/or adjuvant are provided. In addition, methods of treating a patient by administering such pharmaceutical composition are included. The term "patient" includes human patients. The terms "treat" and "treatment" encompass alleviation or prevention of at least one symptom or other aspect of a disorder, or reduction of disease severity, and the like. The term "therapeutically effective amount" or "effective amount" refers to the amount of an IL-23 antigen binding protein determined to produce any therapeutic response in a mammal. Such therapeutically effective amounts are readily ascertained by one of ordinary skill in the art.

An antigen binding protein need not affect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. Certain methods provided herein comprise administering to a patient an IL-23 antagonist (such as the antigen binding proteins disclosed herein) in an amount and for a time sufficient to induce a sustained improvement over baseline of an indicator that reflects the severity of the particular disorder.

As is understood in the pertinent field, pharmaceutical compositions comprising the molecules of the invention are administered to a patient in a manner appropriate to the indication. Pharmaceutical compositions may be administered by any suitable technique, including but not limited to, parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments.

Use of antigen binding proteins in ex vivo procedures also is contemplated. For example, a patient's blood or other bodily fluid may be contacted with an antigen binding protein that binds IL-23 ex vivo. The antigen binding protein may be bound to a suitable insoluble matrix or solid support material.

Advantageously, antigen binding proteins are administered in the form of a composition comprising one or more additional components such as a physiologically acceptable carrier, excipient or diluent. Optionally, the composition additionally comprises one or more physiologically active agents for combination therapy. A pharmaceutical composition may comprise an IL-23 antigen binding protein together with one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or dextrins, a chelating agent such as EDTA, glutathione, a stabilizer, and an excipient. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in any Remington's Pharmaceutical Sciences including the $21^{st}$ Ed. (2005), Mack Publishing Company, Easton, Pa.

Kits for use by medical practitioners include an IL-23 antigen binding protein and a label or other instructions for use in treating any of the conditions discussed herein. In one embodiment, the kit includes a sterile preparation of one or more IL-23 binding antigen binding proteins, which may be in the form of a composition as disclosed above, and may be in one or more vials.

Dosages and the frequency of administration may vary according to such factors as the route of administration, the particular antigen binding proteins employed, the nature and severity of the disease to be treated, whether the condition is acute or chronic, and the size and general condition of the subject. Appropriate dosages can be determined by procedures known in the pertinent art, e.g. in clinical trials that may involve dose escalation studies.

A typical dosage may range from about 0.1 µg/kg to up to about 30 mg/kg or more, depending on the factors mentioned above. In specific embodiments, the dosage may range from 0.1 µg/kg up to about 30 mg/kg, optionally from 1 µg/kg up to about 30 mg/kg, optionally from 10 µg/kg up to about 10 mg/kg, optionally from about 0.1 mg/kg to 5 mg/kg, or optionally from about 0.3 mg/kg to 3 mg/kg.

Dosing frequency will depend upon the pharmacokinetic parameters of the particular human IL-23 antigen binding protein in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Appropriate dosages may be ascertained through use of appropriate dose-response data. An IL-23 antigen binding protein of the invention may be administered, for example, once or more than once, e.g., at regular intervals over a period of time. In particular embodiments, an IL-23 antigen binding protein is administered over a period of at least a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the antigen binding protein is administered until the patient manifests a medically relevant degree of improvement over baseline for the chosen indicator or indicators.

It is contemplated that an IL-23 antigen binding protein be administered to the patient in an amount and for a time sufficient to induce an improvement, preferably a sustained improvement, in at least one indicator that reflects the severity of the disorder that is being treated. Various indicators that reflect the extent of the patient's illness, disease or condition may be assessed for determining whether the amount and time of the treatment is sufficient. Such indicators include, for example, clinically recognized indicators of disease severity, symptoms, or manifestations of the disorder in question. In one embodiment, an improvement is considered to be sustained if the subject exhibits the improvement on at least two occasions separated by two to four weeks. The degree of improvement generally is determined by a physician, who may make this determination based on signs, symptoms, biopsies, or other test results, and who may also employ questionaires that are administered to the subject, such as quality-of-life questionaires developed for a given disease.

Particular embodiments of methods and compositions of the invention involve the use of an IL-23 antigen binding protein and one or more additional IL-23 antagonists, for example, two or more antigen binding proteins of the invention, or an antigen binding protein of the invention and one or more other IL-23 antagonists. Also provided are IL-23 antigen binding proteins administered alone or in combination with other agents useful for treating the condition with which the patient is afflicted. Examples of such agents include both proteinaceous and non-proteinaceous drugs. Such agents include therapeutic moieties having anti-inflammatory properties (for example, non-steroidal anti-inflammatory agents, steroids, immunomodulators and/or other cytokine inhibitors such as those that antagonize, for example, IFN-γ, GM-CSF, IL-6, IL-8, IL-17, IL-22 and TNFs), or of an IL-23 antigen binding protein and one or more other treatments (e.g., surgery, ultrasound, or treatment effective to reduce inflammation). When multiple therapeutics are co-administered, dosages may be adjusted accordingly, as is recognized or known in the pertinent art. Useful agents that may be combined with IL-23 antigen binding proteins include those used to treat, for example, Crohn's disease or ulcerative colitis, such as aminosalicylate (for example, mesalamine), corticosteroids (including predisone), antibiotics such as metronidazole or ciprofloxacin (or other antibiotics useful for treating, for example, patients afflicted with fistulas), and immunosuppressives such as azathioprine, 6-mercaptopurine, methotrexate, tacrolimus and cyclosporine. Such agent(s) may be administered orally or by another route, for example via suppository or enema. Agents which may be combined with IL-23 binding proteins in treatment of psoriasis include corticosteroids, calcipotriene and other vitamin D derivatives, acetretin and other retinoic acid derivatives, methotrexate, tacrolimus, and cyclosporine used topically or systemically. Such agents can be administered simultaneously, consecutively, alternately, or according to any other regimen that allows the total course of therapy to be effective.

In addition to human patients, IL-23 antigen binding proteins are useful in the treatment of non-human animals, such as domestic pets (dogs, cats, birds, primates, etc.), domestic farm animals (horses cattle, sheep, pigs, birds, etc). In such instances, an appropriate dose may be determined according to the animal's body weight. For example, a dose of 0.2-1 mg/kg may be used. Alternatively, the dose is determined according to the animal's surface area, an exemplary dose ranging from 0.1-20 mg/m2, or more preferably, from 5-12 mg/m2. For small animals, such as dogs or cats, a suitable dose is 0.4 mg/kg. IL-23 antigen binding protein (preferably constructed from genes derived from the recipient species) is administered by injection or other suitable route one or more times per week until the animal's condition is improved, or it may be administered indefinitely.

The following examples, including the experiments conducted and the results achieved, are provided for illustrative purposes only and are not to be construed as limiting the scope of the appended claims.

EXAMPLES

Example 1

Generation of Human IL-23 Antibodies

XenoMouse™ technology (Amgen, Thousand Oaks, Calif.) was used to develop human monoclonal antibodies that recognize and inhibit native human IL-23 activity while sparing human IL-12. The antibodies also recognize and inhibit recombinant cynomologous IL-23 but do not recognize murine or rat IL-23.

Antibodies were selected for recognition and complete inhibition of native human IL-23 obtained from human monocyte-derived dendritic cells (MoDCs), using the STAT-luciferase reporter assay described below. Human monocytes were isolated from peripheral blood mononuclear cells from healthy donors using negative selection (Monocyte Isolation Kit II, Miltenyi Biotec, Auburn, Calif.). MoDCs were generated by culturing monocytes with human GM-CSF (50 ng/ml) and human IL-4 (100 ng/ml) for 7 days in RPMI 1640 with 10% fetal bovine serum complete medium. MoDCs were then washed twice with PBS followed by stimulation with human CD40L (1 µg/ml) for an additional 48 hours. CD40L-stimulated MoDC supernatant contains IL-23, IL-12 and IL-12/23p40. ELISAs are used to determine the amount of IL-12p70 (R&D System, Minneapolis, Minn.), IL-23 (eBiosciences, San Diego, Calif.) and IL-12/23p40 (R&D Systems). The STAT-luciferase assay responds to IL-23 and not to IL-12 or to free IL-12/23p40, therefore the assay could be used with crude supernatants to assess IL-23 activity. For use in the NK cell assay, described below, the native human IL-23 crude supernatant was purified using an IL-23 affinity column followed by size exclusion chromatography. Concentration was determined using an IL-23 specific ELISA (eBiosciences).

Figure 1B:
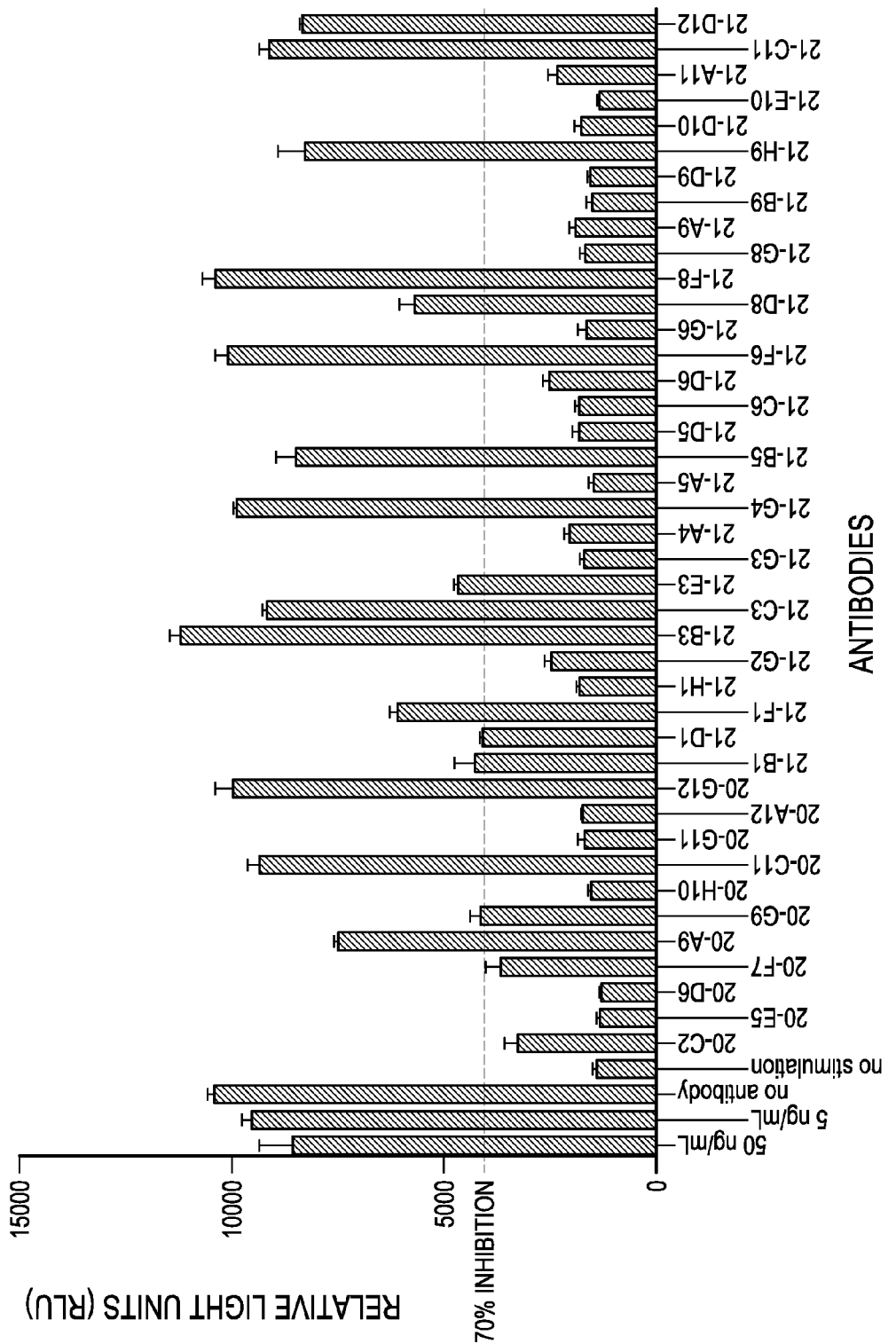
FIG. 1B: Results from STAT-luciferase reporter assay using native human IL-23. Only half of those antibodies that completely inhibited recombinant human IL-23 were able to completely inhibit native human IL-23

The purified antibody supernatants were also tested against recombinant human (rhu) IL-23 and recombinant cynomolgous (cyno) IL-23 in the STAT-luciferase assay. Of the antibodies tested that completely inhibited recombinant human IL-23, only half of those antibodies recognized and completely inhibited native human IL-23. Recognition and complete inhibition of recombinant human IL-23 was not predictive of, nor correlated to, recognition and complete inhibition of native human IL-23. As shown in FIGS. 1A and 1B, of the antibody supernatants that completely inhibited recombinant human IL-23, only half of those antibodies completely inhibited native human IL-23. Those antibodies that recognized and completely inhibited native human IL-23 were selected for further characterization.

Example 2

Functional Assays a) STAT-Luciferase Assay

It is known that IL-23 binds its heterodimeric receptor and signals through JAK2 and Tyk2 to activate STAT 1, 3, 4 and 5. In this assay, cells transfected with a STAT/luciferase reporter gene are used to assess the ability of the IL-23 antibodies to inhibit IL-23-induced bioactivity.

Chinese hamster ovary cells expressing human IL-23 receptor are transiently transfected with STAT-luciferase reporter overnight. IL-23 antibodies are serially diluted (12 points of 1:4 serial dilutions starting at 37.5 µg/ml) into 96 well plates. Native human IL-23 (preparation method is described in Example 1) is added to each well at a concentration of 2 ng/ml and incubated at room temperature for 15-20 minutes. The transiently transfected cells are added ($8 \times 10^3$ cells) to a final volume of 100 µl/well and incubated for 5 hours at 37° C., 10% $CO_2$. Following incubation, cells are lysed using 100 µL/well Glo Lysis buffer (1×) (Promega, Madison, Wis.) at room temperature for 5 minutes. Fifty microliters of cell lysate is added to a 96 well plate along with 50 µL Bright-Glo luciferase substrate (Promega) and read on a luminometer.

Statistical analysis can be performed using GraphPad PRISM software (GraphPad Software, La Jolla, Calif.). Results can be expressed as the mean±standard deviation (SD).

As seen in TABLE 5, all IL-23 antibodies potently and completely inhibited native human IL-23-induced STAT/luciferase reporter in a dose dependent manner. The antibodies also potently and completely inhibited recombinant human (rhu) IL-23 and recombinant cyno (cyno) IL-23. The antibodies all had $IC_{50}$ values in the picomolar range.

TABLE 5

Table of mean $IC_{50}$ (pM) values for IL-23 antibodies in the STAT-luciferase assay.

| antibody | Native huIL-23 | | rhuIL-23 | | Cyno IL-23 | |
|---|---|---|---|---|---|---|
| | $IC_{50}$ +/− SD | Repeats | $IC_{50}$ +/− SD | Repeats | $IC_{50}$ +/− SD | Repeats |
| A | 114 +/− 70 | 3 | 190 +/− 99 | 3 | 379 +/− 213 | 3 |
| B | 45 +/− 5 | 4 | 100 +/− 59 | 4 | 130 +/− 60 | 3 |
| C | 107 +/− 31 | 3 | 211 +/− 93 | 3 | 376 +/− 89 | 3 |
| D | 65 +/− 5 | 3 | 107 +/− 30 | 3 | 184 +/− 77 | 3 |
| E | 140 +/− 52 | 3 | 142 +/− 52 | 3 | 188 +/− 59 | 3 |
| F | 86 +/− 47 | 4 | 187 +/− 116 | 4 | 366 +/− 219 | 4 |
| G | 156 +/− 74 | 5 | 296 +/− 133 | 5 | 421 +/− 174 | 5 |
| H | 192 +/− 35 | 4 | 253 +/− 184 | 4 | 1024 +/− 533 | 4 |
| I | 208 +/− 33 | 3 | 338 +/− 140 | 3 | 650 +/− 42 | 3 |
| J | 83 +/− 54 | 2 | 26 +/− 6 | 2 | 56 +/− 2 | 2 |
| K | 71 +/− 38 | 3 | 43 +/− 20 | 3 | 61 +/− 10 | 3 |
| L | 113 +/− 80 | 3 | 23 +/− 7 | 3 | 47 +/− 1 | 3 |
| M | 34 +/− 11 | 2 | 40 +/− 8 | 2 | 56 +/− 6 | 2 |
| N | 361 +/− 164 | 3 | 145 | 1 | 238 | 1 | b) NK Cell Assay

It is known that IL-23 acts on natural killer cells to induce expression of pro-inflammatory cytokines, such as interferon γ (IFNγ). In this assay, human primary natural killer (NK) cells are used to assess the ability of the IL-23 antibodies to inhibit IL-23-induced IFNγ activity in cells expressing the native receptor for human IL-23.

NK cells are isolated from multiple human donors via negative selection (NK Cell Isolation Kit, Miltenyi Biotec, Auburn, Calif.). Purified NK cells ($1 \times 10^6$ cells/ml) are added to 6 well plates in RPMI 1640 plus 10% fetal bovine serum complete medium supplemented with recombinant human IL-2 (10 ng/ml, R&D Systems, Minneapolis, Minn.), to a final volume of 10 ml/well. Cells are cultured for 7 days at 37° C., 5% $CO_2$. The IL-2-activated NK cells are then stimulated with rhuIL-23 or cyno IL-23 (10 ng/ml) and recombinant human IL-18 (20 ng/ml, R&D Systems, Minneapolis, Minn.) in the presence of serial dilutions (11 points of 1:3 serial dilutions starting at 3 μg/ml) of IL-23 antibodies for 24 hours. IFNγ levels are measured in the supernatant by IFNγ ELISA (R&D Systems, Minneapolis, Minn.) according to manufacturer's instructions.

Statistical analysis can be performed using GraphPad PRISM software. Results can be expressed as the mean±standard deviation (SD).

As seen in TABLE 6, all antibodies potently inhibited rhuIL-23 and cyno IL-23-induced IFNγ expression in NK cells in a dose dependent manner. The antibodies all had $IC_{50}$ values in the picomolar range. The assay was performed on a subset of antibodies using native human IL-23 (30 μg/ml, preparation method is described in Example 1) and rhuIL-18 (40 ng/ml, R&D Systems) and yielded the results shown in TABLE 6. Consistent with the selection for IL-23 specific antibodies, these anti-IL-23 antibodies had no effect on IL-12 stimulated IFNγ production in NK cells using the assay described above, whereas an IL-12p35 specific neutralizing antibody, mAb219 (R&D Systems, Minneapolis, Minn.) potently inhibited recombinant human IL-12.

TABLE 6

Table of mean $IC_{50}$ (pM) values for IL-23 antibodies in the NK cell assay.

| antibody | Native huIL-23 $IC_{50}$ +/− SD | Repeats | rhuIL-23 $IC_{50}$ +/− SD | Repeats | Cyno IL-23 $IC_{50}$ +/− SD | Repeats |
|---|---|---|---|---|---|---|
| A |  |  | 42 +/− 12 | 2 | 31 +/− 21 | 2 |
| B | 85 +/− 30 | 2 | 48 +/− 30 | 3 | 19 +/− 8 | 2 |
| C |  |  | 32 +/− 19 | 4 | 29 +/− 16 | 2 |
| D |  |  | 37 +/− 21 | 2 | 29 +/− 19 | 2 |
| E | 158 +/− 50 | 2 | 57 +/− 14 | 3 | 21 +/− 3 | 2 |
| F |  |  | 25 +/− 15 | 2 | 21 +/− 17 | 2 |
| G | 152 +/− 72 | 2 | 45 +/− 30 | 3 | 23 +/− 8 | 2 |
| H |  |  | 29 +/− 28 | 2 | 33 +/− 17 | 2 |
| I |  |  | 69 | 1 | 52 | 1 |
| J |  |  | 4 +/− 3 | 2 | 5 +/− 3 | 2 |
| K |  |  | 7 +/− 2 | 2 | 8 +/− 6 | 2 |
| L |  |  | 3 +/− 1 | 2 | 4 +/− 1 | 2 |
| M |  |  | 8 | 1 | 12 | 1 | c) Human Whole Blood Assay

Human whole blood is collected from multiple healthy donors using Refludan® (Bayer Pittsburgh, Pa.) as an anticoagulant. The final concentration of Refludan® in whole blood is 10 μg/ml. A stimulation mixture of rhuIL-23 or cyno IL-23 (final concentration 1 ng/ml)+rhuIL-18 (final concentration 20 ng/ml)+rhuIL-2 (final concentration 5 ng/ml) in RPMI 1640+10% FBS, is added to a 96 well plate, final volume 20 μl/well. Serially diluted IL-23 antibodies (11 points of 1:3 serial dilutions starting from 3 μg/ml) are added at 20 μl/well and incubated with the stimulation mixture for 30 minutes at room temperature. Whole blood is then added (120 μl/well) and the final volume adjusted to 200 μl/well with RPMI 1640+10% FBS. The final concentration of whole blood is 60%. The plates are incubated for 24 hours at 37° C., 5% $CO_2$. Cell free supernatants are harvested and IFNγ levels are measured from the supernatants by IFNγ ELISA (R&D Systems) according to manufacturer's instructions.

Statistical analysis can be performed using GraphPad PRISM software. Results can be expressed as the mean±standard deviation (SD).

As seen in TABLE 7, all antibodies potently inhibited rhuIL-23-induced and cyno-IL-23-induced IFNγ expression in whole blood cells in a dose dependent manner. The antibodies all had $IC_{50}$ values in the picomolar range.

TABLE 7

Table of mean $IC_{50}$ (pM) values for IL-23 antibodies in the IFNγ human whole blood assay

| antibody | rhuIL-23 $IC_{50}$ +/− SD | Repeats | Cyno IL-23 $IC_{50}$ +/− SD | Repeats |
|---|---|---|---|---|
| B | 117 +/− 94 | 7 | 161 +/− 95 | 6 |
| E | 29 +/− 8 | 3 | 54 +/− 33 | 3 |
| G | 53 +/− 13 | 3 | 93 +/− 44 | 3 |
| F | 66 +/− 13 | 3 | 166 +/− 189 | 3 |
| D | 88 +/− 6 | 3 | 110 +/− 14 | 3 |
| C | 97 +/− 31 | 3 | 186 +/− 194 | 3 | d) IL-22 Assay

It is known that IL-23 is a potent inducer of proinflammatory cytokines. IL-23 acts on activated and memory T cells and promotes the survival and expansion of Th17 cells which produce proinflammatory cytokines including IL-22. In this assay, human whole blood is used to assess the ability of the IL-23 antibodies to inhibit IL-23-induced IL-22 production.

A whole blood assay is conducted in the same manner as described above with the modification of using rhuIL-23 or cynoIL-23 at 1 ng/ml and rhuIL-18 at 10 ng/ml to induce IL-22 production. IL-22 concentration is determined by IL-22 ELISA (R&D Systems, Minneapolis, Minn.).

As seen in TABLE 8, the antibodies potently inhibited rhuIL-23-induced and cyno IL-23-induced IL-22 production in whole blood cells in a dose dependent manner. The antibodies all had $IC_{50}$ values in the picomolar range.

TABLE 8

Table of mean $IC_{50}$ (pM) values for IL-23 antibodies in the IL-22 human whole blood assay

| antibody | rhuIL-23 $IC_{50}$ +/− SD | Repeats | Cyno IL-23 $IC_{50}$ +/− SD | Repeats |
|---|---|---|---|---|
| B | 117 +/− 68 | 4 | 113 +/− 65 | 3 |
| E | 87 +/− 109 | 3 | 56 +/− 60 | 3 |
| G | 83 +/− 59 | 3 | 66 +/− 45 | 3 |

Example 3

Determining the Equilibrium Dissociation Constant ($K_D$) for Anti-IL-23 Antibodies Using KinExA Technology Binding affinity of rhuIL-23 to IL-23 antibodies is evaluated using a kinetic exclusion assay (KinExA assay, Sapidyne Instruments, Inc., Boise, Id.). Normal human serum (NHS)-activated Sepharose 4 fast flow beads (Amersham Biosciences, part of GE Healthcare, Uppsala, Sweden), are precoated with rhuIL-23 and blocked with 1 m Tris buffer with 10 mg/mL BSA. 50 pM of IL-23 antibody is incubated with rhuIL-23 (12 points of 1:2 dilutions starting from 800 pM) at room temperature for 72 hours before it is run through the rhuIL-23-coated Sepharose beads. The amount of the bead-bound antibody was quantified by fluorescent (Cy5) labeled goat anti-human-Fc antibody (Jackson Immuno Research, West Grove, Pa.). The binding signal is proportional to the amount of free antibody at equilibrium.

The dissociation equilibrium constant ($K_D$) and the association rate ($K_{on}$) are obtained from curve fitting using KinExA Pro software. The dissociation rate ($K_{off}$) is derived from: $K_D = K_{off}/K_{on}$ As seen in TABLE 9, the antibodies have high affinity for binding to human IL-23. All had $K_D$ values in the low to sub pM range.

TABLE 9

Table of $K_D$ (pM), $K_{on}$ (1/MS) and $K_{off}$ (1/s) rates

| Antibody | KD (pM) | Kon (1/MS) | Koff (1/s) |
|---|---|---|---|
| E | 0.131 | 9.12E+05 | 1.4E−07 |
| D | 0.126 | 1.72E+06 | 2.2E−07 |
| B | 3.99 | 1.17E+06 | 4.7E−06 |
| C | 2.56 | 1.36E+06 | 4.1E−06 |
| F | 2.62 | 5.69E+05 | 1.5E−06 |
| L | 1.08 | 3.34E+06 | 3.7E−06 |
| G | 2.00 | 4.00E+05 | 8.1E−07 |

Example 4

Structure Determination Using X-Ray Crystallography

One way to determine the structure of an antibody-antigen complex is by using X-ray crystallography, see for example, Harlow and Lane Antibodies: A Laboratory Manual Cold Spring Harbor Laboratory Press, Cold Spring Harbor, N.Y. (1990), p. 23. The crystal structure of IL-23 has been determined, (see Lupardus and Garcia, J Mol Biol, 2008, 382: 931-941) and the crystal structure of an IL-23/Fab complex has been disclosed, (see Beyer et al. J Mol Biol, 2008. 382(4): 942-55). Structural determination of IL-23 with Fab fragments of antibodies claimed herein was obtained using X-ray crystallography.
Protein for Crystallization A recombinantly derived human IL-23 heterodimer was used for the crystallization studies (see Beyer et al., supra). The sequence of the human p19 subunit comprised of residues 20-189 of SEQ ID NO: 145, the signal sequence of SEQ ID NO:154 and a C-terminal 6-His tag SEQ ID NO:155. The sequence of the human p40 subunit was mutated from asparagine to glutamine at position 222 of SEQ ID NO:147 in order to prevent glycosylation at this site (Beyer, et al., supra).

Fabs derived from Antibody B and Antibody E were expressed on an IgG1 scaffold that incorporated a caspase cleavage site. The Fabs were processed by means of protease cleavage.
Complex Formation and Crystallization The IL-23-Antibody B Fab complex was made by mixing a 2× molar excess of the Antibody B Fab with the human heterodimeric IL-23 described above. The complex was purified by size exclusion chromatography to remove excess Antibody B Fab and concentrated to ~12 mg/ml for crystallization. The IL-23-Antibody B Fab complex crystallized in 0.1 M Hepes pH 7, 8% PEG 8000.

The IL-23-Antibody E Fab complex was made by mixing a 2× molar excess of the Antibody E Fab with the human heterodimeric IL-23 described above. The complex was methylated using a JBS Methylation Kit according to manufacturer's instructions (Jena Bioscience, Jena, Germany). The complex was then treated with PNGase to deglycosylate the protein. Following these treatments, the complex was purified by size exclusion chromatography to remove excess Antibody E Fab and concentrated to 13.5 mg/ml for crystallization. The IL-23-Antibody E Fab complex crystallized in 0.1 M Tris pH 8.5, 0.2 M magnesium chloride, 15% PEG 4000.
Data Collection and Structure Determination IL-23-Antibody B Fab crystals grew in the P2$_1$ space group with unit cell dimensions a=70.93, b=71.27, c=107.37 Å, β=104.98° and diffract to 2.0 Å resolution. The IL-23-Antibody B Fab structure was solved by molecular replacement with the program MOLREP (CCP4, *The CCP4 suite: programs for protein crystallography*. Acta Crystallogr D Biol Crystallogr, 1994. 50(Pt 5): p. 760-3) using the IL-23 structure (Beyer et al. supra) as the starting search model. Keeping the IL-23 solution fixed, an antibody variable domain was used as a search model. Keeping the IL-23-antibody variable domain solution fixed, an antibody constant domain was used as a search model. The complete structure was improved with multiple rounds of model building with Quanta and refinement with cnx (Brunger, et al., Acta Crystallogr D Biol Crystallogr, 1998, 54(Pt 5): p. 905-21).

Distances between protein atoms were calculated using the program PyMOL (DeLano, W. L. The PyMOL Graphics System. Palo Alto, 2002) (Schrodinger, LLC; New York, N.Y.)). Amino acids were chosen if at least one atom was located within the required distance threshold to the partner protein.

Boundaries of the A, B, C and D helices of the p19 subunit of IL-23 when bound to the Antibody B Fab include A helix residues 28-47, B helix residues 86-105, C helix residues 119-134 and D helix residues 154-187 of SEQ ID NO:145.

The regions of interaction on the IL-23p19 subunit when bound to the Antibody B Fab include residues within Ser46-Glu58, Glu112-Glu123 and Pro155-Phe163 of SEQ ID NO:145.

IL-23p19 subunit amino acid residues with atoms 4 Å or less from the Antibody B Fab include Ser46, Ala47, His48, Pro49, Leu50, His53, Met54, Asp55, Glu58, Pro113, Ser114, Leu115, Leu116, Pro120, Val121, Trp156, Leu159, Leu160, Arg162 and Phe163 of SEQ ID NO:145. IL-23p19 amino acid residues with atoms between 4 Å and 5 Å from the Antibody B Fab include Val51, Arg57, Glu112, Asp118, Ser119, Gln123, Pro155 of SEQ ID NO:145.

IL-23p40 subunit amino acid residues with atoms 4 Å or less from the Antibody B Fab include Glu 122 and Lys 124 of SEQ ID NO:147.

The Antibody B Fab heavy chain amino acid residues with atoms 4 Å or less from the IL-23 heterodimer include Gly32, Gly33, Tyr34, Tyr35, His54, Asn58, Thr59, Tyr60, Lys66, Arg101, Gly102, Phe103, Tyr104 and Tyr105 of SEQ ID NO:46. The Antibody B Fab heavy chain amino acid residues with atoms≤5 Å from the IL-23 heterodimer include Ser31, Gly32, Gly33, Tyr34, Tyr35, His54, Ser56, Asn58, Thr59, Tyr60, Lys66, Arg101, Gly102, Phe103, Tyr104 and Tyr105 of SEQ ID NO:46.

The Antibody B Fab light chain amino acid residues with atoms 4 Å or less from the IL-23 heterodimer include Ser30, Ser31, Trp32, Tyr49, Ser52, Ser53, Ala91, Asn92, Ser93, Phe94, and Phe96 of SEQ ID NO:15. The Antibody B Fab light chain amino acid residues with atoms≤5 Å from the IL-23 heterodimer include Ser30, Ser31, Trp32, Tyr49, Ala50, Ser52, Ser53, Ser56, Ala91, Asn92, Ser93, Phe94, and Phe96 of SEQ ID NO:15

The IL-23-Antibody E Fab complex crystals grew in the P222$_1$ space group with unit cell dimensions a=61.60, b=97.59, c=223.95 Å and diffract to 3.5 Å resolution. The IL-23-Antibody E Fab complex structure was solved by molecular replacement with the program Phaser (CCP4, supra) using the IL-23 structure, an antibody variable domain, and an antibody constant domain as the three starting search models, as described above. The complete structure was improved with multiple rounds of model building with Quanta and refinement with cnx (Brunger, et al., supra). The Antibody E Fab constant domain was left out of the final refined structure due to very poor electron density for that portion of the protein.

The regions of interaction on the IL-23p19 subunit identified when bound to the Antibody E Fab include residues within Ser46-His53, Glu112-Val120 and Trp156-Phe163 of SEQ ID NO:145.

IL-23p19 amino acid residues with atoms 4 Å or less from the Antibody E Fab include Ser46, Ala47, His48, Pro49, Leu50, Glu112, Pro113, Ser114, Leu115, Leu116, Pro117, Asp118, Ser119, Pro120, Trp156, Leu159, Leu160 and Phe163 of SEQ ID NO: 145. IL-23p19 amino acid residues with atoms between 4 Å and 5 Å from the Antibody E Fab include His53 of SEQ ID NO:145.

IL-23p40 amino acid residues with atoms 4 Å or less from the Antibody E Fab include Lys121, Glu 122, Pro123 and Asn 125 of SEQ ID NO:147.

The Antibody E Fab heavy chain amino acid residues with atoms 4 Å or less from the IL-23 heterodimer include Gly26, Phe27, Thr28, Ser31, Tyr53, Tyr59, Tyr102, Ser104, Ser105, Trp106, Tyr107, and Pro108 of SEQ ID NO:31. The Antibody E Fab heavy chain amino acid residues with atoms≤5 Å from the IL-23 heterodimer include Gln1, Gly26, Phe27, Thr28, Ser30, Ser31, Tyr32, Trp52, Tyr53, Tyr59, Arg100, Tyr102, Thr103, Ser104, Ser105, Trp106, Tyr107, and Pro108 of SEQ ID NO:31.

The Antibody E Fab light chain amino acid residues with atoms 4 Å or less from the IL-23 heterodimer include Ala31, Gly32, Tyr33, Asp34, Tyr51, Gly52, Asn55, Lys68, and Tyr93 of SEQ ID NO:1. The Antibody B Fab light chain amino acid residues with atoms≤5 Å from the IL-23 heterodimer include Thr29, Ala31, Gly32, Tyr33, Asp34, Tyr51, Gly52, Asn55, Lys68, Tyr93, and Trp100 of SEQ ID NO:1.

Example 5

Determination of IL-23-Antibody Complex Contact Residues Through Solvent Accessible Surface Area Differences The residue contacts in the paratope (the portion of the antibody that recognizes the antigen) and the portion of the antigen that it binds bound by the paratope in a human IL-23-Antibody B Fab complex and in a human IL-23-Antibody E Fab complex were determined using solvent accessible surface area differences. The solvent accessible surface area calculations were performed using Molecular Operating Environment (Chemical Computing Group, Montreal, Quebec).

The solvent accessible surface area differences of the paratope residues in the IL-23-Antibody B Fab complex were calculated by setting the Antibody B Fab residues as the desired set. The structural information obtained in Example 4 for the IL-23-Antibody B Fab complex was used and the residue solvent accessible surface area of the amino acid residues of the Antibody B Fab in the presence of the IL-23 heterodimer were calculated and represent the "bound areas" for the set.

The residue solvent accessible surface area of each of the Antibody B Fab residues in the absence of the IL-23 antigen were calculated and represent the "free areas" of the set.

The "bound areas" were then subtracted from the "free areas" resulting in the "solvent exposed surface area difference" for each residue in the set. The Antibody B Fab residues that had no change in surface area, or a zero difference, had no contact with the residues of the IL-23 antigen when complexed. The Antibody B Fab residues that had a difference value≥10 Å² were considered to be in significant contact with residues in the IL-23 antigen such that these Antibody B Fab residues were at least partially to completely occluded when the Antibody B Fab was bound to human IL-23. This set of Antibody B Fab residues make up the "covered patch", the residues involved in the structure of the interface when Antibody B Fab is bound to human IL-23, see Tables 10 and 11. The Antibody B Fab residues in this covered patch may not be involved in binding interactions with residues of the IL-23 antigen, but mutation of any single residue within the covered patch could introduce energetic differences that would impact the binding of Antibody B Fab to human IL-23. With the exception of Tyr49, all of the residues are located in the CDR regions of the Antibody B Fab light and heavy chains. These residues were also within 5 Å or less of the 11-23 antigen when bound to the Antibody B Fab, as described in Example 4.

TABLE 10

Solvent Accessibility Surface Area Differences for Antibody B Fab Light Chain

| Residue AHO Number | Residue Position SEQ ID NO: 15 | Solvent exposed surface area difference (Å²) |
|---|---|---|
| Ser32 | Ser30 | 44.9 |
| Ser33 | Ser31 | 41.1 |
| Trp40 | Trp32 | 79.0 |
| Tyr57 | Tyr49 | 40.7 |
| Ala58 | Ala50 | 20.3 |
| Ser68 | Ser52 | 43.6 |
| Ser69 | Ser53 | 38.9 |
| Ser72 | Ser56 | 19.1 |
| Asn110 | Asn92 | 34.0 |
| Phe135 | Phe94 | 51.4 |

TABLE 11

Solvent Accessibility Surface Area Differences for Antibody B Fab Heavy Chain

| Residue AHO Number | Residue Positioin SEQ ID NO: 46 | Solvent exposed surface area difference (Å²) |
|---|---|---|
| Ser33 | Ser31 | 18.2 |
| Gly34 | Gly32 | 49.5 |
| Gly38 | Gly33 | 33.8 |
| Tyr39 | Tyr34 | 51.4 |
| Tyr40 | Tyr35 | 30.7 |
| His59 | His54 | 29.5 |
| Asn67 | Asn58 | 66.7 |
| Thr68 | Thr59 | 26.0 |
| Tyr69 | Tyr60 | 59.4 |
| Lys75 | Lys66 | 32.6 |
| Arg110 | Arg101 | 47.2 |
| Gly111 | Gly102 | 21.7 |
| Phe112 | Phe103 | 35.5 |
| Tyr133 | Tyr104 | 83.0 |
| Tyr134 | Tyr105 | 91.7 |

The solvent accessible surface area differences of the residues in the IL-23-Antibody E Fab complex were calculated as described above. The Antibody E Fab residues that had a difference value≥10 Å² were considered to be in significant contact with residues in the IL-23 antigen and these Antibody E Fab residues were at least partially to completely occluded when the Antibody E Fab was bound to human IL-23. This set of Antibody E Fab residues make up the covered patch, the residues involved in the structure of the interface when the Antibody E Fab is bound to human IL-23, see Tables 12 and 13. The Antibody E Fab residues in this covered patch may not be involved in binding interactions with residues of the IL-23 antigen, but mutation of any single residue within the covered patch could introduce energetic differences that would impact the binding of Antibody E Fab to human IL-23. For the most part, these covered patch residues were located within the CDR regions of the Antibody E Fab heavy and light chains. These residues were also within 5 Å or less of the IL-23 antigen when bound to the Antibody E Fab, as described in Example 4.

TABLE 12

Solvent Accessibility Surface Area Differences for Antibody E Fab Light Chain

| Residue AHO Number | Residue Position SEQ ID NO: 1 | Solvent exposed surface area difference ($Å^2$) |
|---|---|---|
| Ala33 | Ala31 | 11.6 |
| Gly34 | Gly32 | 51.2 |
| Tyr39 | Tyr33 | 47.2 |
| Asp40 | Asp34 | 36.8 |
| Tyr57 | Tyr51 | 16.1 |
| Gly58 | Gly52 | 11.1 |
| Asn69 | Asn55 | 29.4 |
| Lys82 | Lys68 | 20.1 |
| Tyr109 | Tyr93 | 27.3 |
| Ser135 | Ser98 | 11.3 |

TABLE 13

Solvent Accessibility Surface Area Differences for Antibody E Fab Heavy Chain

| Residue AHO Number | Residue Position SEQ ID NO: 31 | Solvent exposed surface area difference ($Å^2$) |
|---|---|---|
| Gln1 | Gln1 | 41.1 |
| Gly27 | Gly26 | 24.6 |
| Thr30 | Thr28 | 82.2 |
| Ser33 | Ser31 | 40.7 |
| Tyr39 | Tyr32 | 30.7 |
| Trp59 | Trp52 | 11.3 |
| Tyr60 | Tyr53 | 44.7 |
| Tyr69 | Tyr59 | 42.4 |
| Lys86 | Lys76 | 17.4 |
| Gly111 | Gly101 | 12.8 |
| Tyr112 | Tyr102 | 103.1 |
| Ser114 | Ser104 | 21.0 |
| Ser115 | Ser105 | 91.4 |
| Trp131 | Trp106 | 145.0 |
| Tyr132 | Tyr107 | 71.6 |
| Pro133 | Pro108 | 20.4 |

The solvent accessible surface area differences of the portion of the IL-23 heterodimer bound by the paratope of the Antibody B Fab were calculated by setting the IL-23 heterodimer residues as the desired set. The structural information obtained in Example 4 for the Antibody B Fab-IL-23 complex was used and the residue solvent accessible surface area of the amino acid residues of the IL-23 heterodimer in the presence of the Antibody B Fab were calculated and represent the bound areas for the set.

The residue solvent accessible surface area of each of the IL-23 heterodimer residues in the absence of the Antibody B Fab were calculated and represent the free areas of the set.

As described above, the bound areas were subtracted from the free areas resulting in the solvent exposed surface area difference for each IL-23 residue. The IL-23 heterodimer residues that had no change in surface area, or a zero difference, had no contact with the residues of the Antibody B Fab when complexed. The IL-23 heterodimer residues that had a difference value≥10 $Å^2$ were considered to be in significant contact with residues of the Antibody B Fab and these 11-23 heterodimer residues were at least partially to completely occluded when the human IL-23 heterodimer was bound to the Antibody B Fab. This set of IL-23 heterodimer residues make up the covered patch, the residues involved in the structure of the interface when the human IL-23 heterodimer is bound to the Antibody E Fab, see Table 14. The 11-23 heterodimer residues in this covered patch may not all be involved in binding interactions with residues on the Antibody B Fab, but mutation of any single residue within the covered patch could introduce energetic differences that would impact the binding of Antibody B Fab to human IL-23. These residues are also within 4 Å or less from the Antibody B Fab, as described Example 4.

TABLE 14

Solvent Accessibility Surface Area Differences for IL-23 heterodimer residues

| | Solvent exposed surface area difference ($Å^2$) |
|---|---|
| p19 residues (SEQ ID NO: 145) | |
| Ser46 | 26.5 |
| Ala47 | 12.7 |
| Pro49 | 59.6 |
| Leu50 | 122.2 |
| His53 | 47.8 |
| Met54 | 13.9 |
| Asp55 | 20.5 |
| Arg57 | 14.6 |
| Glu58 | 96.5 |
| Glu112 | 29.7 |
| Pro113 | 64.8 |
| Ser114 | 30.0 |
| Leu115 | 31.4 |
| Leu116 | 60.0 |
| Asp118 | 14.4 |
| Ser119 | 19.7 |
| Pro120 | 64.7 |
| Pro155 | 19.4 |
| Typ156 | 61.9 |
| Leu159 | 72.8 |
| Leu160 | 27.0 |
| Arg162 | 14.4 |
| Phe163 | 67.5 |
| p40 residues (SEQ ID NO: 147) | |
| Glu122 | 29.1 |
| Lys124 | 60.9 |

The solvent accessible surface area differences of the portion of the IL-23 heterodimer bound by the paratope of the Antibody E Fab were calculated as described above. The IL-23 heterodimer residues that had a difference value≥10 $Å^2$ were considered to be in significant contact with residues of the Antibody E Fab and these 11-23 heterodimer residues were at least partially to completely occluded when the human IL-23 heterodimer was bound to the Antibody E Fab. This set of IL-23 heterodimer residues make up the covered patch, the residues involved in the structure of the interface when the human IL-23 heterodimer is bound to the Antibody E Fab, see Table 15. The 11-23 heterodimer residues in this covered patch may not all be involved in binding interactions with residues on the Antibody E Fab, but mutation of any single residue within the covered patch could introduce energetic differences that would impact the binding of Antibody E Fab to human IL-23. These residues are also within 5 Å or less from the Antibody E Fab, as described in Example 4.

TABLE 15

Solvent Accessibility Surface Area Differences
for IL-23 heterodimer residues

| | Solvent exposed surface area difference (Å²) |
|---|---|
| p19 residues (SEQ ID NO: 145) | |
| Ser46 | 18.7 |
| Ala47 | 14.9 |
| Pro49 | 79.8 |
| Leu50 | 99.5 |
| His53 | 61

```
<211> LENGTH: 111
<212> TYPE: PRT
<213> ORGANISM: Homo sapiens

<400> SEQUENCE: 3

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Ser Asn Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Val Phe Gly Gly Gly Thr Lys Leu Thr Val Leu
            100                 105                 110

<210> SEQ ID NO 4
<211> LENGTH: 115
<212> TYPE: PRT
<213> ORGANISM: Homo sapiens

<400> SEQUENCE: 4

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Lys Gln Gly Ser Gly Val
50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Ser Val Phe Gly Gly Gly Thr Lys Leu
            100                 105                 110

Thr Val Leu
    115

<210> SEQ ID NO 5
<211> LENGTH: 345
<212> TYPE: DNA
<213> ORGANISM: Homo sapiens

<400> SEQUENCE: 5
caggctgtgc tgactcagcc gtcttccctc tctgcatctc ctggagcatc agccagtctc    60
acctgcacct tacgcagtgg catcaatgtt ggtacctaca ggatatactg gtaccagcag   120
aagccaggga gtcctcccca gtatctcctg aggtacaaat cagactcaga taagcagcag   180
ggctctggag tccccagccg cttctctgga tccaaagatg cttcggccaa tgcagggatt   240
ttactcatct ctgggctcca gtctgaggat gaggctgact attactgtat gatttggcac   300
agcagcgctt cggtattcgg cggagggacc aagctgaccg tccta                   345
```

```
<210> SEQ ID NO 6
<211> LENGTH: 14
<212> TYPE: PRT
<213> ORGANISM: Homo sapiens

<400> SEQUENCE: 6

Glu Asn Thr Val Thr Ile Tyr Tyr Asn Tyr Gly Met Asp Val
1               5                   10

<210> SEQ ID NO 7
<211> LENGTH: 116
<212> TYPE: PRT
<213> ORGANISM: Homo sapiens

<400> SEQUENCE: 7

Gln Pro Val Leu Thr Gln Pro Pro Ser Ala Ser Ala Ser Leu Gly Ala
1               5                   10                  15

Ser Val Thr Leu Thr Cys Thr Leu Asn Ser Gly Tyr Ser Asp Tyr Lys
                20                  25                  30

Val Asp Trp Tyr Gln Gln Arg Pro Gly Lys Gly Pro Arg Phe Val Met
            35                  40                  45

Arg Val Gly Thr Gly Gly Ile Val Gly Ser Lys Gly Asp Gly Ile Pro
        50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Ala Asp
                85                  90                  95

His Gly Ser Gly Ser Asn Phe Val Tyr Val Phe Gly Thr Gly Thr Lys
            100                 105                 110

Val Thr Val Leu
        115

<210> SEQ ID NO 8
<211> LENGTH: 348
<212> TYPE: DNA
<213> ORGANISM: Homo sapiens

<400> SEQUENCE: 8
cagcctgtgc tgactcagcc accttctgca tcagcctccc tgggagcctc ggtcacactc      60
acctgcaccc tgaacagcgg ctacagtgat tataaagtgg actggtacca gcagagacca     120
gggaagggcc cccggtttgt gatgcgagtg ggcactggtg ggattgtggg atccaagggg     180
gatggcatcc ctgatcgctt ctcagtcttg ggctcaggcc tgaatcggta cctgaccatc     240
aagaatatcc aggaagagga tgagagtgac taccactgtg gggcagacca tggcagtggg     300
agcaacttcg tgtatgtctt cggaactggg accaaggtca ccgtccta              348

<210> SEQ ID NO 9
<211> LENGTH: 116
<212> TYPE: PRT
<213> ORGANISM: Homo sapiens

<400> SEQUENCE: 9

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asp Tyr Lys
                20                  25                  30

Val Asp Trp Tyr Gln Gln Arg Pro Gly Lys Gly Pro Arg Phe Val Met
            35                  40                  45

Arg Val Gly Thr Gly Gly Ile Val Gly Ser Lys Gly Glu Gly Ile Pro
```

```
                50                  55                  60
Asp Arg Phe Ser Val Leu Gly Ser Gly Leu Asn Arg Tyr Leu Thr Ile
 65                  70                  75                  80

Lys Asn Ile Gln Glu Glu Asp Glu Ser Asp Tyr His Cys Gly Ala Asp
                 85                  90                  95

His Gly Ser Gly Asn Asn Phe Val Tyr Val Phe Gly Thr Gly Thr Lys
            100                 105                 110

Val Thr Val Leu
        115

<210> SEQ ID NO 10
<211> LENGTH: 348
<212> TYPE: DNA
<213> ORGANISM: Homo sapiens

<400> SEQUENCE: 10
cagcctgtgc tgactcagcc accttctgca tcagcctccc tgggagcctc ggtcacactc       60
acctgcaccc tgagcagcgg ctacagtgat tataaagtgg actggtacca gcagagacca      120
gggaagggcc cccggtttgt gatgcgagtg ggcactggtg ggattgtggg atccaagggg      180
gaaggcatcc ctgatcgctt ctcagtcttg ggctcaggcc tgaatcggta cctgaccatc      240
aagaacatcc aggaagagga tgagagtgac taccactgtg ggcagaccat ggcagtgggg      300
aacaacttcg tgtatgtctt cggaactggg accaaggtca ccgtccta                   348

<210> SEQ ID NO 11
<211> LENGTH: 116
<212> TYPE: PRT
<213> ORGANISM: Homo sapiens

<400> SEQUENCE: 11

Gln Pro Glu Leu Thr Gln Pro Pro Ser Ala Ser Ala Ser Leu Gly Ala
  1               5                  10                  15

Ser Val Thr Leu Thr Cys Thr Leu Ser Ser Gly Tyr Ser Asp Tyr Lys
                 20                  25                  30

Val Asp Trp Tyr Gln Leu Arg Pro Gly Lys Gly Pro Arg Phe Val Met
             35                  40                  45

Arg Val Gly Thr Gly Gly Thr Val Gly Ser Lys Gly Glu Gly Ile Pro
 50                  55                  60

Asp Arg Phe Ser Val Leu Gly Ser Gly Leu Asn Arg Ser Leu Thr Ile
 65                  70                  75                  80

Lys Asn Ile Gln Glu Glu Asp Glu Ser Asp Tyr His Cys Gly Ala Asp
                 85                  90                  95

His Gly Ser Gly Ser Asn Phe Val Tyr Val Phe Gly Thr Gly Thr Lys
            100                 105                 110

Val Thr Val Leu
        115

<210> SEQ ID NO 12
<211> LENGTH: 348
<212> TYPE: DNA
<213> ORGANISM: Homo sapiens

<400> SEQUENCE: 12
cagcctgagt tgactcagcc accttctgca tcagcctccc tgggagcctc ggtcacactc       60
acctgcaccc tgagcagcgg ctacagtgat tataaagtgg actggtacca gctgagacca      120
gggaagggcc cccggtttgt gatgcgagtg ggcactggtg gaactgttgg atccaagggg      180
```

```
gaaggcatcc ctgatcgctt ctcagtcttg ggctcaggcc tgaatcggtc cctgaccatc    240
aagaacatcc aggaagagga tgagagtgac taccactgtg gggcagacca tggcagtggg    300
agcaacttcg tgtatgtctt cggaactggg accaaggtca ccgtccta                 348
```

<210> SEQ ID NO 13
<211> LENGTH: 107
<212> TYPE: PRT
<213> ORGANISM: Homo sapiens

<400> SEQUENCE: 13

```
Asp Ile Gln Leu Thr Pro Ser Pro Ser Val Ser Ala Ser Val Gly
1               5                   10                  15

Asp Arg Val Thr Ile Thr Cys Arg Ala Ser Gln Gly Ile Ala Gly Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Ser Phe Pro Pro
                85                  90                  95

Thr Phe Gly Gly Gly Thr Lys Val Glu Ile Lys
            100                 105
```

<210> SEQ ID NO 14
<211> LENGTH: 321
<212> TYPE: DNA
<213> ORGANISM: Homo sapiens

<400> SEQUENCE: 14

```
gacatccagt tgaccccgtc tccatcttcc gtgtctgcat ctgtaggaga cagagtcacc    60
atcacttgtc gggcgagtca gggtattgcc ggctggttag cctggtatca gcagaaacca    120
gggaaagccc ctaagctcct gatctatgct gcatccagtt tgcaaagtgg ggtcccatca    180
aggttcagcg gcagtggatc tgggacagat ttcactctca ccatcagcag cctgcagcct    240
gaagattttg caacttacta ttgtcaacag gctgacagtt tccctcccac tttcggcgga    300
gggaccaagg tggagatcaa a                                              321
```

<210> SEQ ID NO 15
<211> LENGTH: 107
<212> TYPE: PRT
<213> ORGANISM: Homo sapiens

<400> SEQUENCE: 15

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Val Ile Ser Ser Trp
            20                  25                  30

Leu Ala Trp Tyr Gln Gln Lys Pro Gly Lys Ala Pro Ser Leu Leu Ile
        35                  40                  45

Tyr Ala Ala Ser Ser Leu Gln Ser Gly Val Pro Ser Arg Phe Ser Gly
    50                  55                  60

Ser Val Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95
```

```
Thr Phe Gly Pro Gly Thr Lys Val Asp Phe Lys
            100                 105
```

<210> SEQ ID NO 16
<211> LENGTH: 321
<212> TYPE: DNA
<213> ORGANISM: Homo sapiens

<400> SEQUENCE: 16

```
gacatccaga tgacccagtc tccatcttcc gtgtctgcat ctgtaggaga cagagtcacc    60
atcacttgtc gggcgagtca ggttattagc agctggttag cctggtatca gcagaaacca   120
gggaaagccc ctagcctcct gatctatgct gcatccagtt tgcaaagtgg ggtcccatca   180
aggttcagcg gcagtgtatc tgggacagat tcactctcac catcagcag cctgcagcct   240
gaagattttg caacttacta ttgtcaacag gctaacagtt tcccattcac tttcggccct   300
gggaccaaag tggatttcaa a                                             321
```

<210> SEQ ID NO 17
<211> LENGTH: 107
<212> TYPE: PRT
<213> ORGANISM: Homo sapiens

<400> SEQUENCE: 17

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ser Ser Ser Trp
            20                  25                  30

Phe Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105
```

<210> SEQ ID NO 18
<211> LENGTH: 321
<212> TYPE: DNA
<213> ORGANISM: Homo sapiens

<400> SEQUENCE: 18

```
gacatccaga tgacccagtc tccatcttcc gtgtctgcat ctgtaggaga cagagtcacc    60
atcacttgtc gggcgagtca gggaagtagc agctggtttg cctggtatca gcagaaacca   120
gggaaagccc caaagctcct gatctatgct gcatccagtt tgcaaagtgg ggtcccatca   180
aggttcagcg gcagtggatc tgggacagac ttcactctca ccatcagcag cctgcagcct   240
gaagattttg caacttacta ttgtcaacag gctaacagtt tcccattcac tttcggccct   300
gggaccaaag tggatatcaa a                                             321
```

<210> SEQ ID NO 19
<211> LENGTH: 107
<212> TYPE: PRT
<213> ORGANISM: Homo sapiens

<400> SEQUENCE: 19

Asp Ser Gln Met Thr Gln Ser Pro Ser Val Ser Ala Ser Val Gly
1               5                   10                  15

Asp Arg Val Thr Ile Thr Cys Arg Ala Ser Gln Gly Ile Ser Ser Trp
            20                  25                  30

Phe Ala Trp Tyr Gln Gln Lys Pro Gly Gln Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65              70                  75                  80

Glu Asp Phe Ala Thr Tyr Tyr Cys Gln Gln Ala Asn Ser Phe Pro Phe
            85                  90                  95

Thr Phe Gly Pro Gly Thr Lys Val Asp Ile Lys
        100                 105

<210> SEQ ID NO 20
<211> LENGTH: 321
<212> TYPE: DNA
<213> ORGANISM: Homo sapiens

<400> SEQUENCE: 20
gacagccaga tgacccagtc tccatcttcc gtgtctgcct ctgtaggaga cagagtcacc      60
atcacttgtc gggcgagtca gggtattagc agctggtttg cctggtatca gcagaaacca    120
gggcaagccc ctaacctcct gatctatgct gcatccagtt tgcaaagtgg ggtcccatca    180
aggttcagcg gcagtggatc tgggacagaa ttcactctca ccatcagcag cctgcagcct    240
gaagattttg caacttacta ttgtcaacag gctaacagtt tcccattcac tttcggccct    300
gggaccaaag tggatatcaa a                                              321

<210> SEQ ID NO 21
<211> LENGTH: 107
<212> TYPE: PRT
<213> ORGANISM: Homo sapiens

<400> SEQUENCE: 21

Asp Ile Gln Met Thr Gln Ser Pro Ser Ser Val Ser Ala Ser Val Gly
1               5                   10                  15

Asp Arg Val Thr Ile Thr Cys Arg Ala Gly Gln Val Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Asp Asp Phe Ala Thr Tyr Tyr Cys Gln Gln Ala Thr Ser Phe Pro Leu
            85                  90                  95

Thr Phe Gly Gly Gly Thr Lys Val Glu Ile Lys
        100                 105

<210> SEQ ID NO 22
<211> LENGTH: 321
<212> TYPE: DNA
<213> ORGANISM: Homo sapiens

<400> SEQUENCE: 22
gacatccaga tgacccagtc tccatcttcc gtgtctgcat ctgtaggaga cagagtcacc      60

```
atcacttgtc gggcgggtca ggttattagc agctggttag cctggtatca gcagaaacca    120
gggaaagccc ctaagctcct gatctatgct gcatccagtt tgcaaagtgg ggtcccatcg    180
aggttcagcg gcagtggatc tgggacagat tcactctcac ccatcagcag cctgcagcct    240
gacgattttg caacttacta ttgtcaacag gctaccagtt ttcccctcac tttcggcgga    300
gggaccaagg tggagatcaa a    321
```

```
<210> SEQ ID NO 23
<211> LENGTH: 107
<212> TYPE: PRT
<213> ORGANISM: Homo sapiens

<400> SEQUENCE: 23
```

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Phe Ser Gly Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105
```

```
<210> SEQ ID NO 24
<211> LENGTH: 321
<212> TYPE: DNA
<213> ORGANISM: Homo sapiens

<400> SEQUENCE: 24
gacatccaga tgacccagtc tccatcttcc gtgtctgcat ctgtaggaga cagagtcacc     60
atcacttgtc gggcgagtca gggttttagc ggttggttag cctggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag cctgcagcct    240
gaagattttg caacttacta ctgtcaacag gctaacagtt tcccattcac tttcggccct    300
gggaccaaag tggatatcaa a    321
```

```
<210> SEQ ID NO 25
<211> LENGTH: 107
<212> TYPE: PRT
<213> ORGANISM: Homo sapiens

<400> SEQUENCE: 25
```

```
Asp Ile Gln Leu Thr Gln Ser Pro Ser Ser Val Ser Ala Ser Val Gly
 1               5                  10                  15

Asp Arg Val Thr Ile Thr Cys Arg Ala Ser Gln Val Ile Ser Ser Trp
            20                  25                  30

Phe Ala Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Ala Asp Phe Ala Thr Tyr Phe Cys Gln Gln Ala Asn Ser Phe Pro Phe
                85                  90                  95

Thr Phe Gly Pro Gly Thr Lys Val Asp Val Lys
            100                 105

<210> SEQ ID NO 26
<211> LENGTH: 321
<212> TYPE: DNA
<213> ORGANISM: Homo sapiens

<400> SEQUENCE: 26
gacatccagt tgacccagtc tccatcttcc gtgtctgcat ctgtaggaga cagagtcacc    60
atcacttgtc gggcgagtca ggttattagc agctggtttg cctggtatca gcagaaacca   120
gggaaagccc ctaacctcct gatctatgct gcatccagtt tgcaaagtgg ggtcccatca   180
aggttcagcg gcagtggatc tgggacagat ttcactctca ccatcagcag cctgcagcct   240
gcagattttg caacttactt ttgtcaacag gctaacagtt tcccattcac tttcggccct   300
gggaccaaag tggatgtcaa a                                             321

<210> SEQ ID NO 27
<211> LENGTH: 107
<212> TYPE: PRT
<213> ORGANISM: Homo sapiens

<400> SEQUENCE: 27

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ser Ser Ser Trp
            20                  25                  30

Phe Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105

<210> SEQ ID NO 28
<211> LENGTH: 321
<212> TYPE: DNA
<213> ORGANISM: Homo sapiens

<400> SEQUENCE: 28
gacatccaga tgacccagtc tccatcttcc gtgtctgcat ctgtaggaga cagagtcacc    60
atcacttgtc gggcgagtca gggtagtagc agctggtttg cctggtatca acagaaacca   120
gggaaagccc caaagctcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt tcccattcac tttcggccct   300
gggaccaaag tggatatcaa a                                             321

<210> SEQ ID NO 29

```
<211> LENGTH: 107
<212> TYPE: PRT
<213> ORGANISM: Homo sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Thr Phe Gly Gln Gly Thr Lys Val Glu Ile Glu
            100                 105

<210> SEQ ID NO 30
<211> LENGTH: 108
<212> TYPE: PRT
<213> ORGANISM: Artificial
<220> FEATURE:
<223> OTHER INFORMATION: Consensus Sequence
<220> FEATURE:
<221> NAME/KEY: MISC_FEATURE
<222> LOCATION: (2)..(2)
<223> OTHER INFORMATION: Xaa can be Ile or Ser
<220> FEATURE:
<221> NAME/KEY: MISC_FEATURE
<222> LOCATION: (4)..(4)
<223> OTHER INFORMATION: Xaa can be Met or Leu
<220> FEATURE:
<221> NAME/KEY: MISC_FEATURE
<222> LOCATION: (29)..(29)
<223> OTHER INFORMATION: Xaa can be Gly or Val
<220> FEATURE:
<221> NAME/KEY: MISC_FEATURE
<222> LOCATION: (30)..(30)
<223> OTHER INFORMATION: Xaa can be Ser, Phe or Ile
<220> FEATURE:
<221> NAME/KEY: MISC_FEATURE
<222> LOCATION: (32)..(32)
<223> OTHER INFORMATION: Xaa can be Ser or Gly
<220> FEATURE:
<221> NAME/KEY: MISC_FEATURE
<222> LOCATION: (34)..(34)
<223> OTHER INFORMATION: Xaa can be Phe or Leu
<220> FEATURE:
<221> NAME/KEY: MISC_FEATURE
<222> LOCATION: (43)..(43)
<223> OTHER INFORMATION: Xaa can be Lys or Gln
<220> FEATURE:
<221> NAME/KEY: MISC_FEATURE
<222> LOCATION: (46)..(46)
<223> OTHER INFORMATION: Xaa can be Lys, Asn or Ser
<220> FEATURE:
<221> NAME/KEY: MISC_FEATURE
<222> LOCATION: (67)..(67)
<223> OTHER INFORMATION: Xaa can be Gly or Val
<220> FEATURE:
<221> NAME/KEY: MISC_FEATURE
<222> LOCATION: (71)..(71)
<223> OTHER INFORMATION: Xaa can be Asp or Glu
<220> FEATURE:
<221> NAME/KEY: MISC_FEATURE
<222> LOCATION: (82)..(82)
<223> OTHER INFORMATION: Xaa can be Glu or Ala
<220> FEATURE:
<221> NAME/KEY: MISC_FEATURE
```

```
<222> LOCATION: (88)..(88)
<223> OTHER INFORMATION: Xaa can be Tyr or Phe
<220> FEATURE:
<221> NAME/KEY: MISC_FEATURE
<222> LOCATION: (107)..(107)
<223> OTHER INFORMATION: Xaa can be Ile, Val or Phe

<400> SEQUENCE: 30

Asp Xaa Gln Xaa Thr Gln Ser Pro Ser Val Ser Ala Ser Val Gly
1               5                   10                  15

Asp Arg Val Thr Ile Thr Cys Arg Ala Ser Gln Gly Xaa Xaa Ser Xaa
                20                  25                  30

Trp Xaa Ala Trp Tyr Gln Gln Lys Pro Gly Xaa Ala Pro Xaa Leu Leu
            35                  40                  45

Ile Tyr Ala Ala Ser Ser Leu Gln Ser Gly Val Pro Ser Arg Phe Ser
        50                  55                  60

Gly Ser Xaa Ser Gly Thr Xaa Phe Thr Leu Thr Ile Ser Ser Leu Gln
65                  70                  75                  80

Pro Xaa Asp Phe Ala Thr Tyr Xaa Cys Gln Gln Ala Asn Ser Phe Pro
            85                  90                  95

Phe Thr Phe Gly Pro Gly Thr Lys Val Asp Xaa Lys
            100                 105

<210> SEQ ID NO 31
<211> LENGTH: 124
<212> TYPE: PRT
<213> ORGANISM: Homo sapiens

<400> SEQUENCE: 31

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Glu Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Gly Tyr Thr Ser Ser Trp Tyr Pro Ala Phe Asp
                100                 105                 110

Ile Trp Gly Gln Gly Thr Met Val Thr Val Ser Ser
        115                 120

<210> SEQ ID NO 32
<211> LENGTH: 372
<212> TYPE: DNA
<213> ORGANISM: Homo sapiens

<400> SEQUENCE: 32
caggtgcagc tggtggagtc tgggggaggc gtggtccagc ctggagggtc cctgagactc       60
tcctgtgcag cgtctggatt caccttcagt agctatggca tgcactgggt ccgccaggct      120
ccaggcaagg ggctggagtg ggtggcagtt atatggtatg atggaagtaa tgaatactat      180
gcagactccg tgaagggccg attcaccatc tccagagaca attccaagaa cacgctgtat      240
ctgcaaatga acagcctgag agccgaggac acggctgtgt attactgtgc gagagatcgg      300
```

```
gggtatacca gtagctggta ccctgatgct tttgatatct ggggccaagg gacaatggtc    360
accgtctctt ca                                                        372
```

<210> SEQ ID NO 33
<211> LENGTH: 124
<212> TYPE: PRT
<213> ORGANISM: Homo sapiens

<400> SEQUENCE: 33

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Ser Ser Ser Trp Tyr Pro Asp Ala Phe Asp
            100                 105                 110

Ile Trp Gly Gln Gly Thr Met Val Thr Val Ser Ser
        115                 120
```

<210> SEQ ID NO 34
<211> LENGTH: 121
<212> TYPE: PRT
<213> ORGANISM: Homo sapiens

<400> SEQUENCE: 34

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Phe Asp Gly Ser Leu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Thr Thr Leu Ser Gly Ser Tyr Phe Asp Tyr Trp Gly
            100                 105                 110

Gln Gly Thr Leu Val Thr Val Ser Ser
        115                 120
```

<210> SEQ ID NO 35
<211> LENGTH: 363
<212> TYPE: DNA
<213> ORGANISM: Homo sapiens

<400> SEQUENCE: 35

```
caggtgcagc tggtggagtc tgggggaggc gtggtccagc ctgggaggtc cctgagactc     60
tcctgtgcag cctctggatt caccttcagt agctatggca tgcactgggt ccgccaggct    120
```

-continued

```
ccaggcaagg ggctggagtg ggtggcagtt atatcatttg atggaagtct taaatactat    180
gcagactccg tgaagggccg attcaccatc tccagagaca attccaagaa cacctgtat    240 ctgcaaatga acagcctgag agctgaggac acggctgtgt attactgtgc gagagaacgg    300
actactttaa gtgggagcta ctttgactac tggggccagg gaaccctggt caccgtctcc    360
tca                                                                  363
```

<210> SEQ ID NO 36
<211> LENGTH: 121
<212> TYPE: PRT
<213> ORGANISM: Homo sapiens

<400> SEQUENCE: 36

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Leu
        35                  40                  45

Ser Val Ile Ser His Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Thr Thr Leu Ser Gly Ser Tyr Phe Asp Tyr Trp Gly
            100                 105                 110

Gln Gly Thr Leu Val Thr Val Ser Ser
        115                 120

<210> SEQ ID NO 37
<211> LENGTH: 363
<212> TYPE: DNA
<213> ORGANISM: Homo sapiens

<400> SEQUENCE: 37

```
caggtgcagc tggtggagtc tgggggaggc gtggtccagc ctgggaggtc cctgagactc     60
tcctgtgcag cctctggatt caccttcagt agctatgcca tgcactgggt ccgccaggct    120
ccaggcaagg ggctggagtg gttgtcagtt atatcacatg atggaagtat taaatactat    180
gcagactccg tgaagggccg attcaccatc tccagagaca attccaagaa cacgctgtat    240
ctgcaaatga acagcctgag agctgaggac acggctgtgt attactgtgc gagagaacgg    300
actactctaa gtgggagcta ctttgactac tggggccagg gaaccctggt caccgtctcc    360
tca                                                                  363
```

<210> SEQ ID NO 38
<211> LENGTH: 125
<212> TYPE: PRT
<213> ORGANISM: Homo sapiens

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Arg Ser Ser Thr Ile Tyr Ile Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Arg Ile Ala Ala Ala Gly Gly Phe His Tyr Tyr Tyr Ala Leu
                100                 105                 110

Asp Val Trp Gly Gln Gly Thr Thr Val Thr Val Ser Ser
        115                 120                 125

<210> SEQ ID NO 39
<211> LENGTH: 375
<212> TYPE: DNA
<213> ORGANISM: Homo sapiens

<400> SEQUENCE: 39
gaggtgcagc tggtggagtc tgggggaggc ctggtacagc ctggggggtc cctgagactc    60
tcctgtgcag cctctggatt caccttcagt agctatagta tgaactgggt ccgccaggct   120
ccagggaagg ggctggagtg ggtttcgtac attagtagta gtagtagtac catatacatc   180
gcagactctg tgaagggccg attcaccatc tccagagaca atgccaagaa ctcactgtat   240
ctgcaaatga acagcctgag agacgaagac acggctgtgt attactgtgc gagacggata   300
gcagcagctg gtgggttcca ctactactac gctttggacg tctggggcca agggaccacg   360
gtcaccgtct cctca                                                    375

<210> SEQ ID NO 40
<211> LENGTH: 125
<212> TYPE: PRT
<213> ORGANISM: Homo sapiens

<400> SEQUENCE: 40

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Tyr
                 20                  25                  30

Ser Met Asn Trp Val Arg Gln Ala Pro Gly Lys Gly Leu Glu Trp Val
             35                  40                  45

Ser Tyr Ile Ser Ser Ser Ser Thr Arg Tyr His Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Arg Ile Ala Ala Ala Gly Pro Trp Gly Tyr Tyr Tyr Ala Met
                100                 105                 110

Asp Val Trp Gly Gln Gly Thr Thr Val Thr Val Ser Ser
        115                 120                 125

<210> SEQ ID NO 41
<211> LENGTH: 375
<212> TYPE: DNA
<213> ORGANISM: Homo sapiens

<400> SEQUENCE: 41
gaggtgcagc tggtggagtc tgggggaggc ttggtacaac ctggggggtc cctgagactc    60

```
tcctgtgcag cctctggatt caccttcagt acctatagca tgaactgggt ccgccaggct      120
ccagggaagg ggctggagtg ggtttcatac attagtagca gtagtagtac cagataccac      180
gcagactctg tgaagggccg attcaccatc tccagagaca atgccaagaa ctcactgtat      240
ctgcaaatga acagcctgag agacgaggac acggctgtgt attactgtgc gagacgtata      300
gcagcagctg gtccgtgggg ctactactac gctatggacg tctggggcca agggaccacg      360
gtcaccgtct cctca                                                       375
```

<210> SEQ ID NO 42
<211> LENGTH: 125
<212> TYPE: PRT
<213> ORGANISM: Homo sapiens

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Ser Ser Phe
            20                  25                  30

Ser Met Asn Trp Val Arg Gln Ala Pro Gly Lys Gly Leu Glu Trp Val
        35                  40                  45

Ser Tyr Ile Ser Ser Arg Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Arg Ile Ala Ala Ala Gly Pro Trp Gly Tyr Tyr Tyr Ala Met
            100                 105                 110

Asp Val Trp Gly Gln Gly Thr Thr Val Thr Val Ser Ser
        115                 120                 125
```

<210> SEQ ID NO 43
<211> LENGTH: 375
<212> TYPE: DNA
<213> ORGANISM: Homo sapiens

<400> SEQUENCE: 43

```
gaggtgcagc tggtggagtc tgggggaggc ttggtacagc ctggggggtc cctgagactc       60
tcctgtgtag tctctggatt caccttcagt agttttagca tgaactgggt ccgccaggct      120
ccagggaagg ggctggagtg ggtttcatac attagtagtc gtagtagtac catatactac      180
gcagactctg tgaagggccg attcaccatc tccagagaca atgccaagaa ctcactgtat      240
ctgcaaatga acagcctgag agacgaggac acggctgtgt attattgtgc gagacgtata      300
gcagcagctg gtccgtgggg ctactactac gctatggacg tctggggcca agggaccacg      360
gtcaccgtct cctca                                                       375
```

<210> SEQ ID NO 44
<211> LENGTH: 118
<212> TYPE: PRT
<213> ORGANISM: Homo sapiens

<400> SEQUENCE: 44

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
            20                  25                  30
```

Tyr Trp Ser Trp Ile Arg Gln Pro Ala Gly Lys Gly Leu Glu Trp Ile
            35                  40                  45

Gly Leu Ile Tyr Thr Ser Gly Ser Thr Asn Tyr Asn Pro Ser Leu Lys
        50                  55                  60

Ser Arg Val Thr Met Ser Leu Asp Thr Ser Lys Asn Gln Phe Ser Leu
65                  70                  75                  80

Arg Leu Thr Ser Val Thr Ala Ala Asp Thr Ala Val Tyr Tyr Cys Ala
                85                  90                  95

Arg Asp Arg Gly Tyr Tyr Tyr Gly Val Asp Val Trp Gly Gln Gly Thr
            100                 105                 110

Thr Val Thr Val Ser Ser
        115

<210> SEQ ID NO 45
<211> LENGTH: 354
<212> TYPE: DNA
<213> ORGANISM: Homo sapiens

<400> SEQUENCE: 45
caggtgcagc tgcaggagtc gggcccagga ctggtgaagc cttcggagac cctgtccctc      60
acctgcactg tctctggtgg ctccatcagt acttactact ggagctggat ccggcagccc    120
gccgggaagg gactggagtg gattgggctt atctatacca gtgggagcac caactacaac    180
ccctccctca agagtcgagt caccatgtca ttagacacgt ccaagaacca gttctccctg    240
aggctgacct ctgtgaccgc cgcggacacg gccgtttatt actgtgcgag agatcgtggg    300
tactactacg gtgtggacgt ctggggccag gggaccacgg tcaccgtctc ctca          354

<210> SEQ ID NO 46
<211> LENGTH: 120
<212> TYPE: PRT
<213> ORGANISM: Homo sapiens

<400> SEQUENCE: 46

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly His Ile His Tyr Ser Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Lys Asn Arg Gly Phe Tyr Tyr Gly Met Asp Val Trp Gly Gln
            100                 105                 110

Gly Thr Thr Val Thr Val Ser Ser
        115                 120

<210> SEQ ID NO 47
<211> LENGTH: 360
<212> TYPE: DNA
<213> ORGANISM: Homo sapiens

<400> SEQUENCE: 47
caggtgcagc tgcaggagtc gggcccagga ctggtgaagc cttcacagac cctgtccctc      60

```
acctgcactg tctctggtgg ctccatcagc agtggtggtt actactggag ctggatccgc    120
cagcacccag ggaagggcct ggagtggatt gggcacatcc attacagtgg aacacctac    180 tacaacccgt ccctcaagag tcgagttacc atatcagtag acacgtctaa gaatcagttc    240
tccctgaaac tgagctctgt gactgccgcg gacacggccg tgtattactg tgcgaaaaat    300
cgcgggttct actacggtat ggacgtctgg ggccaaggga ccacggtcac cgtctcctca    360
```

<210> SEQ ID NO 48
<211> LENGTH: 120
<212> TYPE: PRT
<213> ORGANISM: Homo sapiens

<400> SEQUENCE: 48

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Ser Tyr Tyr Asn Pro Ser
    50                  55                  60

Leu Lys Ser Arg Val Thr Ile Ser Val Asp Thr Ser Gln Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Gly His Tyr Tyr Gly Met Asp Val Trp Gly Gln
            100                 105                 110

Gly Thr Thr Val Thr Val Ser Ser
        115                 120
```

<210> SEQ ID NO 49
<211> LENGTH: 360
<212> TYPE: DNA
<213> ORGANISM: Homo sapiens

<400> SEQUENCE: 49

```
caggtgcagc tgcaggagtc gggcccagga ctggtgaagc cttcacagac cctgtccctc     60
acctgcactg tctctggtgg ctccatcaac agtggtggtt actactggag ctggatccgc    120
cagcacccag ggaagggcct ggagtggatt gggtacatct attacagtgg gagctcctac    180
tacaacccgt ccctcaagag tcgagttacc atatcagtag acacgtctca gaaccagttc    240
tccctgaagc tgagctctgt gactgccgcg gacacggccg tgtattactg tgcgagagat    300
cgggggcact actacggtat ggacgtctgg ggccaaggga ccacggtcac cgtctcctca    360
```

<210> SEQ ID NO 50
<211> LENGTH: 120
<212> TYPE: PRT
<213> ORGANISM: Homo sapiens

<400> SEQUENCE: 50

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
```

```
                      50                  55                  60
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Arg Gly His Tyr Tyr Gly Met Asp Val Trp Gly Gln
                100                 105                 110

Gly Thr Thr Val Thr Val Ser Ser
        115                 120

<210> SEQ ID NO 51
<211> LENGTH: 360
<212> TYPE: DNA
<213> ORGANISM: Homo sapiens

<400> SEQUENCE: 51
caggtgcagc tgcaggagtc gggcccagga ctggtgaagc cttcacagac cctgtccctc      60
acctgcactg tctctggtgg ctccatcagt agtggtggtt actactggag ctggatccgc     120
cagcacccag ggaagggcct ggagtggatt gggtacattt attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagat     300
cggggccact actatggaat ggacgtctgg ggccaaggga ccacggtcac cgtctcctca     360

<210> SEQ ID NO 52
<211> LENGTH: 118
<212> TYPE: PRT
<213> ORGANISM: Homo sapiens

<400> SEQUENCE: 52

Gln Val Gln Leu Gln Glu Ser Gly Pro Arg Leu Val Lys Pro Ser Glu
 1               5                  10                  15

Thr Leu Ser Leu Thr Cys Thr Val Ser Gly Asp Ser Ile Ser Ser Tyr
                20                  25                  30

Phe Trp Ser Trp Ile Arg Gln Pro Pro Gly Lys Gly Leu Glu Trp Leu
            35                  40                  45

Gly Tyr Ile Tyr Tyr Ser Gly Ser Thr Asn Tyr Asn Pro Ser Leu Lys
        50                  55                  60

Ser Arg Val Thr Ile Ser Ile Asp Thr Ser Lys Asn Gln Phe Ser Leu
 65                  70                  75                  80

Lys Leu Ser Ser Val Thr Ala Ala Asp Thr Ala Val Tyr Tyr Cys Thr
                 85                  90                  95

Arg Asp Arg Gly Ser Tyr Tyr Gly Ser Asp Tyr Trp Gly Gln Gly Thr
                100                 105                 110

Leu Val Thr Val Ser Ser
        115

<210> SEQ ID NO 53
<211> LENGTH: 354
<212> TYPE: DNA
<213> ORGANISM: Homo sapiens

<400> SEQUENCE: 53
caggtgcagc tgcaggagtc gggcccaaga ctggtgaagc cttcggagac cctgtccctc      60
acctgcactg tctctggtga ctccatcagt agttacttct ggagctggat ccggcagccc     120
ccagggaagg gactggagtg gcttgggtat atctattaca gtgggagcac caactacaac     180
```

```
ccctccctca agagtcgagt caccatatca atagacacgt ccaagaacca gttctccctg    240
aagctgagct ctgtgaccgc tgcggacacg gccgtgtatt actgtacgag agatcggggg    300
agctactacg gatctgacta ctggggccag ggaaccctgg tcaccgtctc ctca          354
```

<210> SEQ ID NO 54
<211> LENGTH: 120
<212> TYPE: PRT
<213> ORGANISM: Homo sapiens

<400> SEQUENCE: 54

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Thr Trp Ile Arg Gln His Pro Gly Lys Gly Leu Glu
        35                  40                  45

Trp Ile Gly Tyr Ile Tyr Tyr Ser Gly Asn Thr Tyr Tyr Asn Pro Ser
    50                  55                  60

Leu Lys Ser Arg Ile Thr Ile Ser Val Asp Thr Ser Lys Asn Gln Phe
65                  70                  75                  80

Ser Leu Ser Leu Ser Ser Val Thr Ala Ala Asp Thr Ala Val Tyr Tyr
                85                  90                  95

Cys Ala Arg Asn Arg Gly Tyr Tyr Tyr Gly Met Asp Val Trp Gly Gln
            100                 105                 110

Gly Thr Thr Val Thr Val Ser Ser
        115                 120
```

<210> SEQ ID NO 55
<211> LENGTH: 360
<212> TYPE: DNA
<213> ORGANISM: Homo sapiens

<400> SEQUENCE: 55

```
caggtgcagc tgcaggagtc gggcccagga ctggtgaagc cttcacagac cctgtccctc     60
acctgcactg tctctggtgg ctccatcagc agtggtggtt actactggac ctggatccgc    120
cagcacccag ggaagggcct ggagtggatt gggtacatct attacagtgg aacacctac     180 tacaacccgt ccctcaagag tcgaattacc atatcagtgg acacgtctaa gaaccagttc    240
tccctgagcc tgagctctgt gactgccgcg gacacggccg tgtattactg tgcgagaaat    300
cgcgggtact actacggtat ggacgtctgg ggccaaggga ccacggtcac cgtctcctca    360
```

<210> SEQ ID NO 56
<211> LENGTH: 120
<212> TYPE: PRT
<213> ORGANISM: Homo sapiens

<400> SEQUENCE: 56

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Met Ser Val Asp Thr Ser Lys Asn Gln Phe
65                  70                  75                  80
```

Ser Leu Lys Leu Ser Ser Val Thr Ala Ala Asp Thr Ala Val Tyr Tyr
            85                  90                  95

Cys Ala Lys Asn Arg Gly Phe Tyr Tyr Gly Met Asp Val Trp Gly Gln
            100                 105                 110

Gly Thr Thr Val Thr Val Ser Ser
        115                 120

<210> SEQ ID NO 57
<211> LENGTH: 360
<212> TYPE: DNA
<213> ORGANISM: Homo sapiens

<400> SEQUENCE: 57
caggtgcagc tgcaggagtc gggcccagga ctggtgaagc cttcacagac cctgtccctc    60
acctgcactg tctctggtgg ctccatcagc agtggtggtt actactggag ctggatccgc   120
cagcacccag ggaagggcct ggagtggatt gggtacatct attacagtgg gagcacctac   180
tacaacccgt ccctcaagag tcgagttacc atgtcagtag acacgtctaa gaaccagttc   240
tccctgaaac tgagctctgt gactgccgcg gacacggccg tgtattactg tgcgaaaaat   300
cgcgggttct actacggtat ggacgtctgg ggccaaggga ccacggtcac cgtctcctca   360

<210> SEQ ID NO 58
<211> LENGTH: 120
<212> TYPE: PRT
<213> ORGANISM: Homo sapiens

<400> SEQUENCE: 58

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Ser Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Arg Gly His Tyr Tyr Gly Met Asp Val Trp Gly Gln
            100                 105                 110

Gly Thr Thr Val Thr Val Ser Ser
        115                 120

<210> SEQ ID NO 59
<211> LENGTH: 360
<212> TYPE: DNA
<213> ORGANISM: Homo sapiens

<400> SEQUENCE: 59
caggtgcagc tgcaggagtc gggcccagga ctggtgaagc cttcacagac cctgtccctc    60
acctgcactg tctctggtgg ctccatcaat agtggtggtt actactggag ctggatccgc   120
cagcacccag ggaagggcct ggagtggatt gggtacatct attacagtgg gagcagctac   180
tacaacccgt ccctcaagag tcgagttacc atatcagttg acacgtctaa gaaccagttc   240
tccctgaagc tgagttctgt gactgccgcg gacacggccg tgtattactg tgcgagagat   300

-continued

```
cgggggcact actacggtat ggacgtctgg ggccaaggga ccacggtcac cgtctcctca    360
```

<210> SEQ ID NO 60
<211> LENGTH: 123
<212> TYPE: PRT
<213> ORGANISM: Homo sapiens

<400> SEQUENCE: 60

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Thr Val Thr Ile Tyr Tyr Asn Tyr Gly Met Asp Val
            100                 105                 110

Trp Gly Gln Gly Thr Thr Val Thr Val Ser Ser
        115                 120
```

<210> SEQ ID NO 61
<211> LENGTH: 116
<212> TYPE: PRT
<213> ORGANISM: Artificial
<220> FEATURE:
<223> OTHER INFORMATION: Consensus Sequence
<220> FEATURE:
<221> NAME/KEY: MISC_FEATURE
<222> LOCATION: (3)..(3)
<223> OTHER INFORMATION: Xaa can be Val or Glu
<220> FEATURE:
<221> NAME/KEY: MISC_FEATURE
<222> LOCATION: (25)..(25)
<223> OTHER INFORMATION: Xaa can be Asn or Ser
<220> FEATURE:
<221> NAME/KEY: MISC_FEATURE
<222> LOCATION: (38)..(38)
<223> OTHER INFORMATION: Xaa can be Gln or Leu
<220> FEATURE:
<221> NAME/KEY: MISC_FEATURE
<222> LOCATION: (55)..(55)
<223> OTHER INFORMATION: Xaa can be Ile or Thr
<220> FEATURE:
<221> NAME/KEY: MISC_FEATURE
<222> LOCATION: (61)..(61)
<223> OTHER INFORMATION: Xaa can be Asp or Glu
<220> FEATURE:
<221> NAME/KEY: MISC_FEATURE
<222> LOCATION: (77)..(77)
<223> OTHER INFORMATION: Xaa can be Tyr or Ser
<220> FEATURE:
<221> NAME/KEY: MISC_FEATURE
<222> LOCATION: (101)..(101)
<223> OTHER INFORMATION: Xaa can be Ser or Asn

<400> SEQUENCE: 61

```
Gln Pro Xaa Leu Thr Gln Pro Pro Ser Ala Ser Ala Ser Leu Gly Ala
1               5                   10                  15

Ser Val Thr Leu Thr Cys Thr Leu Xaa Ser Gly Tyr Ser Asp Tyr Lys
            20                  25                  30

Val Asp Trp Tyr Gln Xaa Arg Pro Gly Lys Gly Pro Arg Phe Val Met
        35                  40                  45
```

```
Arg Val Gly Thr Gly Gly Xaa Val Gly Ser Lys Gly Xaa Gly Ile Pro
    50                  55                  60
Asp Arg Phe Ser Val Leu Gly Ser Gly Leu Asn Arg Xaa Leu Thr Ile
65                  70                  75                  80
Lys Asn Ile Gln Glu Glu Asp Glu Ser Asp Tyr His Cys Gly Ala Asp
                85                  90                  95
His Gly Ser Gly Xaa Asn Phe Val Tyr Val Phe Gly Thr Gly Thr Lys
            100                 105                 110
Val Thr Val Leu
        115

<210> SEQ ID NO 62
<211> LENGTH: 14
<212> TYPE: PRT
<213> ORGANISM: Homo sapiens

<400> SEQUENCE: 62

Thr Gly Ser Ser Ser Asn Thr Gly Ala Gly Tyr Asp Val His
1               5                   10

<210> SEQ ID NO 63
<211> LENGTH: 7
<212> TYPE: PRT
<213> ORGANISM: Homo sapiens

<400> SEQUENCE: 63

Gly Ser Gly Asn Arg Pro Ser
1               5

<210> SEQ ID NO 64
<211> LENGTH: 11
<212> TYPE: PRT
<213> ORGANISM: Homo sapiens

<400> SEQUENCE: 64

Gln Ser Tyr Asp Ser Ser Leu Ser Gly Trp Val
1               5                   10

<210> SEQ ID NO 65
<211> LENGTH: 14
<212> TYPE: PRT
<213> ORGANISM: Homo sapiens

<400> SEQUENCE: 65

Thr Gly Ser Ser Ser Asn Ile Gly Ala Gly Tyr Asp Val His
1               5                   10

<210> SEQ ID NO 66
<211> LENGTH: 7
<212> TYPE: PRT
<213> ORGANISM: Homo sapiens

<400> SEQUENCE: 66

Gly Ser Asn Asn Arg Pro Ser
1               5

<210> SEQ ID NO 67
<211> LENGTH: 9
<212> TYPE: PRT
<213> ORGANISM: Homo sapiens

<400> SEQUENCE: 67

Met Ile Trp His Ser Ser Ala Ser Val
```

```
<210> SEQ ID NO 68
<211> LENGTH: 14
<212> TYPE: PRT
<213> ORGANISM: Homo sapiens

<400> SEQUENCE: 68

Thr Leu Arg Ser Gly Ile Asn Val Gly Thr Tyr Arg Ile Tyr
1               5                   10

<210> SEQ ID NO 69
<211> LENGTH: 11
<212> TYPE: PRT
<213> ORGANISM: Homo sapiens

<400> SEQUENCE: 69

Tyr Lys Ser Asp Ser Asp Lys Gln Gln Gly Ser
1               5                   10

<210> SEQ ID NO 70
<211> LENGTH: 13
<212> TYPE: PRT
<213> ORGANISM: Homo sapiens

<400> SEQUENCE: 70

Gly Ala Asp His Gly Ser Gly Ser Asn Phe Val Tyr Val
1               5                   10

<210> SEQ ID NO 71
<211> LENGTH: 11
<212> TYPE: PRT
<213> ORGANISM: Homo sapiens

<400> SEQUENCE: 71

Thr Leu Asn Ser Gly Tyr Ser Asp Tyr Lys Val
1               5                   10

<210> SEQ ID NO 72
<211> LENGTH: 12
<212> TYPE: PRT
<213> ORGANISM: Homo sapiens

<400> SEQUENCE: 72

Val Gly Thr Gly Gly Ile Val Gly Ser Lys Gly Asp
1               5                   10

<210> SEQ ID NO 73
<211> LENGTH: 13
<212> TYPE: PRT
<213> ORGANISM: Homo sapiens

<400> SEQUENCE: 73

Gly Ala Asp His Gly Ser Gly Asn Asn Phe Val Tyr Val
1               5                   10

<210> SEQ ID NO 74
<211> LENGTH: 11
<212> TYPE: PRT
<213> ORGANISM: Homo sapiens

<400> SEQUENCE: 74

Thr Leu Ser Ser Gly Tyr Ser Asp Tyr Lys Val
1               5                   10
```

```
<210> SEQ ID NO 75
<211> LENGTH: 12
<212> TYPE: PRT
<213> ORGANISM: Homo sapiens

<400> SEQUENCE: 75

Val Gly Thr Gly Gly Ile Val Gly Ser Lys Gly Glu
1               5                   10

<210> SEQ ID NO 76
<211> LENGTH: 9
<212> TYPE: PRT
<213> ORGANISM: Homo sapiens

<400> SEQUENCE: 76

Gln Gln Ala Asn Ser Phe Pro Phe Thr
1               5

<210> SEQ ID NO 77
<211> LENGTH: 11
<212> TYPE: PRT
<213> ORGANISM: Homo sapiens

<400> SEQUENCE: 77

Arg Ala Ser Gln Gly Phe Ser Gly Trp Leu Ala
1               5                   10

<210> SEQ ID NO 78
<211> LENGTH: 12
<212> TYPE: PRT
<213> ORGANISM: Homo sapiens

<400> SEQUENCE: 78

Val Gly Thr Gly Gly Thr Val Gly Ser Lys Gly Glu
1               5                   10

<210> SEQ ID NO 79
<211> LENGTH: 9
<212> TYPE: PRT
<213> ORGANISM: Homo sapiens

<400> SEQUENCE: 79

Gln Gln Ala Thr Ser Phe Pro Leu Thr
1               5

<210> SEQ ID NO 80
<211> LENGTH: 11
<212> TYPE: PRT
<213> ORGANISM: Homo sapiens

<400> SEQUENCE: 80

Arg Ala Ser Gln Val Ile Ser Ser Trp Leu Ala
1               5                   10

<210> SEQ ID NO 81
<211> LENGTH: 7
<212> TYPE: PRT
<213> ORGANISM: Homo sapiens

<400> SEQUENCE: 81

Ala Ala Ser Ser Leu Gln Ser
1               5

<210> SEQ ID NO 82
<211> LENGTH: 9
<212> TYPE: PRT
```

<213> ORGANISM: Homo sapiens

<400> SEQUENCE: 82

Gln Gln Ala Asp Ser Phe Pro Pro Thr
1               5

<210> SEQ ID NO 83
<211> LENGTH: 11
<212> TYPE: PRT
<213> ORGANISM: Homo sapiens

<400> SEQUENCE: 83

Arg Ala Ser Gln Val Ile Ser Ser Trp Phe Ala
1               5                   10

<210> SEQ ID NO 84
<211> LENGTH: 9
<212> TYPE: PRT
<213> ORGANISM: Homo sapiens

<400> SEQUENCE: 84

Leu Gln His Asn Ser Tyr Pro Pro Thr
1               5

<210> SEQ ID NO 85
<211> LENGTH: 11
<212> TYPE: PRT
<213> ORGANISM: Homo sapiens

<400> SEQUENCE: 85

Arg Ala Ser Gln Gly Ser Ser Trp Phe Ala
1               5                   10

<210> SEQ ID NO 86
<211> LENGTH: 11
<212> TYPE: PRT
<213> ORGANISM: Homo sapiens

<400> SEQUENCE: 86

Arg Ala Ser Gln Gly Ile Ser Ser Trp Phe Ala
1               5                   10

<210> SEQ ID NO 87
<211> LENGTH: 11
<212> TYPE: PRT
<213> ORGANISM: Homo sapiens

<400> SEQUENCE: 87

Arg Ala Gly Gln Val Ile Ser Ser Trp Leu Ala
1               5                   10

<210> SEQ ID NO 88
<211> LENGTH: 11
<212> TYPE: PRT
<213> ORGANISM: Homo sapiens

<400> SEQUENCE: 88

Arg Ala Ser Gln Gly Ile Ala Gly Trp Leu Ala
1               5                   10

<210> SEQ ID NO 89
<211> LENGTH: 11
<212> TYPE: PRT
<213> ORGANISM: Homo sapiens

<400> SEQUENCE: 89

Arg Ala Ser Gln Gly Ile Arg Asn Asp Leu Gly
1               5                   10

<210> SEQ ID NO 90
<211> LENGTH: 17
<212> TYPE: PRT
<213> ORGANISM: Homo sapiens

<400> SEQUENCE: 90

Leu Ile Trp Tyr Asp Gly Ser Asn Lys Tyr Tyr Ala Asp Ser Val Lys
1               5                   10                  15

Gly

<210> SEQ ID NO 91
<211> LENGTH: 5
<212> TYPE: PRT
<213> ORGANISM: Homo sapiens

<400> SEQUENCE: 91

Ser Tyr Gly Met His
1               5

<210> SEQ ID NO 92
<211> LENGTH: 17
<212> TYPE: PRT
<213> ORGANISM: Homo sapiens

<400> SEQUENCE: 92

Val Ile Trp Tyr Asp Gly Ser Asn Glu Tyr Tyr Ala Asp Ser Val Lys
1               5                   10                  15

Gly

<210> SEQ ID NO 93
<211> LENGTH: 15
<212> TYPE: PRT
<213> ORGANISM: Homo sapiens

<400> SEQUENCE: 93

Asp Arg Gly Tyr Thr Ser Ser Trp Tyr Pro Asp Ala Phe Asp Ile
1               5                   10                  15

<210> SEQ ID NO 94
<211> LENGTH: 5
<212> TYPE: PRT
<213> ORGANISM: Homo sapiens

<400> SEQUENCE: 94

Ser Tyr Ala Met His
1               5

<210> SEQ ID NO 95
<211> LENGTH: 17
<212> TYPE: PRT
<213> ORGANISM: Homo sapiens

<400> SEQUENCE: 95

Val Ile Trp Tyr Asp Gly Ser Asn Lys Tyr Tyr Ala Asp Ser Val Lys
1               5                   10                  15

Gly

<210> SEQ ID NO 96
<211> LENGTH: 15
<212> TYPE: PRT

```
<213> ORGANISM: Homo sapiens

<400> SEQUENCE: 96

Asp Arg Gly Tyr Ser Ser Ser Trp Tyr Pro Asp Ala Phe Asp Ile
1               5                   10                  15

<210> SEQ ID NO 97
<211> LENGTH: 5
<212> TYPE: PRT
<213> ORGANISM: Homo sapiens

<400> SEQUENCE: 97

Thr Tyr Ser Met Asn
1               5

<210> SEQ ID NO 98
<211> LENGTH: 17
<212> TYPE: PRT
<213> ORGANISM: Homo sapiens

<400> SEQUENCE: 98

Val Ile Ser Phe Asp Gly Ser Leu Lys Tyr Tyr Ala Asp Ser Val Lys
1               5                   10                  15

Gly

<210> SEQ ID NO 99
<211> LENGTH: 12
<212> TYPE: PRT
<213> ORGANISM: Homo sapiens

<400> SEQUENCE: 99

Glu Arg Thr Thr Leu Ser Gly Ser Tyr Phe Asp Tyr
1               5                   10

<210> SEQ ID NO 100
<211> LENGTH: 5
<212> TYPE: PRT
<213> ORGANISM: Homo sapiens

<400> SEQUENCE: 100

Ser Tyr Ser Met Asn
1               5

<210> SEQ ID NO 101
<211> LENGTH: 17
<212> TYPE: PRT
<213> ORGANISM: Homo sapiens

<400> SEQUENCE: 101

Val Ile Ser His Asp Gly Ser Ile Lys Tyr Tyr Ala Asp Ser Val Lys
1               5                   10                  15

Gly

<210> SEQ ID NO 102
<211> LENGTH: 16
<212> TYPE: PRT
<213> ORGANISM: Homo sapiens

<400> SEQUENCE: 102

Arg Ile Ala Ala Ala Gly Gly Phe His Tyr Tyr Tyr Ala Leu Asp Val
1               5                   10                  15

<210> SEQ ID NO 103
<211> LENGTH: 5
```

```
<212> TYPE: PRT
<213> ORGANISM: Homo sapiens

<400> SEQUENCE: 103

Ser Phe Ser Met Asn
1               5

<210> SEQ ID NO 104
<211> LENGTH: 17
<212> TYPE: PRT
<213> ORGANISM: Homo sapiens

<400> SEQUENCE: 104

Tyr Ile Ser Ser Arg Ser Ser Thr Ile Tyr Ile Ala Asp Ser Val Lys
1               5                   10                  15

Gly

<210> SEQ ID NO 105
<211> LENGTH: 16
<212> TYPE: PRT
<213> ORGANISM: Homo sapiens

<400> SEQUENCE: 105

Arg Ile Ala Ala Ala Gly Pro Trp Gly Tyr Tyr Ala Met Asp Val
1               5                   10                  15

<210> SEQ ID NO 106
<211> LENGTH: 7
<212> TYPE: PRT
<213> ORGANISM: Homo sapiens

<400> SEQUENCE: 106

Ser Gly Gly Tyr Tyr Trp Thr
1               5

<210> SEQ ID NO 107
<211> LENGTH: 17
<212> TYPE: PRT
<213> ORGANISM: Homo sapiens

<400> SEQUENCE: 107

Tyr Ile Ser Ser Ser Ser Thr Arg Tyr His Ala Asp Ser Val Lys
1               5                   10                  15

Gly

<210> SEQ ID NO 108
<211> LENGTH: 10
<212> TYPE: PRT
<213> ORGANISM: Homo sapiens

<400> SEQUENCE: 108

Asn Arg Gly Tyr Tyr Tyr Gly Met Asp Val
1               5                   10

<210> SEQ ID NO 109
<211> LENGTH: 7
<212> TYPE: PRT
<213> ORGANISM: Homo sapiens

<400> SEQUENCE: 109

Ser Gly Gly Tyr Tyr Trp Ser
1               5

<210> SEQ ID NO 110
```

-continued

```
<211> LENGTH: 17
<212> TYPE: PRT
<213> ORGANISM: Homo sapiens

<400> SEQUENCE: 110

Tyr Ile Ser Ser Arg Ser Ser Thr Ile Tyr Tyr Ala Asp Ser Val Lys
1               5                   10                  15

Gly

<210> SEQ ID NO 111
<211> LENGTH: 10
<212> TYPE: PRT
<213> ORGANISM: Homo sapiens

<400> SEQUENCE: 111

Asn Arg Gly Phe Tyr Tyr Gly Met Asp Val
1               5                   10

<210> SEQ ID NO 112
<211> LENGTH: 5
<212> TYPE: PRT
<213> ORGANISM: Homo sapiens

<400> SEQUENCE: 112

Ser Tyr Phe Trp Ser
1               5

<210> SEQ ID NO 113
<211> LENGTH: 16
<212> TYPE: PRT
<213> ORGANISM: Homo sapiens

<400> SEQUENCE: 113

Tyr Ile Tyr Tyr Ser Gly Asn Thr Tyr Tyr Asn Pro Ser Leu Lys Ser
1               5                   10                  15

<210> SEQ ID NO 114
<211> LENGTH: 10
<212> TYPE: PRT
<213> ORGANISM: Homo sapiens

<400> SEQUENCE: 114

Asp Arg Gly His Tyr Tyr Gly Met Asp Val
1               5                   10

<210> SEQ ID NO 115
<211> LENGTH: 5
<212> TYPE: PRT
<213> ORGANISM: Homo sapiens

<400> SEQUENCE: 115

Thr Tyr Tyr Trp Ser
1               5

<210> SEQ ID NO 116
<211> LENGTH: 16
<212> TYPE: PRT
<213> ORGANISM: Homo sapiens

<400> SEQUENCE: 116

His Ile His Tyr Ser Gly Asn Thr Tyr Tyr Asn Pro Ser Leu Lys Ser
1               5                   10                  15

<210> SEQ ID NO 117
<211> LENGTH: 10
```

```
<212> TYPE: PRT
<213> ORGANISM: Homo sapiens

<400> SEQUENCE: 117

Asp Arg Gly Ser Tyr Tyr Gly Ser Asp Tyr
1               5                   10

<210> SEQ ID NO 118
<211> LENGTH: 16
<212> TYPE: PRT
<213> ORGANISM: Homo sapiens

<400> SEQUENCE: 118

Tyr Ile Tyr Tyr Ser Gly Ser Thr Tyr Tyr Asn Pro Ser Leu Lys Ser
1               5                   10                  15

<210> SEQ ID NO 119
<211> LENGTH: 10
<212> TYPE: PRT
<213> ORGANISM: Homo sapiens

<400> SEQUENCE: 119

Asp Arg Gly Tyr Tyr Tyr Gly Val Asp Val
1               5                   10

<210> SEQ ID NO 120
<211> LENGTH: 16
<212> TYPE: PRT
<213> ORGANISM: Homo sapiens

<400> SEQUENCE: 120

Tyr Ile Tyr Tyr Ser Gly Ser Ser Tyr Tyr Asn Pro Ser Leu Lys Ser
1               5                   10                  15

<210> SEQ ID NO 121
<211> LENGTH: 16
<212> TYPE: PRT
<213> ORGANISM: Homo sapiens

<400> SEQUENCE: 121

Tyr Ile Tyr Tyr Ser Gly Ser Thr Asn Tyr Asn Pro Ser Leu Lys Ser
1               5                   10                  15

<210> SEQ ID NO 122
<211> LENGTH: 16
<212> TYPE: PRT
<213> ORGANISM: Homo sapiens

<400> SEQUENCE: 122

Leu Ile Tyr Thr Ser Gly Ser Thr Asn Tyr Asn Pro Ser Leu Lys Ser
1               5                   10                  15

<210> SEQ ID NO 123
<211> LENGTH: 11
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (5)..(5)
<223> OTHER INFORMATION: Xaa can be Gly or Val
<220> FEATURE:
<221> NAME/KEY: MISC_FEATURE
<222> LOCATION: (6)..(6)
<223> OTHER INFORMATION: Xaa can be Ile, Phe or Ser
<220> FEATURE:
<221> NAME/KEY: MISC_FEATURE
```

```
<222> LOCATION: (8)..(8)
<223> OTHER INFORMATION: Xaa can be Ser or Gly
<220> FEATURE:
<221> NAME/KEY: MISC_FEATURE
<222> LOCATION: (10)..(10)
<223> OTHER INFORMATION: Xaa can be  Phe or Leu.

<400> SEQUENCE: 123

Arg Ala Ser Gln Xaa Xaa Ser Xaa Trp Xaa Ala
1               5                   10

<210> SEQ ID NO 124
<211> LENGTH: 12
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (3)..(3)
<223> OTHER INFORMATION: Xaa can be Asn or Ser

<400> SEQUENCE: 124

Thr Leu Xaa Ser Gly Tyr Ser Asp Tyr Lys Val Asp
1               5                   10

<210> SEQ ID NO 125
<211> LENGTH: 14
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (7)..(7)
<223> OTHER INFORMATION: Xaa can be  Ile or Thr

<400> SEQUENCE: 125

Thr Gly Ser Ser Ser Asn Xaa Gly Ala Gly Tyr Asp Val His
1               5                   10

<210> SEQ ID NO 126
<211> LENGTH: 12
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (6)..(6)
<223> OTHER INFORMATION: Xaa can be Ile or Thr
<220> FEATURE:
<221> NAME/KEY: MISC_FEATURE
<222> LOCATION: (12)..(12)
<223> OTHER INFORMATION: Xaa can be Asp or Glu

<400> SEQUENCE: 126

Val Gly Thr Gly Gly Xaa Val Gly Ser Lys Gly Xaa
1               5                   10

<210> SEQ ID NO 127
<211> LENGTH: 7
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (3)..(3)
<223> OTHER INFORMATION: Xaa can be Asn or Gly

<400> SEQUENCE: 127
```

```
Gly Ser Xaa Asn Arg Pro Ser
1               5

<210> SEQ ID NO 128
<211> LENGTH: 13
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (8)..(8)
<223> OTHER INFORMATION: Xaa can be Ser or Asn

<400> SEQUENCE: 128

Gly Ala Asp His Gly Ser Gly Xaa Asn Phe Val Tyr Val
1               5                   10

<210> SEQ ID NO 129
<211> LENGTH: 7
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (7)..(7)
<223> OTHER INFORMATION: Xaa can be Ser or Thr

<400> SEQUENCE: 129

Ser Gly Gly Tyr Tyr Trp Xaa
1               5

<210> SEQ ID NO 130
<211> LENGTH: 5
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (3)..(3)
<223> OTHER INFORMATION: Xaa can be Gly or Ala

<400> SEQUENCE: 130

Ser Tyr Xaa Met His
1               5

<210> SEQ ID NO 131
<211> LENGTH: 5
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa can be Ser or Thr
<220> FEATURE:
<221> NAME/KEY: MISC_FEATURE
<222> LOCATION: (1)..(1)
<223> OTHER INFORMATION: Xaa can be Ser or Thr
<220> FEATURE:
<221> NAME/KEY: MISC_FEATURE
<222> LOCATION: (2)..(2)
<223> OTHER INFORMATION: Xaa can be Tyr or Phe

<400> SEQUENCE: 131

Xaa Xaa Ser Met Asn
1               5
```

```
<210> SEQ ID NO 132
<211> LENGTH: 16
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa can be Tyr or His
<220> FEATURE:
<221> NAME/KEY: MISC_FEATURE
<222> LOCATION: (3)..(3)
<223> OTHER INFORMATION: Xaa can be Thr or His
<220> FEATURE:
<221> NAME/KEY: MISC_FEATURE
<222> LOCATION: (7)..(7)
<223> OTHER INFORMATION: Xaa can be Ser or Asn
<220> FEATURE:
<221> NAME/KEY: MISC_FEATURE
<222> LOCATION: (8)..(8)
<223> OTHER INFORMATION: Xaa can be Thr or Ser

<400> SEQUENCE: 132

Xaa Ile Xaa Tyr Ser Gly Xaa Xaa Tyr Tyr Asn Pro Ser Leu Lys Ser
1               5                   10                  15

<210> SEQ ID NO 133
<211> LENGTH: 17
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (4)..(4)
<223> OTHER INFORMATION: Xaa can be Phe or His
<220> FEATURE:
<221> NAME/KEY: MISC_FEATURE
<222> LOCATION: (8)..(8)
<223> OTHER INFORMATION: Xaa can be Leu or Thr

<400> SEQUENCE: 133

Val Ile Ser Xaa Asp Gly Ser Xaa Lys Tyr Tyr Ala Asp Ser Val Lys
1               5                   10                  15

Gly

<210> SEQ ID NO 134
<211> LENGTH: 17
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (5)..(5)
<223> OTHER INFORMATION: Xaa can be Arg or Ser
<220> FEATURE:
<221> NAME/KEY: MISC_FEATURE
<222> LOCATION: (9)..(9)
<223> OTHER INFORMATION: Xaa can be Ile or Arg
<220> FEATURE:
<221> NAME/KEY: MISC_FEATURE
<222> LOCATION: (11)..(11)
<223> OTHER INFORMATION: Xaa can be Ile, His or Try

<400> SEQUENCE: 134

Tyr Ile Ser Ser Xaa Ser Ser Thr Xaa Tyr Xaa Ala Asp Ser Val Lys
1               5                   10                  15

Gly
```

```
<210> SEQ ID NO 135
<211> LENGTH: 17
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (9)..(9)
<223> OTHER INFORMATION: Xaa can be Lys or Glu

<400> SEQUENCE: 135

Val Ile Trp Tyr Asp Gly Ser Asn Xaa Tyr Tyr Ala Asp Ser Val Lys
1               5                   10                  15

Gly

<210> SEQ ID NO 136
<211> LENGTH: 10
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa can be Asn or Asp
<220> FEATURE:
<221> NAME/KEY: MISC_FEATURE
<222> LOCATION: (4)..(4)
<223> OTHER INFORMATION: Xaa can be His, Tyr or Phe

<400> SEQUENCE: 136

Xaa Arg Gly Xaa Tyr Tyr Gly Met Asp Val
1               5                   10

<210> SEQ ID NO 137
<211> LENGTH: 16
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (7)..(7)
<223> OTHER INFORMATION: Xaa can be Gly or Phe
<220> FEATURE:
<221> NAME/KEY: MISC_FEATURE
<222> LOCATION: (8)..(8)
<223> OTHER INFORMATION: Xaa can be Phe or Trp
<220> FEATURE:
<221> NAME/KEY: MISC_FEATURE
<222> LOCATION: (9)..(9)
<223> OTHER INFORMATION: Xaa can be His or Gly
<220> FEATURE:
<221> NAME/KEY: MISC_FEATURE
<222> LOCATION: (14)..(14)
<223> OTHER INFORMATION: Xaa can be Leu and Met

<400> SEQUENCE: 137

Arg Ile Ala Ala Ala Gly Xaa Xaa Xaa Tyr Tyr Tyr Ala Xaa Asp Val
1               5                   10                  15

<210> SEQ ID NO 138
<211> LENGTH: 15
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (5)..(5)
<223> OTHER INFORMATION: Xaa can be Ser or Thr
```

-continued

<400> SEQUENCE: 138

Asp Arg Gly Tyr Xaa Ser Ser Trp Tyr Pro Asp Ala Phe Asp Ile
1               5                   10                  15

<210> SEQ ID NO 139
<211> LENGTH: 112
<212> TYPE: PRT
<213> ORGANISM: Artificial
<220> FEATURE:
<223> OTHER INFORMATION: Consensus Sequence
<220> FEATURE:
<221> NAME/KEY: MISC_FEATURE
<222> LOCATION: (29)..(29)
<223> OTHER INFORMATION: Xaa can be Ile or Thr
<220> FEATURE:
<221> NAME/KEY: MISC_FEATURE
<222> LOCATION: (41)..(41)
<223> OTHER INFORMATION: Xaa can be Val or Leu
<220> FEATURE:
<221> NAME/KEY: MISC_FEATURE
<222> LOCATION: (54)..(54)
<223> OTHER INFORMATION: Xaa can be Gly or Asn
<220> FEATURE:
<221> NAME/KEY: MISC_FEATURE
<222> LOCATION: (107)..(107)
<223> OTHER INFORMATION: Xaa can be Arg or Lys

<400> SEQUENCE: 139

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Xaa Gly Ala Gly
                20                  25                  30

Tyr Asp Val His Trp Tyr Gln Gln Xaa Pro Gly Thr Ala Pro Lys Leu
            35                  40                  45

Leu Ile Tyr Gly Ser Xaa Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Val Phe Gly Gly Gly Thr Xaa Arg Leu Thr Val Leu
            100                 105                 110

<210> SEQ ID NO 140
<211> LENGTH: 120
<212> TYPE: PRT
<213> ORGANISM: Artificial
<220> FEATURE:
<223> OTHER INFORMATION: Consensus Sequence
<220> FEATURE:
<221> NAME/KEY: MISC_FEATURE
<222> LOCATION: (30)..(30)
<223> OTHER INFORMATION: Xaa can be And or Ser
<220> FEATURE:
<221> NAME/KEY: MISC_FEATURE
<222> LOCATION: (37)..(37)
<223> OTHER INFORMATION: Xaa can be Ser or Thr
<220> FEATURE:
<221> NAME/KEY: MISC_FEATURE
<222> LOCATION: (52)..(52)
<223> OTHER INFORMATION: Xaa can be Tyr or His
<220> FEATURE:
<221> NAME/KEY: MISC_FEATURE
<222> LOCATION: (54)..(54)
<223> OTHER INFORMATION: Xaa can be Tyr or His
<220> FEATURE:
<221> NAME/KEY: MISC_FEATURE
<222> LOCATION: (58)..(58)
<223> OTHER INFORMATION: Xaa can be Ser or Asn
<220> FEATURE:

```
<221> NAME/KEY: MISC_FEATURE
<222> LOCATION: (59)..(59)
<223> OTHER INFORMATION: Xaa can be Ser or Asn
<220> FEATURE:
<221> NAME/KEY: MISC_FEATURE
<222> LOCATION: (69)..(69)
<223> OTHER INFORMATION: Xaa can be Ser or Thr
<220> FEATURE:
<221> NAME/KEY: MISC_FEATURE
<222> LOCATION: (71)..(71)
<223> OTHER INFORMATION: Xaa can be Val or Ile
<220> FEATURE:
<221> NAME/KEY: MISC_FEATURE
<222> LOCATION: (77)..(77)
<223> OTHER INFORMATION: Xaa can be Ile or Met
<220> FEATURE:
<221> NAME/KEY: MISC_FEATURE
<222> LOCATION: (83)..(83)
<223> OTHER INFORMATION: Xaa can be Lys or Gln
<220> FEATURE:
<221> NAME/KEY: MISC_FEATURE
<222> LOCATION: (99)..(99)
<223> OTHER INFORMATION: Xaa can be Arg or Lys
<220> FEATURE:
<221> NAME/KEY: MISC_FEATURE
<222> LOCATION: (100)..(100)
<223> OTHER INFORMATION: Xaa can be Asp or Asn
<220> FEATURE:
<221> NAME/KEY: MISC_FEATURE
<222> LOCATION: (103)..(103)
<223> OTHER INFORMATION: Xaa can be His, Phe or Try

<400> SEQUENCE: 140

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Xaa Ser Gly
            20                  25                  30

Gly Tyr Tyr Trp Xaa Trp Ile Arg Gln His Pro Gly Lys Gly Leu Glu
        35                  40                  45

Trp Ile Gly Xaa Ile Xaa Tyr Ser Gly Xaa Xaa Tyr Tyr Asn Pro Ser
    50                  55                  60

Leu Lys Ser Arg Xaa Thr Xaa Ser Val Asp Thr Ser Xaa Asn Gln Phe
65                  70                  75                  80

Ser Leu Xaa Leu Ser Ser Val Thr Ala Ala Asp Thr Ala Val Tyr Tyr
            85                  90                  95

Cys Ala Xaa Xaa Arg Gly Xaa Tyr Tyr Gly Met Asp Val Trp Gly Gln
            100                 105                 110

Gly Thr Thr Val Thr Val Ser Ser
        115                 120

<210> SEQ ID NO 141
<211> LENGTH: 125
<212> TYPE: PRT
<213> ORGANISM: Artificial
<220> FEATURE:
<223> OTHER INFORMATION: Consensus Sequence
<220> FEATURE:
<221> NAME/KEY: MISC_FEATURE
<222> LOCATION: (23)..(23)
<223> OTHER INFORMATION: Xaa can be Ala or Val
<220> FEATURE:
<221> NAME/KEY: MISC_FEATURE
<222> LOCATION: (24)..(24)
<223> OTHER INFORMATION: Xaa can be Ala or Val
<220> FEATURE:
<221> NAME/KEY: MISC_FEATURE
<222> LOCATION: (31)..(31)
<223> OTHER INFORMATION: Xaa can be Thr or Ser
<220> FEATURE:
<221> NAME/KEY: MISC_FEATURE
<222> LOCATION: (32)..(32)
```

<223> OTHER INFORMATION: Xaa can be Tyr or Phe
<220> FEATURE:
<221> NAME/KEY: MISC_FEATURE
<222> LOCATION: (54)..(54)
<223> OTHER INFORMATION: Xaa can be Ser or Arg
<220> FEATURE:
<221> NAME/KEY: MISC_FEATURE
<222> LOCATION: (58)..(58)
<223> OTHER INFORMATION: Xaa can be Arg or Ile
<220> FEATURE:
<221> NAME/KEY: MISC_FEATURE
<222> LOCATION: (60)..(60)
<223> OTHER INFORMATION: Xaa can be His, Try or Ile
<220> FEATURE:
<221> NAME/KEY: MISC_FEATURE
<222> LOCATION: (105)..(105)
<223> OTHER INFORMATION: Xaa can be Pro or Gly
<220> FEATURE:
<221> NAME/KEY: MISC_FEATURE
<222> LOCATION: (106)..(106)
<223> OTHER INFORMATION: Xaa can be Trp or Phe
<220> FEATURE:
<221> NAME/KEY: MISC_FEATURE
<222> LOCATION: (107)..(107)
<223> OTHER INFORMATION: Xaa can be Gly or His
<220> FEATURE:
<221> NAME/KEY: MISC_FEATURE
<222> LOCATION: (112)..(112)
<223> OTHER INFORMATION: Xaa can be Met or Leu

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Xaa Xaa Ser Gly Phe Thr Phe Ser Xaa Xaa
            20                  25                  30

Ser Met Asn Trp Val Arg Gln Ala Pro Gly Lys Gly Leu Glu Trp Val
        35                  40                  45

Ser Tyr Ile Ser Ser Xaa Ser Ser Thr Xaa Tyr Xaa Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Arg Ile Ala Ala Ala Gly Xaa Xaa Xaa Tyr Tyr Tyr Ala Xaa
            100                 105                 110

Asp Val Trp Gly Gln Gly Thr Thr Val Thr Val Ser Ser
            115                 120                 125

<210> SEQ ID NO 142
<211> LENGTH: 121
<212> TYPE: PRT
<213> ORGANISM: Artificial
<220> FEATURE:
<223> OTHER INFORMATION: Consensus Sequence
<220> FEATURE:
<221> NAME/KEY: MISC_FEATURE
<222> LOCATION: (33)..(33)
<223> OTHER INFORMATION: Xaa can be Gly or Ala
<220> FEATURE:
<221> NAME/KEY: MISC_FEATURE
<222> LOCATION: (48)..(48)
<223> OTHER INFORMATION: Xaa can be Val or Leu
<220> FEATURE:
<221> NAME/KEY: MISC_FEATURE
<222> LOCATION: (49)..(49)
<223> OTHER INFORMATION: Xaa can be Ala or Ser
<220> FEATURE:
<221> NAME/KEY: MISC_FEATURE
<222> LOCATION: (53)..(53)
<223> OTHER INFORMATION: Xaa can be Phe or His
<220> FEATURE:

```
<221> NAME/KEY: MISC_FEATURE
<222> LOCATION: (57)..(57)
<223> OTHER INFORMATION: Xaa can be Leu or Ile

<400> SEQUENCE: 142
```

| | | | | | | | | | | | | | |
|---|---|---|---|---|---|---|---|---|---|---|---|---|---|
| Gln | Val | Gln | Leu | Val | Glu | Ser | Gly | Gly | Gly | Val | Val | Gln | Pro | Gly | Arg |
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |

| Xaa | Met | His | Trp | Val | Arg | Gln | Ala | Pro | Gly | Lys | Gly | Leu | Glu | Trp | Xaa |
| | | 35 | | | | | 40 | | | | | 45 | | | |

| Xaa | Val | Ile | Ser | Xaa | Asp | Gly | Ser | Xaa | Lys | Tyr | Tyr | Ala | Asp | Ser | Val |
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |

| Ala | Arg | Glu | Arg | Thr | Thr | Leu | Ser | Gly | Ser | Tyr | Phe | Asp | Tyr | Trp | Gly |
| | | | 100 | | | | | 105 | | | | | 110 | | |

| Gln | Gly | Thr | Leu | Val | Thr | Val | Ser | Ser |
| | | | 115 | | | | | 120 |

```
<210> SEQ ID NO 143
<211> LENGTH: 124
<212> TYPE: PRT
<213> ORGANISM: Artificial
<220> FEATURE:
<223> OTHER INFORMATION: Consensus Sequence
<220> FEATURE:
<221> NAME/KEY: MISC_FEATURE
<222> LOCATION: (58)..(58)
<223> OTHER INFORMATION: Xaa can be Glu or Lys
<220> FEATURE:
<221> NAME/KEY: MISC_FEATURE
<222> LOCATION: (103)..(103)
<223> OTHER INFORMATION: Xaa can be Thr or Ser

<400> SEQUENCE: 143
```

| Gln | Val | Gln | Leu | Val | Glu | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |

| Gly | Met | His | Trp | Val | Arg | Gln | Ala | Pro | Gly | Lys | Gly | Leu | Glu | Trp | Val |
| | | 35 | | | | | 40 | | | | | 45 | | | |

| Ala | Val | Ile | Trp | Tyr | Asp | Gly | Ser | Asn | Xaa | Tyr | Tyr | Ala | Asp | Ser | Val |
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |

| Ala | Arg | Asp | Arg | Gly | Tyr | Xaa | Ser | Ser | Trp | Tyr | Pro | Asp | Ala | Phe | Asp |
| | | | 100 | | | | | 105 | | | | | 110 | | |

| Ile | Trp | Gly | Gln | Gly | Thr | Met | Val | Thr | Val | Ser | Ser |
| | | | 115 | | | | | 120 | | | |

```
<210> SEQ ID NO 144
<211> LENGTH: 1026
<212> TYPE: DNA
<213> ORGANISM: Homo sapiens

<400> SEQUENCE: 144
```

```
aactcggtga caaactgagg gaaccaaacc agagacgcgc tgaacagaga gaatcaggct    60
caaagcaagt ggaagtgggc agagattcca ccaggactgg tgcaaggcgc agagccagcc   120
agatttgaga agaaggcaaa aagatgctgg ggagcagagc tgtaatgctg ctgttgctgc   180
tgccctggac agctcagggc agagctgtgc ctggggcag cagccctgcc tggactcagt    240
gccagcagct ttcacagaag ctctgcacac tggcctggag tgcacatcca ctagtgggac   300
acatggatct aagagaagag ggagatgaag agactacaaa tgatgttccc catatccagt   360
gtggagatgg ctgtgacccc caaggactca gggacaacag tcagttctgc ttgcaaagga   420
tccaccaggg tctgattttt tatgagaagc tgctaggatc ggatattttc acaggggagc   480
cttctctgct ccctgatagc cctgtgggcc agcttcatgc ctccctactg ggcctcagcc   540
aactcctgca gctgagggt caccactggg agactcagca gattccaagc ctcagtccca   600
gccagccatg gcagcgtctc cttctccgct tcaaaatcct tcgcagcctc caggcctttg   660
tggctgtagc cgcccgggtc tttgcccatg gagcagcaac cctgagtccc taaaggcagc   720
agctcaagga tggcactcag atctccatgg cccagcaagg ccaagataaa tctaccaccc   780
caggcacctg tgagccaaca ggttaattag tccattaatt ttagtgggac ctgcatatgt   840
tgaaaattac caatactgac tgacatgtga tgctgaccta tgataaggtt gagtatttat   900
tagatgggaa gggaaatttg gggattattt atcctcctgg ggacagtttg gggaggatta   960
tttattgtat ttatattgaa ttatgtactt ttttcaataa agtcttattt ttgtggctaa  1020
aaaaaa                                                             1026
```

<210> SEQ ID NO 145
<211> LENGTH: 189
<212> TYPE: PRT
<213> ORGANISM: Homo sapiens
<400> SEQUENCE: 145

```
Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185
```

<210> SEQ ID NO 146
<211> LENGTH: 1399
<212> TYPE: DNA
<213> ORGANISM: Homo sapiens

<400> SEQUENCE: 146

```
ctgtttcagg gccattggac tctccgtcct gcccagagca agatgtgtca ccagcagttg      60
gtcatctctt ggttttccct ggttttctg gcatctcccc tcgtggccat atgggaactg     120
aagaaagatg tttatgtcgt agaattggat tggtatccgg atgcccctgg agaaatggtg     180
gtcctcacct gtgacacccc tgaagaagat ggtatcacct ggaccttgga ccagagcagt     240
gaggtcttag gctctggcaa aaccctgacc atccaagtca aagagtttgg agatgctggc     300
cagtacacct gtcacaaagg aggcgaggtt ctaagccatt cgctcctgct gcttcacaaa     360
aaggaagatg gaatttggtc cactgatatt ttaaaggacc agaaagaacc caaaaataag     420
acctttctaa gatgcgaggc caagaattat tctggacgtt tcacctgctg gtggctgacg     480
acaatcagta ctgatttgac attcagtgtc aaaagcagca gaggctcttc tgacccccaa     540
ggggtgacgt gcggagctgc tacactctct gcagagagag tcagagggga caacaaggag     600
tatgagtact cagtggagtg ccaggaggac agtgcctgcc cagctgctga ggagagtctg     660
cccattgagg tcatggtgga tgccgttcac aagctcaagt atgaaaacta caccagcagc     720
ttcttcatca gggacatcat caaacctgac ccacccaaga acttgcagct gaagccatta     780
aagaattctc ggcaggtgga ggtcagctgg gagtaccctg acacctggag tactccacat     840
tcctacttct ccctgacatt ctgcgttcag gtccagggca agagcaagag agaaaagaaa     900
gatagagtct tcacggacaa gacctcagcc acggtcatct gccgcaaaaa tgccagcatt     960
agcgtgcggg cccaggaccg ctactatagc tcatcttgga gcgaatgggc atctgtgccc    1020
tgcagttagg ttctgatcca ggatgaaaat ttggaggaaa agtggaagat attaagcaaa    1080
atgtttaaag acacaacgga atagacccaa aaagataatt tctatctgat ttgctttaaa    1140
acgttttttt aggatcacaa tgatatcttt gctgtatttg tatagttaga tgctaaatgc    1200
tcattgaaac aatcagctaa tttatgtata gattttccag ctctcaagtt gccatgggcc    1260
ttcatgctat ttaaatattt aagtaattta tgtatttatt agtatattac tgttatttaa    1320
cgtttgtctg ccaggatgta tggaatgttt catactctta tgacctgatc catcaggatc    1380
agtccctatt atgcaaaat                                                 1399
```

<210> SEQ ID NO 147
<211> LENGTH: 328
<212> TYPE: PRT
<213> ORGANISM: Homo sapiens

<400> SEQUENCE: 147

```
Met Cys His Gln Gln Leu Val Ile Ser Trp Phe Ser Leu Val Phe Leu
  1               5                  10                  15

Ala Ser Pro Leu Val Ala Ile Trp Glu Leu Lys Lys Asp Val Tyr Val
                 20                  25                  30

Val Glu Leu Asp Trp Tyr Pro Asp Ala Pro Gly Glu Met Val Val Leu
             35                  40                  45

Thr Cys Asp Thr Pro Glu Glu Asp Gly Ile Thr Trp Thr Leu Asp Gln
         50                  55                  60

Ser Ser Glu Val Leu Gly Ser Gly Lys Thr Leu Thr Ile Gln Val Lys
 65                  70                  75                  80

Glu Phe Gly Asp Ala Gly Gln Tyr Thr Cys His Lys Gly Gly Glu Val
```

|  |  |  | 85 |  |  |  | 90 |  |  |  | 95 |  |
|--|--|--|--|--|--|--|--|--|--|--|--|--|

Leu Ser His Ser Leu Leu Leu His Lys Lys Glu Asp Gly Ile Trp
              100                    105                  110

Ser Thr Asp Ile Leu Lys Asp Gln Lys Glu Pro Lys Asn Lys Thr Phe
        115                    120                    125

Leu Arg Cys Glu Ala Lys Asn Tyr Ser Gly Arg Phe Thr Cys Trp Trp
130                    135                    140

Leu Thr Thr Ile Ser Thr Asp Leu Thr Phe Ser Val Lys Ser Ser Arg
145                  150                    155                    160

Gly Ser Ser Asp Pro Gln Gly Val Thr Cys Gly Ala Ala Thr Leu Ser
                165                    170                    175

Ala Glu Arg Val Arg Gly Asp Asn Lys Glu Tyr Glu Tyr Ser Val Glu
              180                    185                    190

Cys Gln Glu Asp Ser Ala Cys Pro Ala Ala Glu Glu Ser Leu Pro Ile
        195                    200                    205

Glu Val Met Val Asp Ala Val His Lys Leu Lys Tyr Glu Asn Tyr Thr
      210                    215                    220

Ser Ser Phe Phe Ile Arg Asp Ile Ile Lys Pro Asp Pro Pro Lys Asn
225                    230                    235                    240

Leu Gln Leu Lys Pro Leu Lys Asn Ser Arg Gln Val Glu Val Ser Trp
              245                    250                    255

Glu Tyr Pro Asp Thr Trp Ser Thr Pro His Ser Tyr Phe Ser Leu Thr
          260                    265                    270

Phe Cys Val Gln Val Gln Gly Lys Ser Lys Arg Glu Lys Lys Asp Arg
        275                    280                    285

Val Phe Thr Asp Lys Thr Ser Ala Thr Val Ile Cys Arg Lys Asn Ala
      290                    295                    300

Ser Ile Ser Val Arg Ala Gln Asp Arg Tyr Tyr Ser Ser Ser Trp Ser
305                    310                    315                    320

Glu Trp Ala Ser Val Pro Cys Ser
              325

```
<210> SEQ ID NO 148
<211> LENGTH: 2826
<212> TYPE: DNA
<213> ORGANISM: Homo sapiens

<400> SEQUENCE: 148
acaagggtgg cagcctggct ctgaagtgga attatgtgct tcaaacaggt tgaaagaggg      60
aaacagtctt ttcctgcttc cagacatgaa tcaggtcact attcaatggg atgcagtaat     120 agcccttta c atactcttca gctggtgtca tggaggaatt acaaatataa actgctctgg     180
ccacatctgg gtagaaccag ccacaatttt taagatgggt atgaatatct ctatatattg     240
ccaagcagca attaagaact gccaaccaag gaaacttcat ttttataaaa atggcatcaa     300
agaaagattt caaatcacaa ggattaataa acaacagct cggctttggt ataaaaactt      360
tctggaacca catgcttcta tgtactgcac tgctgaatgt cccaaacatt ttcaagagac     420
actgatatgt ggaaaagaca tttcttctgg atatccgcca gatattcctg atgaagtaac     480
ctgtgtcatt tatgaatatt caggcaacat gacttgcacc tggaatgctg gaagctcac     540 ctacatagac acaaaatacg tggtacatgt gaagagttta gagacagaag aagagcaaca     600
gtatctcacc tcaagctata ttaacatctc cactgattca ttacaaggtg caagaagta      660 cttggtttgg gtccaagcag caaacgcact aggcatggaa gagtcaaaac aactgcaaat     720
tcacctggat gatatagtga taccttctgc agccgtcatt tccagggctg agactataaa     780
```

```
tgctacagtg cccaagacca taatttattg ggatagtcaa acaacaattg aaaaggtttc    840
ctgtgaaatg agatacaagg ctacaacaaa ccaaacttgg aatgttaaag aatttgacac    900
caattttaca tatgtgcaac agtcagaatt ctacttggag ccaaacatta agtacgtatt    960
tcaagtgaga tgtcaagaaa caggcaaaag gtactggcag ccttggagtt cactgttttt   1020
tcataaaaca cctgaaacag ttccccaggt cacatcaaaa gcattccaac atgacacatg   1080
gaattctggg ctaacagttg cttccatctc tacagggcac cttacttctg acaacagagg   1140
agacattgga cttttattgg gaatgatcgt ctttgctgtt atgttgtcaa ttctttcttt   1200
gattgggata tttaacagat cattccgaac tgggattaaa agaaggatct tattgttaat   1260
accaaagtgg ctttatgaag atattcctaa tatgaaaaac agcaatgttg tgaaaatgct   1320
acaggaaaat agtgaactta tgaataataa ttccagtgag caggtcctat atgttgatcc   1380
catgattaca gagataaaag aaatcttcat cccagaacac aagcctacag actacaagaa   1440
ggagaataca ggacccctgg agacaagaga ctacccgcaa aactcgctat tcgacaatac   1500
tacagttgta tatattcctg atctcaacac tggatataaa ccccaaattt caaattttct   1560
gcctgaggga agccatctca gcaataataa tgaaattact tccttaacac ttaaaccacc   1620
agttgattcc ttagactcag gaaataatcc caggttacaa aagcatccta attttgcttt   1680
ttctgtttca agtgtgaatt cactaagcaa cacaatattt cttggagaat taagcctcat   1740
attaaatcaa ggagaatgca gttctcctga catacaaaac tcagtagagg aggaaaccac   1800
catgcttttg gaaaatgatt cacccagtga aactattcca gaacagaccc tgcttcctga   1860
tgaatttgtc tcctgtttgg ggatcgtgaa tgaggagttg ccatctatta atacttattt   1920
tccacaaaat attttgggaaa gccacttcaa taggatttca ctcttggaaa agtagagctg   1980
tgtggtcaaa atcaatatga gaaagctgcc ttgcaatctg aacttgggtt ttccctgcaa   2040
tagaaattga attctgcctc tttttgaaaa aaatgtattc acatacaaat cttcacatgg   2100
acacatgttt tcatttccct tggataaata cctaggtagg ggattgctgg gccatatgat   2160
aagcatatgt ttcagttcta ccaatcttgt ttccagagta gtgacatttc tgtgctccta   2220
ccatcaccat gtaagaattc ccgggagctc catgcctttt taattttagc cattcttctg   2280
cctcatttct taaaattaga gaattaaggt cccgaaggtg gaacatgctt catggtcaca   2340
catacaggca caaaacagc attatgtgga cgcctcatgt attttttata gagtcaacta    2400
tttcctcttt attttccctc attgaaagat gcaaaacagc tctctattgt gtacagaaag   2460
ggtaaataat gcaaatacc tggtagtaaa ataaatgctg aaaatttttcc tttaaaatag   2520 aatcattagg ccaggcgtgg tggctcatgc ttgtaatccc agcactttgg taggctgagg   2580
taggtggatc acctgaggtc aggagttcga gtccagcctg gccaatatgc tgaaaccctg   2640
tctctactaa aattacaaaa attagccggc catggtggca ggtgcttgta atcccagcta   2700
cttgggaggc tgaggcagga gaatcacttg aaccaggaag gcagaggttg cactgagctg   2760
agattgtgcc actgcactcc agcctgggca acaagagcaa aactctgtct ggaaaaaaaa   2820
aaaaaa                                                             2826
```

<210> SEQ ID NO 149
<211> LENGTH: 629
<212> TYPE: PRT
<213> ORGANISM: Homo sapiens

<400> SEQUENCE: 149

Met Asn Gln Val Thr Ile Gln Trp Asp Ala Val Ile Ala Leu Tyr Ile

-continued

```
1               5               10              15
Leu Phe Ser Trp Cys His Gly Gly Ile Thr Asn Ile Asn Cys Ser Gly
                20                  25                  30

His Ile Trp Val Glu Pro Ala Thr Ile Phe Lys Met Gly Met Asn Ile
                35                  40                  45

Ser Ile Tyr Cys Gln Ala Ala Ile Lys Asn Cys Gln Pro Arg Lys Leu
    50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
                100                 105                 110

Leu Ile Cys Gly Lys Asp Ile Ser Ser Gly Tyr Pro Pro Asp Ile Pro
                115                 120                 125

Asp Glu Val Thr Cys Val Ile Tyr Glu Tyr Ser Gly Asn Met Thr Cys
130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Gln Gln Tyr Leu Thr Ser
                165                 170                 175

Ser Tyr Ile Asn Ile Ser Thr Asp Ser Leu Gln Gly Gly Lys Lys Tyr
                180                 185                 190

Leu Val Trp Val Gln Ala Ala Asn Ala Leu Gly Met Glu Glu Ser Lys
                195                 200                 205

Gln Leu Gln Ile His Leu Asp Asp Ile Val Ile Pro Ser Ala Ala Val
    210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
                245                 250                 255

Tyr Lys Ala Thr Thr Asn Gln Thr Trp Asn Val Lys Glu Phe Asp Thr
                260                 265                 270

Asn Phe Thr Tyr Val Gln Gln Ser Glu Phe Tyr Leu Glu Pro Asn Ile
                275                 280                 285

Lys Tyr Val Phe Gln Val Arg Cys Gln Glu Thr Gly Lys Arg Tyr Trp
                290                 295                 300

Gln Pro Trp Ser Ser Leu Phe Phe His Lys Thr Pro Glu Thr Val Pro
305                 310                 315                 320

Gln Val Thr Ser Lys Ala Phe Gln His Asp Thr Trp Asn Ser Gly Leu
                325                 330                 335

Thr Val Ala Ser Ile Ser Thr Gly His Leu Thr Ser Asp Asn Arg Gly
                340                 345                 350

Asp Ile Gly Leu Leu Leu Gly Met Ile Val Phe Ala Val Met Leu Ser
                355                 360                 365

Ile Leu Ser Leu Ile Gly Ile Phe Asn Arg Ser Phe Arg Thr Gly Ile
                370                 375                 380

Lys Arg Arg Ile Leu Leu Leu Ile Pro Lys Trp Leu Tyr Glu Asp Ile
385                 390                 395                 400

Pro Asn Met Lys Asn Ser Asn Val Val Lys Met Leu Gln Glu Asn Ser
                405                 410                 415

Glu Leu Met Asn Asn Asn Ser Ser Glu Gln Val Leu Tyr Val Asp Pro
                420                 425                 430
```

```
Met Ile Thr Glu Ile Lys Glu Ile Phe Ile Pro Glu His Lys Pro Thr
        435                 440                 445
Asp Tyr Lys Lys Glu Asn Thr Gly Pro Leu Glu Thr Arg Asp Tyr Pro
450                 455                 460
Gln Asn Ser Leu Phe Asp Asn Thr Thr Val Val Tyr Ile Pro Asp Leu
465                 470                 475                 480
Asn Thr Gly Tyr Lys Pro Gln Ile Ser Asn Phe Leu Pro Glu Gly Ser
                485                 490                 495
His Leu Ser Asn Asn Glu Ile Thr Ser Leu Thr Leu Lys Pro Pro
            500                 505                 510
Val Asp Ser Leu Asp Ser Gly Asn Asn Pro Arg Leu Gln Lys His Pro
        515                 520                 525
Asn Phe Ala Phe Ser Val Ser Ser Val Asn Ser Leu Ser Asn Thr Ile
        530                 535                 540
Phe Leu Gly Glu Leu Ser Leu Ile Leu Asn Gln Gly Glu Cys Ser Ser
545                 550                 555                 560
Pro Asp Ile Gln Asn Ser Val Glu Glu Thr Thr Met Leu Leu Glu
                565                 570                 575
Asn Asp Ser Pro Ser Glu Thr Ile Pro Glu Gln Thr Leu Leu Pro Asp
            580                 585                 590
Glu Phe Val Ser Cys Leu Gly Ile Val Asn Glu Glu Leu Pro Ser Ile
        595                 600                 605
Asn Thr Tyr Phe Pro Gln Asn Ile Leu Glu Ser His Phe Asn Arg Ile
        610                 615                 620
Ser Leu Leu Glu Lys
625

<210> SEQ ID NO 150
<211> LENGTH: 2100
<212> TYPE: DNA
<213> ORGANISM: Homo sapiens

<400> SEQUENCE: 150
ggtggctgaa cctcgcaggt ggcagagagg ctcccctggg gctgtggggc tctacgtgga      60
tccgatggag ccgctggtga cctgggtggt ccccctcctc ttcctcttcc tgctgtccag     120
gcagggcgct gcctgcagaa ccagtgagtg ctgttttcag acccgccat atccggatgc     180 agactcaggc tcggcctcgg gccctaggga cctgagatgc tatcggatat ccagtgatcg     240
ttacgagtgc tcctggcagt atgagggtcc cacagctggg gtcagccact tcctgcggtg     300
ttgccttagc tccgggcgct gctgctactt cgccgccggc tcagccacca ggctgcagtt     360
ctccgaccag gctggggtgt ctgtgctgta cactgtcaca ctctgggtgg aatcctgggc     420
caggaaccag acagagaagt ctcctgaggt gaccctgcag ctctacaact cagttaaata     480
tgagcctcct ctgggagaca tcaaggtgtc caagttggcc gggcagctgc gtatggagtg     540
ggagaccccg gataaccagg ttggtgctga ggtgcagttc cggcaccgga cacccagcag     600
cccatggaag ttgggcgact gcggacctca ggatgatgat actgagtcct gcctctgccc     660
cctggagatg aatgtggccc aggaattcca gctccgacga cggcagctgg ggagccaagg     720
aagttcctgg agcaagtgga gcagccccgt gtgcgttccc cctgaaaacc ccccacagcc     780
tcaggtgaga ttctcggtgg agcagctggg ccaggatggg aggaggcggc tgaccctgaa     840
agagcagcca acccagctgg agcttccaga aggctgtcaa gggctggcgc tggcacgga     900 ggtcacttac cgactacagc tccacatgct gtcctgcccg tgtaaggcca aggccaccag     960
gaccctgcac ctggggaaga tgcctatct ctcgggtgct gcctacaacg tggctgtcat    1020
```

```
ctcctcgaac caatttggtc ctggcctgaa ccagacgtgg cacattcctg ccgacaccca    1080
cacagaacca gtggctctga atatcagcgt cggaaccaac gggaccacca tgtattggcc    1140
agcccgggct cagagcatga cgtattgcat tgaatggcag cctgtgggcc aggacggggg    1200
ccttgccacc tgcagcctga ctgcgccgca agacccggat ccggctggaa tggcaaccta    1260
cagctggagt cgagagtctg ggcaatgggg caggaaaag tgttactaca ttaccatctt    1320
tgcctctgcg caccccgaga agctcacctt gtggtctacg gtcctgtcca cctaccactt    1380
tgggggcaat gcctcagcag ctgggacacc gcaccacgtc tcggtgaaga atcatagctt    1440
ggactctgtg tctgtggact gggcaccatc cctgctgagc acctgtcccg gcgtcctaaa    1500
ggagtatgtt gtccgctgcc gagatgaaga cagcaaacag gtgtcagagc atcccgtgca    1560
gcccacagag acccaagtta ccctcagtgg cctgcgggct ggtgtagcct acacggtgca    1620
ggtgcgagca gacacagcgt ggctgagggg tgtctggagc cagccccagc gcttcagcat    1680
cgaagtgcag gtttctgatt ggctcatctt cttcgcctcc ctggggagct tcctgagcat    1740
ccttctcgtg ggcgtccttg gctaccttgg cctgaacagg gccgcacggc acctgtgccc    1800
gccgctgccc acaccctgtg ccagctccgc cattgagttc cctggaggga aggagacttg    1860
gcagtggatc aacccagtgg acttccagga agaggcatcc ctgcaggagg ccctggtggt    1920
agagatgtcc tgggacaaag gcgagaggac tgagcctctc gagaagacag agctacctga    1980
gggtgcccct gagctggccc tggatacaga gttgtccttg gaggatggag acaggtgcaa    2040
ggccaagatg tgatcgttga ggctcagaga gggtgagtga ctcgcccgag gctacgtagc    2100
```

<210> SEQ ID NO 151
<211> LENGTH: 662
<212> TYPE: PRT
<213> ORGANISM: Homo sapiens

<400> SEQUENCE: 151

Met Glu Pro Leu Val Thr Trp Val Val Pro Leu Leu Phe Leu Phe Leu
1               5                   10                  15

Leu Ser Arg Gln Gly Ala Ala Cys Arg Thr Ser Glu Cys Cys Phe Gln
            20                  25                  30

Asp Pro Tyr Pro Asp Ala Asp Ser Gly Ser Ala Ser Gly Pro Arg
        35                  40                  45

Asp Leu Arg Cys Tyr Arg Ile Ser Ser Asp Arg Tyr Glu Cys Ser Trp
    50                  55                  60

Gln Tyr Glu Gly Pro Thr Ala Gly Val Ser His Phe Leu Arg Cys Cys
65                  70                  75                  80

Leu Ser Ser Gly Arg Cys Cys Tyr Phe Ala Ala Gly Ser Ala Thr Arg
                85                  90                  95

Leu Gln Phe Ser Asp Gln Ala Gly Val Ser Val Leu Tyr Thr Val Thr
            100                 105                 110

Leu Trp Val Glu Ser Trp Ala Arg Asn Gln Thr Glu Lys Ser Pro Glu
        115                 120                 125

Val Thr Leu Gln Leu Tyr Asn Ser Val Lys Tyr Glu Pro Pro Leu Gly
    130                 135                 140

Asp Ile Lys Val Ser Lys Leu Ala Gly Gln Leu Arg Met Glu Trp Glu
145                 150                 155                 160

Thr Pro Asp Asn Gln Val Gly Ala Glu Val Gln Phe Arg His Arg Thr
                165                 170                 175

Pro Ser Ser Pro Trp Lys Leu Gly Asp Cys Gly Pro Gln Asp Asp Asp
            180                 185                 190

```
Thr Glu Ser Cys Leu Cys Pro Leu Glu Met Asn Val Ala Gln Glu Phe
            195                 200                 205

Gln Leu Arg Arg Arg Gln Leu Gly Ser Gln Gly Ser Ser Trp Ser Lys
        210                 215                 220

Trp Ser Pro Val Cys Val Pro Pro Glu Asn Pro Pro Gln Pro Gln
225                 230                 235                 240

Val Arg Phe Ser Val Glu Gln Leu Gly Gln Asp Gly Arg Arg Leu
                245                 250                 255

Thr Leu Lys Glu Gln Pro Thr Gln Leu Glu Leu Pro Glu Gly Cys Gln
            260                 265                 270

Gly Leu Ala Pro Gly Thr Glu Val Thr Tyr Arg Leu Gln Leu His Met
        275                 280                 285

Leu Ser Cys Pro Cys Lys Ala Lys Ala Thr Arg Thr Leu His Leu Gly
        290                 295                 300

Lys Met Pro Tyr Leu Ser Gly Ala Ala Tyr Asn Val Ala Val Ile Ser
305                 310                 315                 320

Ser Asn Gln Phe Gly Pro Gly Leu Asn Gln Thr Trp His Ile Pro Ala
                325                 330                 335

Asp Thr His Thr Glu Pro Val Ala Leu Asn Ile Ser Val Gly Thr Asn
            340                 345                 350

Gly Thr Thr Met Tyr Trp Pro Ala Arg Ala Gln Ser Met Thr Tyr Cys
        355                 360                 365

Ile Glu Trp Gln Pro Val Gly Gln Asp Gly Gly Leu Ala Thr Cys Ser
        370                 375                 380

Leu Thr Ala Pro Gln Asp Pro Asp Pro Ala Gly Met Ala Thr Tyr Ser
385                 390                 395                 400

Trp Ser Arg Glu Ser Gly Ala Met Gly Gln Glu Lys Cys Tyr Tyr Ile
                405                 410                 415

Thr Ile Phe Ala Ser Ala His Pro Glu Lys Leu Thr Leu Trp Ser Thr
            420                 425                 430

Val Leu Ser Thr Tyr His Phe Gly Gly Asn Ala Ser Ala Ala Gly Thr
        435                 440                 445

Pro His His Val Ser Val Lys Asn His Ser Leu Asp Ser Val Ser Val
        450                 455                 460

Asp Trp Ala Pro Ser Leu Leu Ser Thr Cys Pro Gly Val Leu Lys Glu
465                 470                 475                 480

Tyr Val Val Arg Cys Arg Asp Glu Asp Ser Lys Gln Val Ser Glu His
                485                 490                 495

Pro Val Gln Pro Thr Glu Thr Gln Val Thr Leu Ser Gly Leu Arg Ala
            500                 505                 510

Gly Val Ala Tyr Thr Val Gln Val Arg Ala Asp Thr Ala Trp Leu Arg
        515                 520                 525

Gly Val Trp Ser Gln Pro Gln Arg Phe Ser Ile Glu Val Gln Val Ser
        530                 535                 540

Asp Trp Leu Ile Phe Phe Ala Ser Leu Gly Ser Phe Leu Ser Ile Leu
545                 550                 555                 560

Leu Val Gly Val Leu Gly Tyr Leu Gly Leu Asn Arg Ala Ala Arg His
                565                 570                 575

Leu Cys Pro Pro Leu Pro Thr Pro Cys Ala Ser Ser Ala Ile Glu Phe
            580                 585                 590

Pro Gly Gly Lys Glu Thr Trp Gln Trp Ile Asn Pro Val Asp Phe Gln
        595                 600                 605

Glu Glu Ala Ser Leu Gln Glu Ala Leu Val Val Glu Met Ser Trp Asp
```

```
                            610                 615                 620
Lys Gly Glu Arg Thr Glu Pro Leu Glu Lys Thr Glu Leu Pro Glu Gly
625                 630                 635                 640

Ala Pro Glu Leu Ala Leu Asp Thr Glu Leu Ser Leu Glu Asp Gly Asp
                645                 650                 655

Arg Cys Lys Ala Lys Met
            660

<210> SEQ ID NO 152
<211> LENGTH: 360
<212> TYPE: DNA
<213> ORGANISM: Homo sapiens

<400> SEQUENCE: 152
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggcacatcc attacagtgg aaacacctac     180
tacaacccgt ccctcaagag tcgagttacc atatcagtag acacgtctaa gaatcagttc     240
tccctgaaac tgagctctgt gactgccgcg gacacggccg tgtattactg tgcgcgaaat     300
cgcgggttct actacggtat ggacgtctgg ggccaaggga ccacggtcac cgtctcctca     360

<210> SEQ ID NO 153
<211> LENGTH: 120
<212> TYPE: PRT
<213> ORGANISM: Homo sapiens

<400> SEQUENCE: 153

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly His Ile His Tyr Ser Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asn Arg Gly Phe Tyr Tyr Gly Met Asp Val Trp Gly Gln
            100                 105                 110

Gly Thr Thr Val Thr Val Ser Ser
        115                 120

<210> SEQ ID NO 154
<211> LENGTH: 23
<212> TYPE: PRT
<213> ORGANISM: Artificial Sequence
<220> FEATURE:
<223> OTHER INFORMATION: Honeybee melittin signal

<400> SEQUENCE: 154

Met Lys Phe Leu Val Asn Val Ala Leu Val Phe Met Val Val Tyr Ile
1               5                   10                  15

Ser Tyr Ile Tyr Ala Ala Ala
            20
```

```
<210> SEQ ID NO 155
<211> LENGTH: 6
<212> TYPE: PRT
<213> ORGANISM: Artificial Sequence
<220> FEATURE:
<223> OTHER INFORMATION: His Tag

<400> SEQUENCE: 155

His His His His His His
1               5
```

What is claimed is:

1. An isolated antigen binding protein that binds IL-23, comprising at least one heavy chain variable region comprising:
   a CDRH1 of SEQ ID NO: 91;
   a CDRH2 of SEQ ID NO:92; and
   a CDRH3 of SEQ ID NO: 93; and
   at least one light chain variable region comprising:
   a CDRL1 of SEQ ID NO: 62;
   a CDRL2 of SEQ ID NO:63; and
   a CDRL3 of SEQ ID NO:64.

2. An isolated antigen binding protein that binds IL-23 comprising a heavy chain variable region comprising amino acid residues 31-35, 50-65 and 99-113 of SEQ ID NO:31; and a light chain variable region comprising amino acid residues 23-36, 52-58 and 91-101 of SEQ ID NO:1.

3. An isolated antigen binding protein that binds IL-23 comprising
   a heavy chain variable region of SEQ ID NO: 31 and
   a light chain variable region of SEQ ID NO: 1.

4. An isolated antigen binding protein of claim 1, 2 or 3 wherein said antigen binding protein has at least one property selected from the group consisting of:
   a) reducing human IL-23 activity;
   b) reducing production of a proinflammatory cytokine;
   c) binding to human IL-23 with a $K_D$ of less than or equal to $5 \times 10^{-8}$ M;
   d) having a $K_{off}$ rate of less than or equal to $5 \times 10^{-6}$ l/s; and
   e) having an $IC_{50}$ of less than or equal to 400 pM.

5. A pharmaceutical composition comprising at least one antigen binding protein of claim 1, 2, or 3 and a pharmaceutically acceptable excipient.

6. A pharmaceutical composition comprising at least one antigen binding protein of claim 4 and a pharmaceutically acceptable excipient.

* * * * *